United States Patent
Sakamoto et al.

(10) Patent No.: US 12,403,132 B2
(45) Date of Patent: Sep. 2, 2025

(54) METHODS OF TREATING BONE MARROW FAILURE SYNDROMES AND COMPOSITIONS FOR USE IN THE SAME

(71) Applicant: The Board of Trustees of the Leland Stanford Junior University, Stanford, CA (US)

(72) Inventors: Kathleen Miho Sakamoto, Stanford, CA (US); Mark Wilkes, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 523 days.

(21) Appl. No.: 17/924,601

(22) PCT Filed: Jun. 24, 2021

(86) PCT No.: PCT/US2021/038987
§ 371 (c)(1),
(2) Date: Nov. 10, 2022

(87) PCT Pub. No.: WO2022/005879
PCT Pub. Date: Jan. 6, 2022

(65) Prior Publication Data
US 2023/0172917 A1 Jun. 8, 2023

Related U.S. Application Data

(60) Provisional application No. 63/046,877, filed on Jul. 1, 2020.

(51) Int. Cl.
*A61K 31/4375* (2006.01)
*A61K 31/155* (2006.01)
*A61K 36/258* (2006.01)
*A61P 7/00* (2006.01)

(52) U.S. Cl.
CPC ........ *A61K 31/4375* (2013.01); *A61K 31/155* (2013.01); *A61K 36/258* (2013.01); *A61P 7/00* (2018.01)

(58) Field of Classification Search
None
See application file for complete search history.

(56) References Cited

U.S. PATENT DOCUMENTS

| 9,334,502 B2 * | 5/2016 | Han ............... C12N 15/1137 |
| 2014/0243356 A1 | 8/2014 | Ruggero et al. |
| 2018/0185315 A1 | 7/2018 | Venn-Watson et al. |

FOREIGN PATENT DOCUMENTS

| WO | WO2014013231 A1 | 1/2014 |
| WO | WO2018213791 A1 | 11/2018 |
| WO | WO2018226758 A1 | 12/2018 |
| WO | WO2019086478 A1 | 5/2019 |

OTHER PUBLICATIONS

Huang et al., Tumor Biology (2015), 36(12), pp. 9147-9152.*
Kortenjann et al., European Journal of Immunology (2001), 31, pp. 3580-3587.*
Wilkes et al., Beyond mRNA: The role of non-coding RNAs in normal and aberrant hematopoiesis, Mol Genet Metab. Nov. 2017; 122(3): 28-38.
Wilkes et al., Diamond Blackfan anemia is mediated by hyperactive Nemo-like kinase, Nature communications 11, 3344, 2020.
Wilkes et al., Metformin-induced suppression of NLK improves erythropoiesis in Diamond Blackfan Anemia through Induction of miR-26a, Exp Hematol, Nov. 2020; 91:65-77.
Stefka et al., Anti-myeloma activity of MELK inhibitor OTS167: effects on drug-resistant myeloma cells and putative myeloma stem cell replenishment of malignant plasma cells, Blood Cancer J. Aug. 19, 2016; 6(8):e460.

* cited by examiner

*Primary Examiner* — Brian J Davis
(74) *Attorney, Agent, or Firm* — Bret E. Field; Bozicevic, Field & Francis LLP

(57) ABSTRACT

Methods of treating a subject for a bone marrow failure syndrome, e.g., DBA, are provided. Aspects of the methods include administering to the subject an effective amount of a Nemo-Like Kinase (NLK) inhibitor. Also provided are compositions that find use in practicing embodiment of the invention.

12 Claims, 43 Drawing Sheets

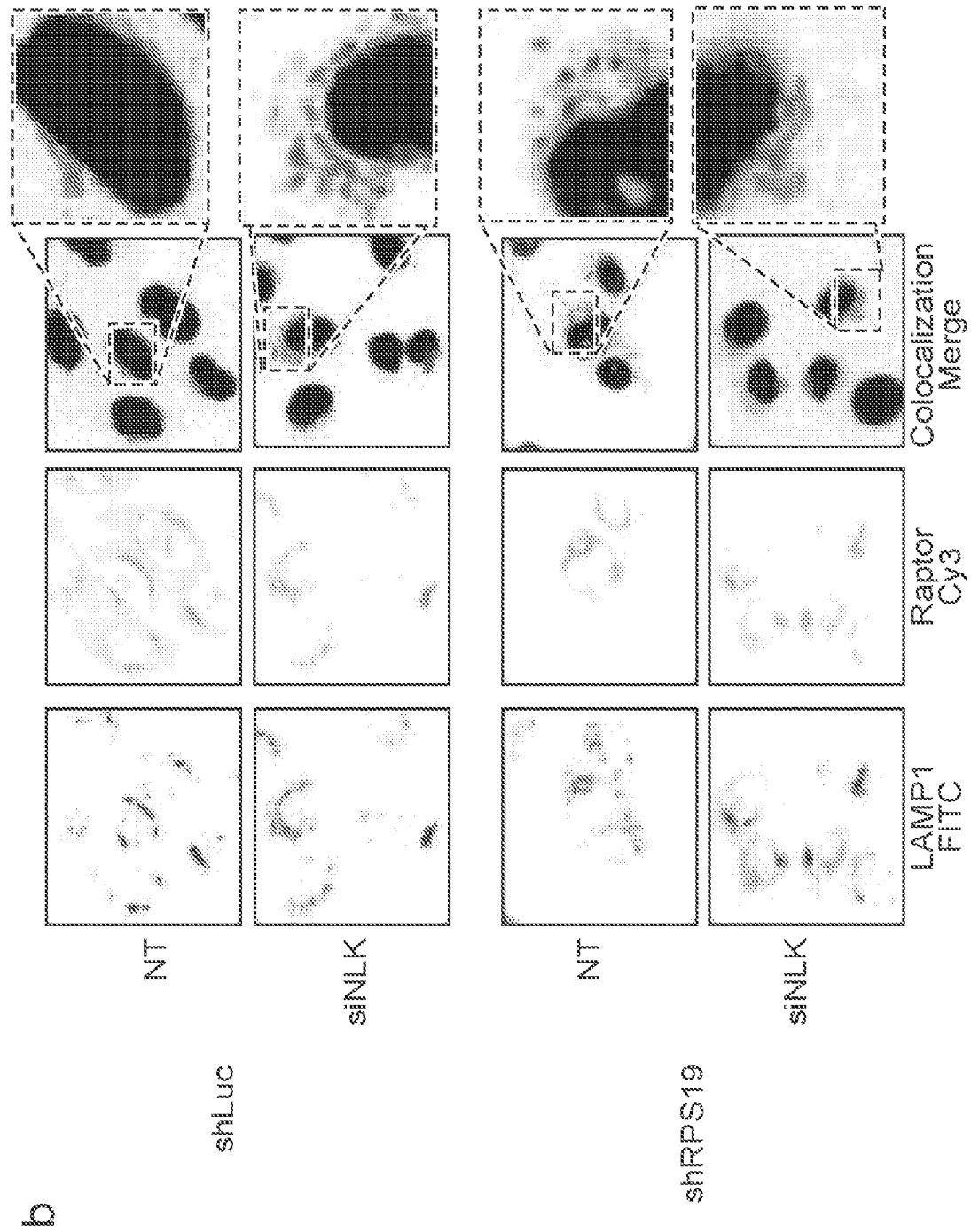

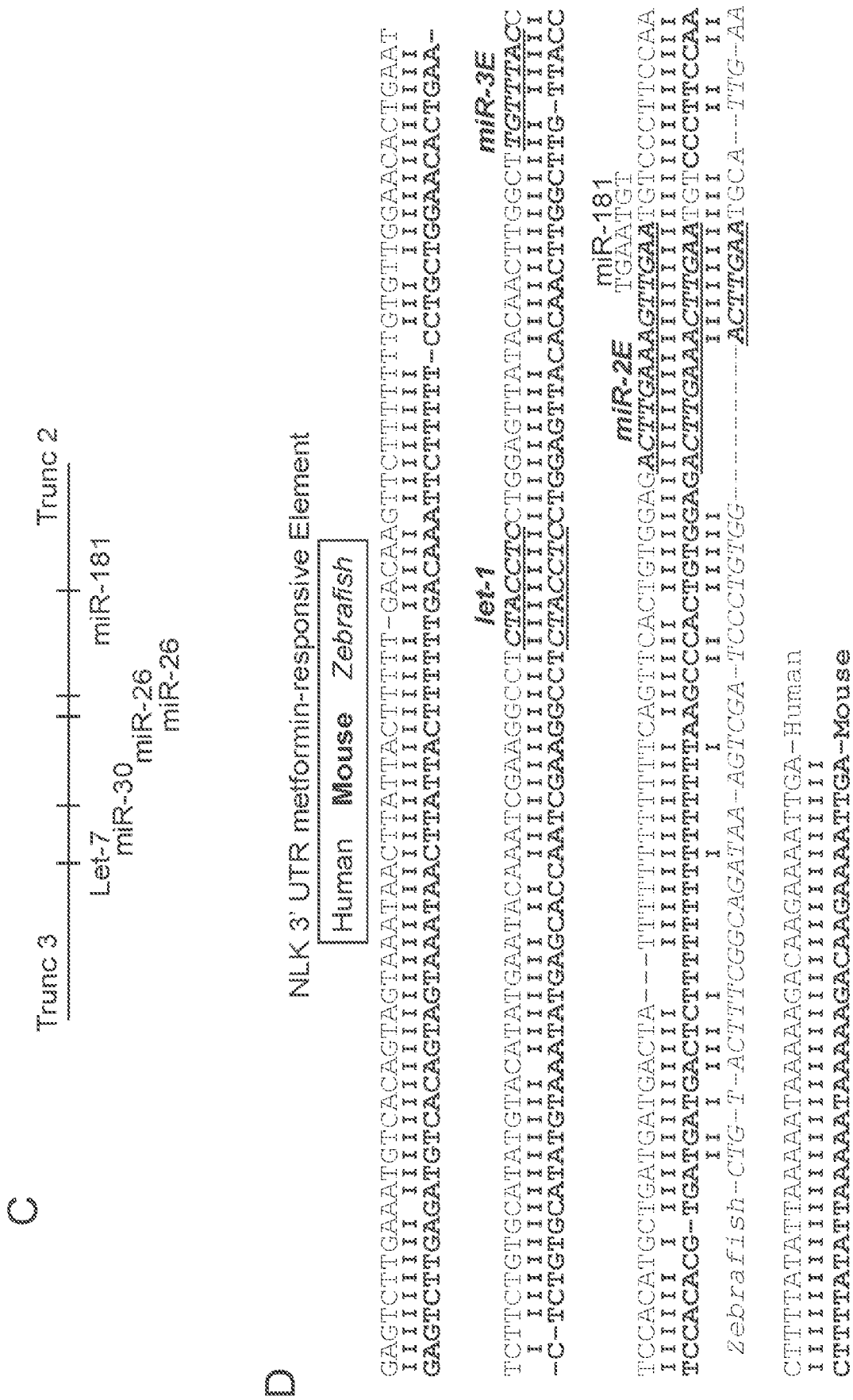

METHODS OF TREATING BONE MARROW FAILURE SYNDROMES AND COMPOSITIONS FOR USE IN THE SAME

CROSS REFERENCE TO RELATED APPLICATION

This application is a U.S. National Stage Application of PCT Application filed on Jun. 24, 2021, which application claims the benefit of the filing date of U.S. Provisional Application Ser. No. 63/046,877 filed on Jul. 1, 2020, the disclosure of which applications are herein incorporated by reference.

GOVERNMENT RIGHTS

This invention was made with Government support under contract W81XWH1910431 awarded by the Department of Defense. The Government has certain rights in the invention.

INTRODUCTION

Inherited bone marrow failure syndromes are disorders associated with one or more somatic abnormality that manifest as bone marrow failure. Bone marrow failure occurs when the bone marrow fails to produce enough healthy blood cells to keep up with the body's needs. The bone marrow failure can be characterized by arising from single or multiple cell lineage and may present in childhood or adulthood. Inherited bone marrow failure syndromes include: Diamond Blackfan Anemia, Fanconi Anemia, Dyskeratosis Congenita, Shwachman-Diamond Syndrome, Congenital Amegakaryocytic Thrombocytopenia and Severe Congenital Neutropenia.

Diamond Blackfan Anemia (DBA) is a rare congenital bone marrow failure syndrome that results in significant anemia requiring steroids or other treatment and red blood cell transfusions. DBA patients can have significant toxicity resulting from treatment, including immunosuppression from steroids and iron overload from chronic transfusions. Therefore, new therapies are needed.

SUMMARY

Methods of treating a subject for a bone marrow failure syndrome, e.g., DBA, are provided. Aspects of the methods include administering to the subject an effective amount of a Nemo-Like Kinase (NLK) inhibitor. Also provided are compositions that find use in practicing embodiment of the invention.

DETAILED DESCRIPTION

Figure 1:
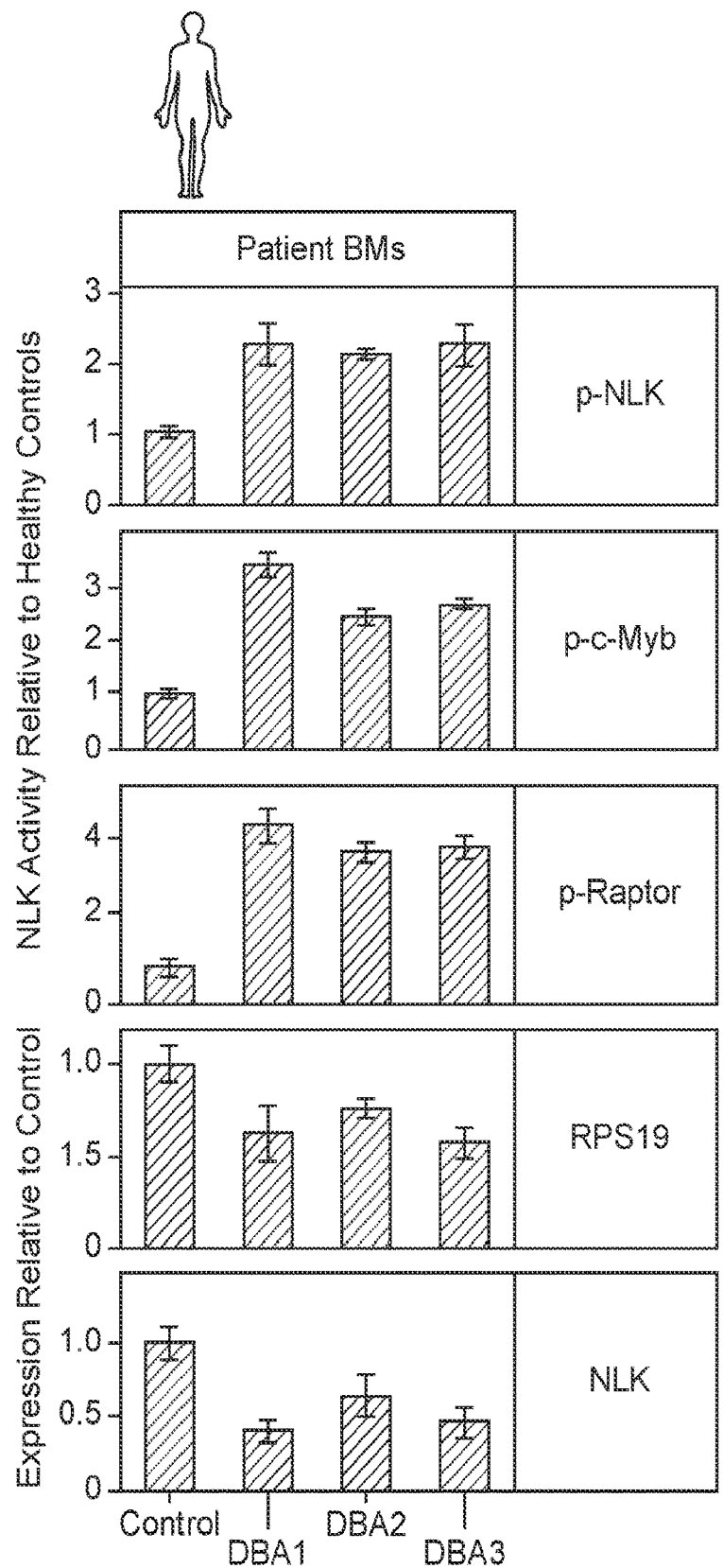
FIG. 1. NLK is hyperactivated in DBA patient bone marrow, iPSCs, and murine models of DBA. (a) NLK was immunopurified from 5000 bone marrow mononuclear cells derived from bone marrow aspirates of healthy control and three DBA patients carrying RPS19 mutations. Immunopurified NLK activity was assessed by kinase assay measuring in vitro phosphorylation of NLK, c-Myb and raptor. Expression of NLK and RPS19 was assessed by qRT-PCR and normalized against 7SL. (b) Cord blood CD34+ progenitors were transduced with lentivirus co-expressing shRNA against luciferase (shLuc), RPS19 (shRPS19) or RPL11 (shRPL11) and GFP. After 36 hours GFP+ cells were differentiated in erythroid media for the indicated days prior to immunopurifying NLK for kinase assay and assessment of RPS19/RPL11 and NLK expression by qRT-PCR. Solid circles indicate shLuc while open circles indicate shRPS19 or shRPL11. (c) Lin-cKit+ hematopoietic progenitors were obtained from mouse embryos expressing tetracycline-inducible shRNA against RPS19, at day E14.5. Cells were grown in the presence or absence of doxycycline for 8 days and subjected to NLK kinase assay qRT-PCR for expression of murine RPS19 and NLK (c—left). Lin-Kit+ progenitors were purified from bone marrow of 3 RPL11$^{+/+}$ and 3 RPL11$^{+/lox}$ tamoxifen-treated mice and scrutinized for NLK activity by kinase assay, as well as NLK and RPL11 expression by qRT-PCR (c—right). (d) Cord blood CD34+ progenitors were transduced with lentivirus expressing shRNA against luciferase (shLuc) or RPS19 (shRPS19) co-expressing GFP. Cells were also transduced with or without shRNA against p53 co-expressing mCherry. After 36 hours, GFP+ and GFP+, mCherry+ cells were differentiated in erythroid media for 8 days, followed by NLK kinase assay and qRT-PCR analysis of NLK and p53 expression.
Figure 1:
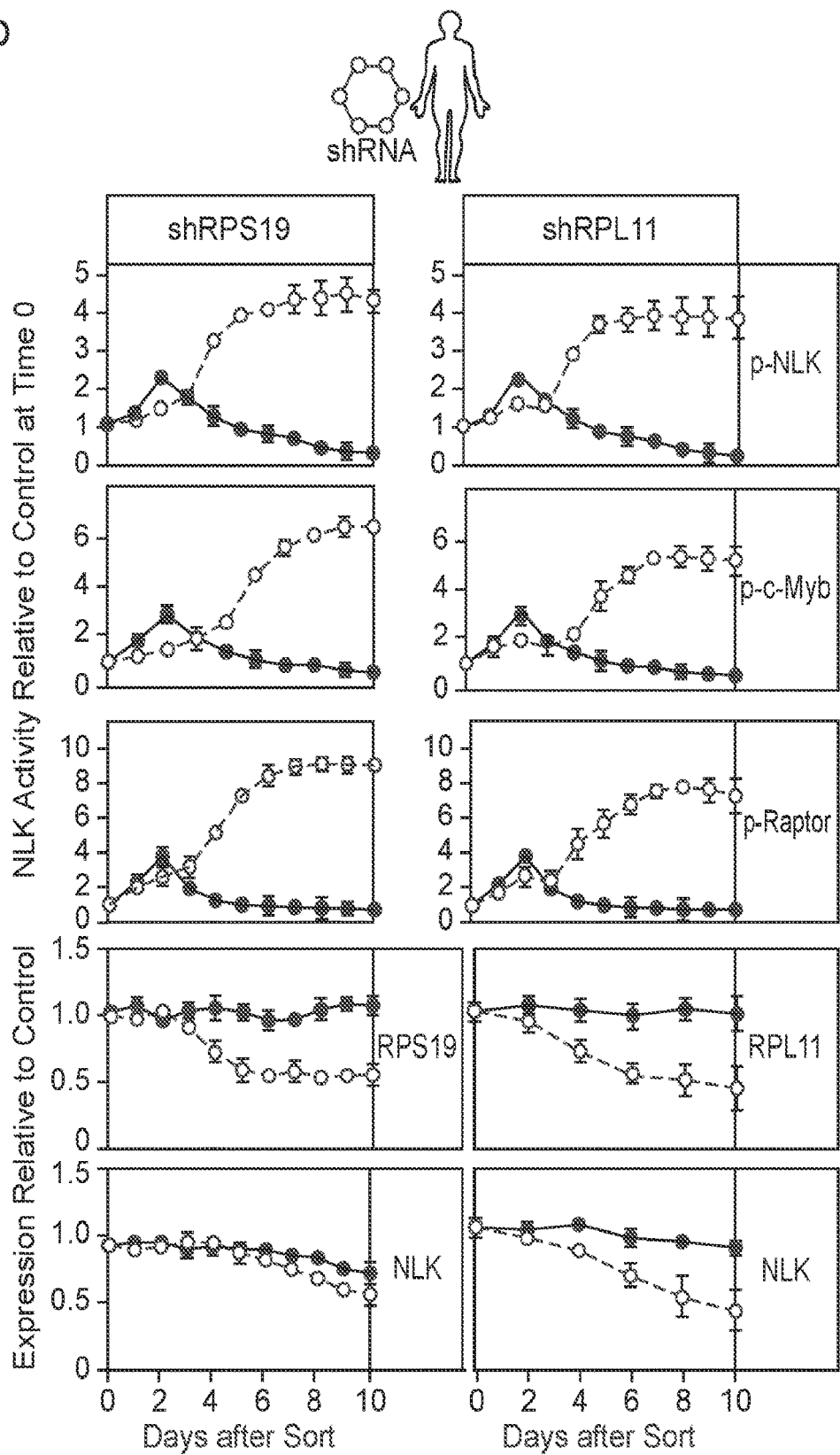
Figure 1:
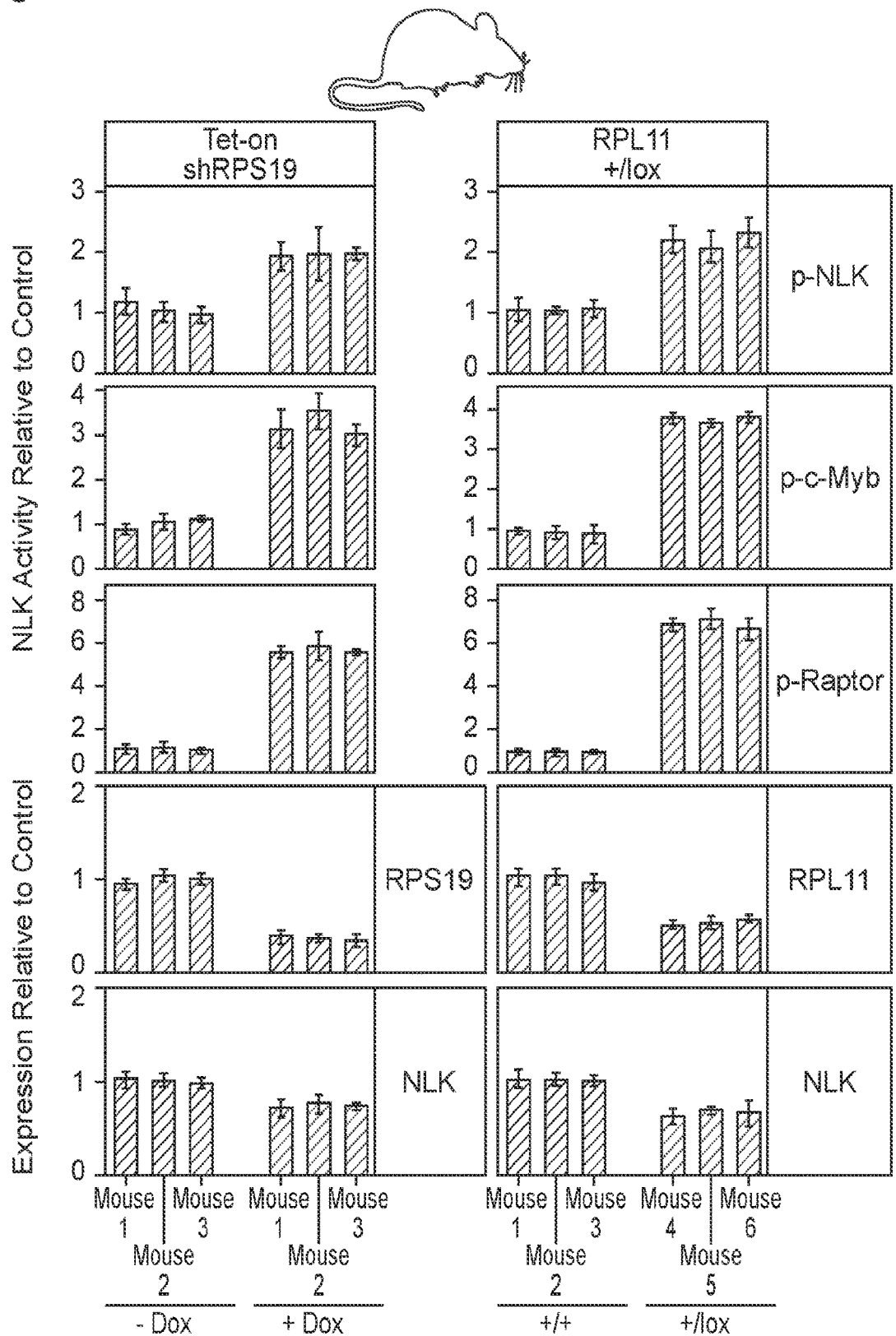
Figure 1:
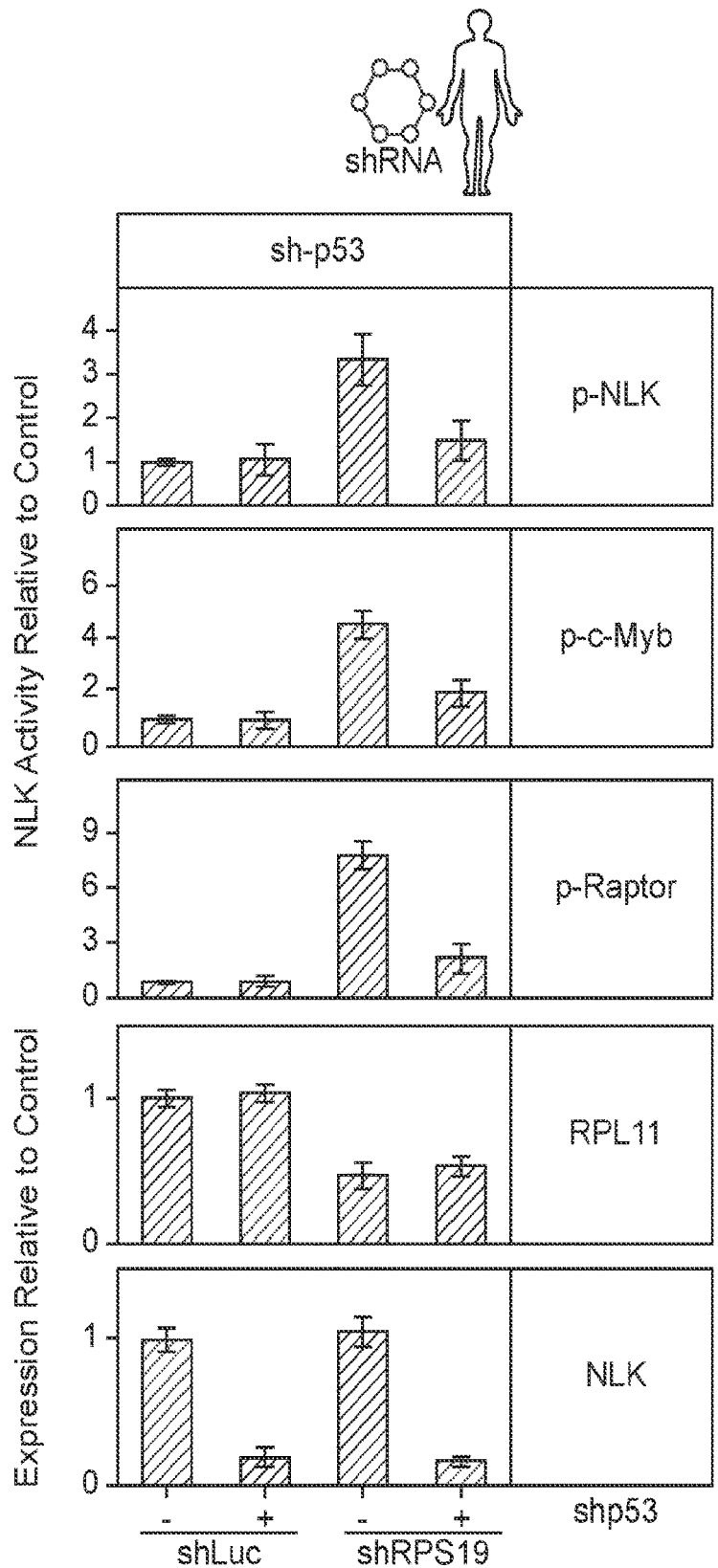

Methods of treating a subject for a bone marrow failure syndrome, e.g., DBA, are provided. Aspects of the methods include administering to the subject an effective amount of a Nemo-Like Kinase (NLK) inhibitor. Also provided are compositions that find use in practicing embodiment of the invention.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

Methods

As reviewed above, methods of treating a subject for a bone marrow failure syndrome, e.g., DBA, are provided. Bone marrow failure occurs when the bone marrow fails to produce enough healthy blood cells to keep up with the body's needs. In some instances, the bone marrow failure syndrome is an inherited (e.g., congenital) bone marrow failure syndrome. Inherited bone marrow failure syndromes are disorders associated with one or more somatic abnormality that manifest as bone marrow failure. The bone marrow failure can be characterized by arising from single or multiple cell lineage and may present in childhood or adulthood. Inherited bone marrow failure syndromes include: Diamond Blackfan Anemia, Fanconi Anemia, Dyskeratosis Congenita, Shwachman-Diamond Syndrome, Congenital Amegakaryocytic Thrombocytopenia and Severe Congenital Neutropenia.

In some instances, the bone marrow failure syndrome that is treated by embodiments of methods of the invention is Diamond Blackfan Anemia (DBA). As reviewed above, DBA is a congenital bone marrow failure syndrome usually diagnosed within the first year of life. Approximately 70% of DBA patients possess a mutation in one of 19 genes that encode ribosomal proteins, with mutations in Ribosomal Protein S19 (RPS19) accounting for over 25% and RPL11 comprising approximately 5% of cases. Complete loss of ribosomal components is not viable, while mutations resulting in haploinsufficiency cause erythropoiesis failure due to a block in differentiation of early erythroid progenitors. Erythroid specificity of ribosomal insufficiency in DBA is largely due to reduced translational efficiency of genes possessing a short, complex 5'UTR that is highly upregulated, particularly GATA1.

The terms "individual," "host," "subject," and "patient" are used interchangeably herein, and refer to an animal, including, but not limited to, human and non-human primates, including simians and humans; rodents, including rats and mice; bovines; equines; ovines; felines; canines; and the like. "Mammal" means a member or members of any mammalian species, and includes, by way of example, canines; felines; equines; bovines; ovines; rodentia, etc. and primates, e.g., non-human primates, and humans. Non-human animal models, e.g., mammals, e.g. non-human primates, murines, lagomorpha, etc. may be used for experimental investigations. In some instances, the subject is one that has been diagnosed as having a bone marrow failure syndrome. For example, the subject may be one that has been diagnosed as having DBA. DBA may be diagnosed using any convenient protocol, such as that described in Lipton & Ellis, "Diamond Blackfan Anemia: Diagnosis, Treatment and Molecular Pathogenesis," Hematol. Oncol. Clin. North Am. (2009) 23:261-282.

By "treatment" it is meant that at least an amelioration of one or more symptoms associated with a bone marrow failure syndrome, e.g., DBA, afflicting the subject is achieved. As such, symptoms that may be ameliorated by embodiments of the invention include, but are not limited to: rapid heartbeat, pale skin, sleepiness, irritability, poor appetite, and weakness. Amelioration is used in a broad sense to refer to at least a reduction in the magnitude of a parameter, e.g., a symptom associated with the impairment being treated, e.g., as described above. As such, treatment also includes situations where a pathological condition, or at least symptoms associated therewith, are completely inhibited, e.g., prevented from happening, or stopped, e.g., terminated, such that the adult mammal no longer suffers from the impairment, or at least the symptoms that characterize the impairment. In some instances, "treatment", "treating" and the like refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" may be any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. Treatment may result in a variety of different physical manifestations, e.g., modulation in gene expression, increased neurogenesis, rejuvenation of tissue or organs, etc. Treatment of ongoing disease, where the treatment stabilizes or reduces the undesirable clinical symptoms of the patient, occurs in some embodiments. Such treatment may be performed prior to complete loss of function in the affected tissues. The subject therapy may be administered during the symptomatic stage of the disease, and in some cases after the symptomatic stage of the disease.

Aspects of embodiments of the methods include administering to the subject an effective amount of a Nemo-Like Kinase (NLK) inhibitor. NLK is a 515-amino acid protein has a kinase domain between amino acids 127 and 415. Homo sapiens nemo like kinase (NLK), mRNA has been assigned NCBI Reference Sequence: NM_016231.5 and nemo-like kinase [Homo sapiens] and been assigned GenBank: AAF04857.1. NLK is an evolutionarily conserved serine/threonine kinase. NLK belongs to the proline directed protein kinase superfamily, which consists of mitogen activated protein kinases (MAPKs) and cyclin-dependent protein kinases (CDKs). NLK contributes to cell proliferation, differentiation, apoptosis and morphological changes during early embryogenesis and nervous system development and is involved in the pathogenesis of several human cancers. Overexpression of NLK in colorectal, laryngeal, and non-small cell lung cancer, as well as osteosarcomas and neuroblastomas correlate with poor prognosis and more aggressive tumors. NLK regulates a diverse array of signaling pathways, including the Wnt/β-catenin, Activin, IL-6, and Notch signaling pathways. In Wnt-1-stimulated HEK293T cells, NLK phosphorylates c-Myb, priming it for ubiquitination by the E3-ubiquitin kinase Fbxw7 and subsequent proteasome degradation. Raptor is another reported substrate of NLK. In a kinome library screen designed to identify mTOR inhibitors during oxidative and hyperosmotic stress, NLK activation was detected. Subsequent phosphorylation of raptor at S863 prevented mTOR-associated raptor from localizing to the lysosomal membrane for activation. Additional NLK substrates regulated by NLK phosphorylation include ATF5, FoxO1, Lef1 and HDAC.

In practicing embodiments of the invention, any convenient NLK inhibitor may be employed. Examples of NLK inhibitors include, but are not limited to: small molecule inhibitors; NLK expression inhibitors; NLK binding agents; and the like.

In some instances, the NLK inhibitor is a small molecule NLK inhibitor. Naturally occurring or synthetic small molecule compounds of interest include numerous chemical classes, such as organic molecules, e.g., small organic compounds having a molecular weight of more than 50 and less than about 2,500 daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below.

Specific examples of small molecule NLK inhibitors include, but are not limited to: OTS167, INK128, AST487, BIRB796, SB203580, SB220025, VX-702, PD-196316, SD208, SB431542, PD-173955, AST-487, foretinib, staurosporine, dasatinib, PP-242, sorafenib, lestaurtinib, doramapimod, Galunisertib, Tanzisertib and the like.

In certain embodiments, the administered active agent is a NLK binding agent, such as an NLK specific binding member. In general, useful NLK specific binding members exhibit an affinity (Kd) for a target nemo-like kinase, such as human NLK or murine Nlk, that is sufficient to provide for the activity. As used herein, the term "affinity" refers to the equilibrium constant for the reversible binding of two agents; "affinity" can be expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of a specific binding member to a target protein can be, for example, from about 100 nanomolar (nM) to about 0.1 nM, from about 100 nM to about 1 picomolar (pM), or from about 100 nM to about 1 femtomolar (fM) or more. The term "binding" refers to a direct association between two molecules, due to, for example, covalent, electrostatic, hydrophobic, and ionic and/or hydrogen-bond interactions, including interactions such as salt bridges and water bridges. In some embodiments, the antibodies bind human VCAM-1 with nanomolar affinity or picomolar affinity. In some embodiments, the antibodies bind human NLK with a Kd of less than about 100 nM, 50 nM, 20 nM, 20 nM, or 1 nM. In some embodiments, the affinity between the binding member active agent in a binding complex with NLK is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less. "Affinity" refers to the strength of binding, increased binding affinity being correlated with a lower KD. In an embodiment, affinity is determined by surface plasmon resonance (SPR), e.g. as used by Biacore systems. The affinity of one molecule for another molecule is determined by measuring the binding kinetics of the interaction, e.g. at 25° C.

Antibody specific binding members that may be employed include full antibodies or immunoglobulins of any isotype, as well as fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. Also encompassed by the term are Fab', Fv, F(ab')2, and or other antibody fragments that retain specific binding to antigen, and monoclonal antibodies. An antibody may be monovalent or bivalent.

"Antibody fragments" comprise a portion of an intact antibody, for example, the antigen binding or variable region of the intact antibody. Examples of antibody fragments include Fab, Fab', F(ab')2, and Fv fragments; diabodies;

linear antibodies (Zapata et al., Protein Eng. 8 (10): 1057-1062 (1995)); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain (CH1) of the heavy chain. Fab fragments differ from Fab' fragments by the addition of a few residues at the carboxyl terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the VH and VL domains of antibody, wherein these domains are present in a single polypeptide chain. In some embodiments, the Fv polypeptide further comprises a polypeptide linker between the VH and VL domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

Antibodies that may be used in connection with the present disclosure thus can encompass monoclonal antibodies, polyclonal antibodies, bispecific antibodies, Fab antibody fragments, F(ab) 2 antibody fragments, Fv antibody fragments (e.g., VH or VL), single chain Fv antibody fragments and dsFv antibody fragments. Furthermore, the antibody molecules may be fully human antibodies, humanized antibodies, or chimeric antibodies. In some embodiments, the antibody molecules are monoclonal, fully human antibodies.

The antibodies that may be used in connection with the present disclosure can include any antibody variable region, mature or unprocessed, linked to any immunoglobulin constant region. If a light chain variable region is linked to a constant region, it can be a kappa chain constant region. If a heavy chain variable region is linked to a constant region, it can be a human gamma 1, gamma 2, gamma 3 or gamma 4 constant region, more preferably, gamma 1, gamma 2 or gamma 4 and even more preferably gamma 1 or gamma 4.

In some embodiments, fully human monoclonal antibodies directed against NLK are generated using transgenic mice carrying parts of the human immune system rather than the mouse system.

Minor variations in the amino acid sequences of antibodies or immunoglobulin molecules are encompassed by the present invention, providing that the variations in the amino acid sequence maintain at least 75%, e.g., at least 80%, 90%, 95%, or 99% of the sequence. In particular, conservative amino acid replacements are contemplated. Conservative replacements are those that take place within a family of amino acids that are related in their side chains. Whether an amino acid change results in a functional peptide can readily be determined by assaying the specific activity of the polypeptide derivative. Fragments (or analogs) of antibodies or immunoglobulin molecules, can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Sequence motifs and structural conformations may be used to define structural and functional domains in accordance with the invention.

Agents finding use in the methods of the invention also include NLK expression inhibiting agents, i.e., agents that inhibit expression of the RNA and/or protein from the gene, such that it changes the expression of the RNA or protein from the target gene in some manner. In these instances, the agent may change expression of the RNA or protein in a number of different ways. In certain embodiments, the agent is one that reduces, including inhibits, expression of a NLK protein. Inhibition of NLK protein expression may be accomplished using any convenient protocol, including use of an agent that inhibits NLK protein expression, such as, but not limited to: interfering nucleic acids, e.g., RNAi agents, antisense agents, agents that interfere with a transcription factor binding to a promoter sequence of the NLK gene, or inactivation of the NLK gene, e.g., through recombinant techniques, etc.

In some embodiments, an interfering nucleic acid is used to interfere with production of NLK transcripts and production of NLK polypeptide. Interfering nucleic acids include small nucleic acid molecules, such as a short interfering nucleic acid (siNA), a short interfering RNA (siRNA), a double-stranded RNA (dsRNA), a micro-RNA (miRNA), and a short hairpin RNA (shRNA). The terms "short interfering nucleic acid," "siNA," "short interfering RNA," "siRNA," "short interfering nucleic acid molecule," "short interfering oligonucleotide molecule," and "chemically-modified short interfering nucleic acid molecule" as used herein refer to any nucleic acid molecule capable of inhibiting or down regulating gene expression, for example by mediating RNA interference "RNAi" or gene silencing in a sequence-specific manner. Design of RNAi molecules, given a target gene, is routine in the art. See also US 2005/0282188 (which is incorporated herein by reference) as well as references cited therein. See, e.g., Pushparaj et al. Clin Exp Pharmacol Physiol. 2006 May-June; 33 (5-6):

504-10; Lutzelberger et al. Handb Exp Pharmacol. 2006; (173): 243-59; Aronin et al. Gene Ther. 2006 March; 13 (6): 509-16; Xie et al. Drug Discov Today. 2006 January; 11 (1-2): 67-73; Grunweller et al. Curr Med Chem. 2005; 12 (26): 3143-61; and Pekaraik et al. Brain Res Bull. 2005 Dec. 15; 68 (1-2): 115-20. Epub 2005 Sep. 9.

Methods for design and production of siRNAs to a desired target are known in the art, and their application to tau genes for the purposes disclosed herein will be readily apparent to the ordinarily skilled artisan, as are methods of production of siRNAs having modifications (e.g., chemical modifications) to provide for, e.g., enhanced stability, bioavailability, and other properties to enhance use as therapeutics. In addition, methods for formulation and delivery of siRNAs to a subject are also well known in the art. See, e.g., US 2005/0282188; US 2005/0239731; US 2005/0234232; US 2005/0176018; US 2005/0059817; US 2005/0020525; US 2004/0192626; US 2003/0073640; US 2002/0150936; US 2002/0142980; and US2002/0120129, each of which are incorporated herein by reference.

Publicly available tools to facilitate design of siRNAs are available in the art. See, e.g., DEQOR: Design and Quality Control of RNAi (available on the internet at cluster-1.mpi-cbg.de/Deqor/deqor.html). See also, Henschel et al. Nucleic Acids Res. 2004 Jul. 1; 32 (Web Server issue): W113-20. DEQOR is a web-based program which uses a scoring system based on state-of-the-art parameters for siRNA design to evaluate the inhibitory potency of siRNAs. DEQOR, therefore, can help to predict (i) regions in a gene that show high silencing capacity based on the base pair composition and (ii) siRNAs with high silencing potential for chemical synthesis. In addition, each siRNA arising from the input query is evaluated for possible cross-silencing activities by performing BLAST searches against the transcriptome or genome of a selected organism. DEQOR can therefore predict the probability that an mRNA fragment will cross-react with other genes in the cell and helps researchers to design experiments to test the specificity of siRNAs or chemically designed siRNAs.

siNA molecules can be of any of a variety of forms. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. siNA can also be assembled from two separate oligonucleotides, where one strand is the sense strand and the other is the antisense strand, wherein the antisense and sense strands are self-complementary. In this embodiment, each strand comprises nucleotide sequence that is complementary to nucleotide sequence in the other strand; such as where the antisense strand and sense strand form a duplex or double stranded structure, for example wherein the double stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the siNA molecule are complementary to the target nucleic acid or a portion thereof).

Alternatively, the siNA can be assembled from a single oligonucleotide, where the self-complementary sense and antisense regions of the siNA are linked by a nucleic acid-based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof.

The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (e.g., where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, Cell, 110, 563-574 and Schwarz et al., 2002, Molecular Cell, 10, 537-568), or 5',3'-diphosphate.

In certain embodiments, the siNA molecule contains separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der Waals interactions, hydrophobic interactions, and/or stacking interactions. In certain embodiments, the siNA molecules comprise nucleotide sequence that is complementary to nucleotide sequence of a target gene. In another embodiment, the siNA molecule interacts with nucleotide sequence of a target gene in a manner that causes inhibition of expression of the target gene.

As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. siNAs do not necessarily require the presence of nucleotides having a 2'-hydroxy group for mediating RNAi and as such, siNA molecules of the invention optionally do not include any ribonucleotides (e.g., nucleotides having a 2'—OH group). Such siNA molecules that do not require the presence of ribonucleotides within the siNA molecule to support RNAi can however have an attached linker or linkers or other attached or associated groups, moieties, or chains containing one or more nucleotides with 2'—OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON."

As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siNA molecules of the invention can be used to epigenetically silence a target gene at the post-transcriptional level or the pre-transcriptional level. In a non-limiting example, epigenetic regulation of gene expression by siNA molecules of the invention can result from siNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

siNA molecules contemplated herein can comprise a duplex forming oligonucleotide (DFO) see, e.g., WO 05/019453; and US 2005/0233329, which are incorporated herein by reference). siNA molecules also contemplated herein include multifunctional siNA, (see, e.g., WO 05/019453 and US 2004/0249178). The multifunctional siNA can comprise sequence targeting, for example, two regions of nlk.

siNA molecules contemplated herein can comprise an asymmetric hairpin or asymmetric duplex. By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a loop region comprising about 4 to about 12 (e.g., about 4, 5, 6, 7, 8, 9, 10, 11, or 12) nucleotides, and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein. By "asymmetric duplex" as used herein is meant a siNA molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex siNA molecule of the invention can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region.

Stability and/or half-life of siRNAs can be improved through chemically synthesizing nucleic acid molecules with modifications (base, sugar and/or phosphate) can prevent their degradation by serum ribonucleases, which can increase their potency (see e.g., Eckstein et al., International Publication No. WO 92/07065; Perrault et al., 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; Gold et al., U.S. Pat. No. 6,300,074; and Burgin et al., supra; all of which are incorporated by reference herein, describing various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. International Publication PCT No. WO 93/15187; Sproat, U.S. Pat. No. 5,334,711 and Beigelman et al., 1995, J. Biol. Chem., 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, Tetrahedron Lett., 39, 1131; Eamshaw and Gait, 1998, Biopolymers (Nucleic Acid Sciences), 48, 39-55; Verma and Eckstein, 1998, Annu. Rev. Biochem., 67, 99-134; and Burlina et al., 1997, Bioorg. Med. Chem., 5, 1999-2010; each of which are hereby incorporated in their totality by reference herein). In view of such teachings, similar modifications can be used as described herein to modify the siNA nucleic acid molecules of disclosed herein so long as the ability of siNA to promote RNAi in cells is not significantly inhibited.

Short interfering nucleic acid (siNA) molecules having chemical modifications that maintain or enhance activity are contemplated herein. Such a nucleic acid is also generally more resistant to nucleases than an unmodified nucleic acid. Accordingly, the in vitro and/or in vivo activity should not be significantly lowered. Nucleic acid molecules delivered exogenously are generally selected to be stable within cells at least for a period sufficient for transcription and/or translation of the target RNA to occur and to provide for modulation of production of the encoded mRNA and/or polypeptide so as to facilitate reduction of the level of the target gene product.

Production of RNA and DNA molecules can be accomplished synthetically and can provide for introduction of nucleotide modifications to provide for enhanced nuclease stability. (see, e.g., Wincott et al., 1995, Nucleic Acids Res. 23, 2677; Caruthers et al., 1992, Methods in Enzymology 211, 3-19, incorporated by reference herein. In one embodiment, nucleic acid molecules of the invention include one or more (e.g., about 1, 2, 3, 4, 5, 6, 7, 8, 9, 10, or more)

G-clamp nucleotides, which are modified cytosine analogs which confer the ability to hydrogen bond both Watson-Crick and Hoogsteen faces of a complementary guanine within a duplex, and can provide for enhanced affinity and specificity to nucleic acid targets (see, e.g., Lin et al. 1998, J. Am. Chem. Soc., 120, 8531-8532). In another example, nucleic acid molecules can include one or more (e.g., about 1, 2, 3, 4, 5, 6, 7, 8, 9, 10, or more) LNA "locked nucleic acid" nucleotides such as a 2',4'-C methylene bicyclo nucleotide (see, e.g., Wengel et al., WO 00/66604 and WO 99/14226).

siNA molecules can be provided as conjugates and/or complexes, e.g., to facilitate delivery of siNA molecules into a cell. Exemplary conjugates and/or complexes include those composed of an siNA and a small molecule, lipid, cholesterol, phospholipid, nucleoside, antibody, toxin, negatively charged polymer (e.g., protein, peptide, hormone, carbohydrate, polyethylene glycol, or polyamine). In general, the transporters described are designed to be used either individually or as part of a multi-component system, with or without degradable linkers. These compounds can improve delivery and/or localization of nucleic acid molecules into cells in the presence or absence of serum (see, e.g., U.S. Pat. No. 5,854,038). Conjugates of the molecules described herein can be attached to biologically active molecules via linkers that are biodegradable, such as biodegradable nucleic acid linker molecules.

In some instances, the interfering nucleic acid is a micro-RNA. Any convenient micro-RNA that inhibits expression of NLK may be employed. In some instances, the micro-RNA is one that binds to the NLK 3'UTR, where examples of such micro-RNAs include, but are not limited to miR-26a, miR-181, miR-208, miR-199, miR-101, miR-221, and the like. In such instances, the micro-RNA may be employed per se, or an agent that upregulates expression of the micro-RNA, such as metformin, ginsenoside Rb1 and the like may be employed.

Interfering RNAs may be generated exogenously by chemical synthesis, by in vitro transcription, or by cleavage of longer double-stranded RNA with dicer or another appropriate nuclease with similar activity. Chemically synthesized interfering RNAs, produced from protected ribonucleoside phosphoramidites using a conventional DNA/RNA synthesizer, may be obtained from commercial suppliers such as Ambion Inc. (Austin, Tex.), Invitrogen (Carlsbad, Calif.), or Dharmacon (Lafayette, Colo.). Interfering RNAs are purified by extraction with a solvent or resin, precipitation, electrophoresis, chromatography, or a combination thereof, for example. Alternatively, interfering RNA may be used with little if any purification to avoid losses due to sample processing.

Interfering RNAs can also be expressed endogenously from plasmid or viral expression vectors or from minimal expression cassettes, for example, polymerase chain reaction (PCR)-generated fragments comprising one or more promoters and an appropriate template or templates for the interfering RNA. Examples of commercially available plasmid-based expression vectors for shRNA include members of the pSilencer series (Ambion, Austin, Tex.) and pCpG-siRNA (InvivoGen, San Diego, Calif.). Viral vectors for expression of interfering RNA may be derived from a variety of viruses including adenovirus, adeno-associated virus, lentivirus (e.g., HIV, FIV, and EIAV), and herpes virus. Examples of commercially available viral vectors for shRNA expression include pSilencer adeno (Ambion, Austin, Tex.) and pLenti6/BLOCK-iT.TM.-DEST (Invitrogen, Carlsbad, Calif.). Selection of viral vectors, methods for expressing the interfering RNA from the vector and methods of delivering the viral vector are within the ordinary skill of one in the art. Examples of kits for production of PCR-generated shRNA expression cassettes include Silencer Express (Ambion, Austin, Tex.) and siXpress (Mirus, Madison, Wis.).

An interfering RNA can be delivered in a delivery system that provides tissue targetable delivery. In addition, a suitable formulation for an interfering nucleic acid can include one or more additional properties: 1) nucleic acid binding into a core that can release the siRNA into the cytoplasm; 2) protection from non-specific interactions; 3) and tissue targeting that provides cell uptake. In some embodiments, the composition comprises a modular polymer conjugate targeting hippocampal neurons (e.g., interneurons) by coupling a peptide ligand specific for those cells to one end of a protective polymer, coupled at its other end to a cationic carrier for nucleic acids. For example, a suitable polymer conjugate can have three functional domains: peptide ligand specific for a target cell; protective polymer; and cationic carrier for nucleic acids. Another suitable formulation includes surface coatings attached to a preformed nanoparticle.

Suitable formulations for delivery of an interfering nucleic acid include polymers, polymer conjugates, lipids, micelles, self-assembly colloids, nanoparticles, sterically stabilized nanoparticles, and ligand-directed nanoparticles.

In some instances, antisense molecules can be used to down-regulate expression of a NLK gene in the cell. The anti-sense reagent may be antisense oligodeoxynucleotides (ODN), particularly synthetic ODN having chemical modifications from native nucleic acids, or nucleic acid constructs that express such anti-sense molecules as RNA. The antisense sequence is complementary to the mRNA of the targeted protein, and inhibits expression of the targeted protein. Antisense molecules inhibit gene expression through various mechanisms, e.g., by reducing the amount of mRNA available for translation, through activation of RNAse H, or steric hindrance. One or a combination of antisense molecules may be administered, where a combination may include multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. Short oligonucleotides, of from 7 to 8 bases in length, can be strong and selective inhibitors of gene expression (see Wagner et al., Nature Biotechnol. (1996) 14:840-844).

A specific region or regions of the endogenous sense strand mRNA sequence are chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra.) Oligonucleotides may be chemically modified from the native phosphodiester structure, in order to increase their intracellular stability and binding affinity. A number of such modifications have been described in the literature, which alter the chemistry of the backbone, sugars or heterocyclic bases. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O-5'-S-phosphorothioate, 3'-S-5'-O-phosphorothioate, 3'-CH.sub.2-5'-O-phosphonate and 3'—NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine, 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. Nucl. Acids Res. (1995) 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. Appl. Biochem. Biotechnol. (1995) 54:43-56.

In another embodiment, the NLK gene is inactivated so that it no longer expresses a functional protein. By inactivated is meant that the gene, e.g., coding sequence and/or regulatory elements thereof, is genetically modified so that it no longer expresses a functional NLK protein, e.g., at least with respect to NLK involvement in the target bone marrow failure syndrome, e.g., DBA. The alteration or mutation may take a number of different forms, e.g., through deletion of one or more nucleotide residues, through exchange of one or more nucleotide residues, and the like. One means of making such alterations in the coding sequence is by homologous recombination. Methods for generating targeted gene modifications through homologous recombination are known in the art, including those described in: U.S. Pat. Nos. 6,074,853; 5,998,209; 5,998,144; 5,948,653; 5,925,544; 5,830,698; 5,780,296; 5,776,744; 5,721,367; 5,614,396; 5,612,205; the disclosures of which are herein incorporated by reference.

Also of interest in certain embodiments are dominant negative mutants of NLK proteins, where expression of such mutants in the cell result in a modulation, e.g., decrease, in NLK mediated bone marrow failure syndrome. Dominant negative mutants of NLK are mutant proteins that exhibit dominant negative NLK activity. As used herein, the term "dominant-negative NLK activity" or "dominant negative activity" refers to the inhibition, negation, or diminution of certain particular activities of NLK, and specifically to NLK mediated bone marrow failure syndrome. Dominant negative mutations are readily generated for corresponding proteins. These may act by several different mechanisms, including mutations in a substrate-binding domain; mutations in a catalytic domain; mutations in a protein binding domain (e.g., multimer forming, effector, or activating protein binding domains); mutations in cellular localization domain, etc. A mutant polypeptide may interact with wild-type polypeptides (made from the other allele) and form a non-functional multimer. In certain embodiments, the mutant polypeptide will be overproduced. Point mutations are made that have such an effect. In addition, fusion of different polypeptides of various lengths to the terminus of a protein, or deletion of specific domains can yield dominant negative mutants. General strategies are available for making dominant negative mutants (see for example, Herskowitz, Nature (1987) 329:219, and the references cited above). Such techniques are used to create loss of function mutations, which are useful for determining protein function. Methods that are well known to those skilled in the art can be used to construct expression vectors containing coding sequences and appropriate transcriptional and translational control signals for increased expression of an exogenous gene introduced into a cell. These methods include, for example, in vitro recombinant DNA techniques, synthetic techniques, and in vivo genetic recombination. Alternatively, RNA capable of encoding gene product sequences may be chemically synthesized using, for example, synthesizers. See, for example, the techniques described in "Oligonucleotide Synthesis", 1984, Gait, M. J. ed., IRL Press, Oxford.

In some instances, the NLK expression inhibiting agent is a CRISPR-based gene silencing agent. By "CRISPR-based gene silencing agent" is meant one or more agents that when delivered to a cell cause the directed silencing of a target gene by CRISPER/Cas9-based nuclease activity. Accordingly, in some instances, a CRISPR-based gene silencing agent may include a guide RNA (gRNA) having sequence that specifically targets a Cas9 nuclease to a specific target gene, e.g., an NLK gene. CRISPR/Cas9-based silencing of a target gene may include delivery of a Cas9 polypeptide or a Cas9 polypeptide encoding nucleic acid to the subject cells. For example, in some instances, a vector that includes a nucleic acid that encodes a Cas9 nuclease may be delivered to the subject cells before, during or after the cell is contacted with a CRISPR-based gene silencing agent such that the encoded Cas9 nuclease is expressed when the CRISPR-based gene silencing agent is present within the cell. In some instances, the cell may be genetically modified with a nucleic acid encoding a Cas9 nuclease such that the encoded Cas9 nuclease is expressed (e.g., conditionally expressed, constitutively expressed, etc.) when the CRISPR-based gene silencing agent is present within the cell. Accordingly, CRISPR/Cas9-based silencing of the present methods may employ a Cas9 nuclease that is stably or transiently expressed including e.g., where a nucleic acid encoding the Cas9 nuclease is transiently or stably present within the cell line. In some instances, Cas9 polypeptide may be delivered to the subject cells, i.e., without the need to express the Cas9 polypeptide within the cells. CRISPR-based gene silencing agents will vary and may include e.g., vector (e.g., virus (e.g., lentivirus), plasmid, etc.) containing and/or expressing one or more gRNAs. Methods of delivery of CRISPR-based gene silencing agents will similarly vary any may include e.g., transfection, electroporation, lipofection, etc. CRISPR-based gene silencing agents of the present disclosure may be directed to essentially any element of a subject genome including e.g., protein-coding and non-protein coding elements of the subject genome. In some instances, e.g., where a plurality of CRISPR-based gene silencing agents is employed, the plurality of CRISPR-based gene silencing agents may collectively target all or essentially all genes of the subject genome (i.e., genome-wide targeting). In some instances, targeted non-protein coding elements may include but are not limited to e.g., promoters, enhancers, non-coding RNAs, and the like.

Specific NLK expression modulatory, e.g., inhibitory agents, that may be employed in embodiments of the methods further include, but are not limited to, miR-26a, miR-181, miR-208, miR-199, miR-101, miR-221 metformin, ginsenoside Rb1, ginseng and the like.

Administration of an agent to a subject, as described herein, may be performed employing various routes of administration. The route of administration may be selected according to a variety of factors including, but not necessarily limited to, the condition to be treated, the formulation and/or device used, the patient to be treated, and the like. Routes of administration useful in the disclosed methods include but are not limited to oral and parenteral routes, such as intravenous (iv), intraperitoneal (ip), rectal, topical, ophthalmic, nasal, and transdermal. Formulations for these dosage forms are described herein.

Where the agent is a polypeptide, polynucleotide, analog or mimetic thereof, it may be introduced into tissues or host cells by any number of routes, including viral infection, microinjection, or fusion of vesicles. Jet injection may also be used for intramuscular administration, as described by Furth et al., Anal Biochem. (1992) 205:365-368. The DNA may be coated onto gold microparticles, and delivered intradermally by a particle bombardment device, or "gene gun" as described in the literature (see, for example, Tang et al., Nature (1992) 356:152-154), where gold microprojectiles are coated with the DNA, then bombarded into skin cells. For nucleic acid therapeutic agents, a number of different delivery vehicles find use, including viral and non-viral vector systems, as are known in the art.

Those of skill in the art will readily appreciate that dose levels can vary as a function of the specific compound, the nature of the delivery vehicle, and the like. Preferred dosages for a given compound are readily determinable by those of skill in the art by a variety of means.

In those embodiments where an effective amount of an active agent is administered to the subject, the amount or dosage is effective when administered for a suitable period of time, such as one week or longer, including two weeks or longer, such as 3 weeks or longer, 4 weeks or longer, 8 weeks or longer, etc., so as to evidence a reduction in the disorder, e.g., a reduction in a symptom of the disorder or in a marker of disease pathology. For example, an effective dose is the dose that, when administered for a suitable period of time, such as at least about one week, and maybe about two weeks, or more, up to a period of about 3 weeks, 4 weeks, 8 weeks, or longer, will reduce a symptom of the disorder, for example, by about 10% or more, by about 20% or more, e.g., by 30% or more, by 40% or more, or by 50% or more, in some instances by 60% or more, by 70% or more, by 80% or more, or by 90% or more, for example, and will halt progression of the disorder in the subject. In some instances, an effective amount or dose of active agent will not only slow or halt the progression of the disease condition but will also induce the reversal of the condition, i.e., will cause an improvement in the neurological health of the subject. For example, in some instances, an effective amount is the amount that when administered for a suitable period of time, for example, at least about one week, and/or about two weeks, or more, up to a period of about 3 weeks, 4 weeks, 8 weeks, or longer will improve, stabilize, or at least reduce the progression of a disorder in subject, for example 1.5-fold, 2-fold, 3-fold, 4-fold, 5-fold, in some instances 6-fold, 7-fold, 8-fold, 9-fold, or 10-fold or more relative to the subject's condition prior to administration.

In some instances, in those embodiments where an effective amount of an active agent is administered to the subject, the amount or dosage is effective when administered for a suitable period of time to result in a desired erythroid expansion in the subject. In some instances, methods of the present disclosure may result in at least a 5%, e.g., at least a 10%, at least a 15%, at least a 20%, at least a 25%, at least a 30%, at least a 35%, at least a 40%, at least a 45%, at least a 50%, at least a 55%, at least a 60%, at least a 65%, at least a 70% at least a 75%, at least a 80%, e.g., erythroid expansion. Any convenient method of assessing erythroid expansion may be employed, such as those described in Valent et al., Haematologica. 2018 October; 103 (10): 1593-1603.

A "therapeutically effective amount", a "therapeutically effective dose" or "therapeutic dose" is an amount sufficient to effect desired clinical results (i.e., achieve therapeutic efficacy, achieve a desired therapeutic response, etc.). A therapeutically effective dose can be administered in one or more administrations. For purposes of this disclosure, a therapeutically effective dose of an agent is an amount that is sufficient, when administered to the individual, to palliate, ameliorate, stabilize, reverse, prevent, slow or delay the progression of the target disease state by, for example, inhibiting gene expression product formation, or otherwise preventing the symptoms or clinical progression of a neurodegenerative disorder present in the subject.

An effective amount of a subject compound will depend, at least, on the particular method of use, the subject being treated, the severity of the affliction, and the manner of administration of the therapeutic composition. A "therapeutically effective amount" of a composition is a quantity of a specified compound sufficient to achieve a desired effect in a subject (host) being treated.

Therapeutically effective doses of a subject compound or pharmaceutical composition can be determined by one of skill in the art, with a goal of achieving local (e.g., tissue) concentrations that are at least as high as the IC50 of an applicable compound disclosed herein.

The specific dose level and frequency of dosage for any particular subject may be varied and will depend upon a variety of factors, including the activity of the subject compound, the metabolic stability and length of action of that compound, the age, body weight, general health, sex and diet of the subject, mode and time of administration, rate of excretion, drug combination, and severity of the condition of the host undergoing therapy.

Conversion of an animal dose to human equivalent doses (HED) may, in some instances, be performed using the conversion table and/or algorithm provided by the U.S. Department of Health and Human Services, Food and Drug Administration, Center for Drug Evaluation and Research (CDER) in, e.g., *Guidance for Industry: Estimating the Maximum Safe Starting Dose in Initial Clinical Trials for Therapeutics in Adult Healthy Volunteers* (2005) Food and Drug Administration, 5600 Fishers Lane, Rockville, MD 20857; (available at www(dot)fda(dot)gov/cder/guidance/index(dot)htm, the disclosure of which is incorporated herein by reference).

| Species | To Convert Animal Dose in mg/kg to Dose in mg/m², Multiply by $k_m$ | To Convert Animal Dose in mg/kg to HED[a] in mg/kg, Either: | |
| --- | --- | --- | --- |
| | | Divide Animal Dose By | Multiply Animal Dose By |
| Human | 37 | — | — |
| Child (20 kg)[b] | 25 | — | — |
| Mouse | 3 | 12.3 | 0.08 |
| Hamster | 5 | 7.4 | 0.13 |
| Rat | 6 | 6.2 | 0.16 |
| Ferret | 7 | 5.3 | 0.19 |
| Guinea pig | 8 | 4.6 | 0.22 |
| Rabbit | 12 | 3.1 | 0.32 |
| Dog | 20 | 1.8 | 0.54 |
| Primates: | | | |
| Monkeys[c] | 12 | 3.1 | 0.32 |
| Marmoset | 6 | 6.2 | 0.16 |
| Squirrel monkey | 7 | 5.3 | 0.19 |
| Baboon | 20 | 1.8 | 0.54 |
| Micro-pig | 27 | 1.4 | 0.73 |
| Mini-pig | 35 | 1.1 | 0.95 |

[a]Assumes 60 kg human. For species not listed or for weights outside the standard ranges, HED can be calculated from the following formula:
HED = animal dose in mg/kg × (animal weight in kg/human weight in kg)0.33.
[b]This km value is provided for reference only since healthy children will rarely be volunteers for phase 1 trials.
[c]For example, cynomolgus, rhesus, and stumptail.

Pharmaceutical Compositions

A pharmaceutical composition comprising a subject compound (e.g., an NLK inhibitor) may be administered to a patient alone, or in combination with other supplementary active agents. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

A subject compound may be administered to the host using any convenient means capable of resulting in the desired reduction in disease condition or symptom. Thus, a subject compound can be incorporated into a variety of formulations for therapeutic administration. More particularly, a subject compound can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Formulations for pharmaceutical compositions are well known in the art. For example, Remington's Pharmaceutical Sciences, by E. W. Martin, Mack Publishing Co., Easton, Pa., 19th Edition, 1995, describes exemplary formulations (and components thereof) suitable for pharmaceutical delivery of disclosed compounds. Pharmaceutical compositions comprising at least one of the subject compounds can be formulated for use in human or veterinary medicine. Particular formulations of a disclosed pharmaceutical composition may depend, for example, on the mode of administration and/or on the location of the infection to be treated. In some embodiments, formulations include a pharmaceutically acceptable carrier in addition to at least one active ingredient, such as a subject compound. In other embodiments, other medicinal or pharmaceutical agents, for example, with similar, related or complementary effects on the affliction being treated can also be included as active ingredients in a pharmaceutical composition.

Pharmaceutically acceptable carriers useful for the disclosed methods and compositions are conventional in the art. The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances (e.g., excipients), such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin or plasma preparations.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The disclosed pharmaceutical compositions may be formulated as a pharmaceutically acceptable salt of a disclosed compound. Pharmaceutically acceptable salts are non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydroiodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicylic acid, formic acid, trichloroacetic acid, trifluoroacetic acid, gluconic acid, asparagic acid, aspartic acid, benzenesulfonic acid, p-toluenesulfonic acid, naphthalenesulfonic acid, and the like. Lists of other suitable pharmaceutically acceptable salts are found in Remington's Pharmaceutical Sciences, 17th Edition, Mack Publishing Company, Easton, Pa., 1985. A pharmaceutically acceptable salt may also serve to adjust the osmotic pressure of the composition.

A subject compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A subject compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The preparation may also be emulsified or the active ingredient encapsulated in liposome vehicles. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

In some embodiments, a subject compound can be delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

A subject compound can be utilized in aerosol formulation to be administered via inhalation. A subject compound can be formulated into pressurized acceptable propellants such as dichlorodifluoromethane, propane, nitrogen and the like.

Furthermore, a subject compound can be made into suppositories by mixing with a variety of bases such as emulsifying bases or water-soluble bases. A subject compound can be administered rectally via a suppository. The suppository can include vehicles such as cocoa butter, carbowaxes and polyethylene glycols, which melt at body temperature, yet are solidified at room temperature.

The term "unit dosage form," as used herein, refers to physically discrete units suitable as unitary dosages for human and animal subjects, each unit containing a predetermined quantity of a subject compound calculated in an amount sufficient to produce the desired effect in association with a pharmaceutically acceptable diluent, carrier or vehicle. The specifications for a subject compound depend on the particular compound employed and the effect to be achieved, and the pharmacodynamics associated with each compound in the host.

The dosage form of a disclosed pharmaceutical composition will be determined by the mode of administration chosen. For example, in addition to injectable fluids, topical or oral dosage forms may be employed. Topical preparations may include eye drops, ointments, sprays and the like. In some instances, a topical preparation of a medicament useful in the methods described herein may include, e.g., an ointment preparation that includes one or more excipients including, e.g., mineral oil, paraffin, propylene carbonate, white petrolatum, white wax and the like, in addition to one or more additional active agents.

Oral formulations may be liquid (e.g., syrups, solutions or suspensions), or solid (e.g., powders, pills, tablets, or capsules). Methods of preparing such dosage forms are known, or will be apparent, to those skilled in the art.

Certain embodiments of the pharmaceutical compositions comprising a subject compound may be formulated in unit dosage form suitable for individual administration of precise dosages. The amount of active ingredient administered will depend on the subject being treated, the severity of the affliction, and the manner of administration, and is known to those skilled in the art. Within these bounds, the formulation to be administered will contain a quantity of the extracts or compounds disclosed herein in an amount effective to achieve the desired effect in the subject being treated.

Each therapeutic compound can independently be in any dosage form, such as those described herein, and can also be administered in various ways, as described herein. For example, the compounds may be formulated together, in a single dosage unit (that is, combined together in one form such as capsule, tablet, powder, or liquid, etc.) as a combination product. Alternatively, when not formulated together in a single dosage unit, an individual subject compound may be administered at the same time as another therapeutic compound or sequentially, in any order thereof.

In some instances, methods of treating a subject as described herein may include administering to the subject an effective amount of an agent that reduces RGC degeneration in the subject, as identified in a method of screening described herein.

Combination Therapies

The NLK inhibitors disclosed herein can be administered to a subject alone or in combination with an additional, i.e., second, active agent. Combination therapeutic methods where the NLK inhibitors may be used in combination with a second active agent or an additional therapy. The terms "agent," "compound," and "drug" are used interchangeably herein. For example, NLK inhibitors can be administered alone or in conjunction with one or more other drugs, such as drugs employed in the treatment of bone marrow failure syndromes, including but not limited to DBA. In some embodiments, the subject method further includes co-administering concomitantly or in sequence a second agent, e.g., a small molecule, an antibody, an antibody fragment, etc. For example, combination therapy may include administration of an NLK inhibitor in combination with another bone marrow failure therapy, e.g., another DBA therapy, such as corticosteroids, blood transfusions, a bone marrow transplant or stem cell transplantation.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

"Concomitant administration" of a known therapeutic drug or additional therapy with a pharmaceutical composition of the present disclosure means administration of the compound and second agent or additional therapy at such time that both the known drug and the composition of the present invention will have a therapeutic effect. Such concomitant administration may involve concurrent (i.e. at the same time), prior, or subsequent administration of the drug with respect to the administration of a subject compound. Routes of administration of the two agents may vary, where representative routes of administration are described in greater detail below. A person of ordinary skill in the art would have no difficulty determining the appropriate timing, sequence and dosages of administration for particular drugs or therapies and compounds of the present disclosure.

In some embodiments, the compounds (e.g., an NLK inhibitor and the at least one additional compound (e.g., corticosteroid) or therapy) are administered to the subject within twenty-four hours of each other, such as within 12 hours of each other, within 6 hours of each other, within 3 hours of each other, or within 1 hour of each other. In certain embodiments, the compounds are administered within 1 hour of each other. In certain embodiments, the compounds are administered substantially simultaneously. By administered substantially simultaneously is meant that the compounds are administered to the subject within about 10 minutes or less of each other, such as 5 minutes or less, or 1 minute or less of each other.

Also provided are pharmaceutical preparations of the NLK inhibitor and the second active agent. In pharmaceutical dosage forms, the compounds may be administered in the form of their pharmaceutically acceptable salts, or they may also be used alone or in appropriate association, as well as in combination, with other pharmaceutically active compounds.

Reagents, Devices and Kits

Also provided are reagents, devices and kits thereof for practicing one or more of the above-described methods. The subject reagents, devices and kits thereof may vary greatly. The kits may include, e.g., one or more unit dosages of NLK inhibitors, e.g., as described above. Any convenient NLK inhibitor may be present in such unit dosages. Optionally, the kits may include one or more additional bone marrow failure syndrome, e.g., DBA, therapies, such as those described above.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, portable flash drive, etc., on which the information has been recorded. Yet another means that may be present is a website address which may be used via the internet to access the information at a removed site. Any convenient means may be present in the kits.

The following example(s) is/are offered by way of illustration and not by way of limitation.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, cells, and kits for methods referred to in, or related to, this disclosure are available from commercial vendors such as BioRad, Agilent Technologies, Thermo Fisher Scientific, Sigma-Aldrich, New England Biolabs (NEB), Takara Bio USA, Inc., and the like, as well as repositories such as e.g., Addgene, Inc., American Type Culture Collection (ATCC), and the like.

1. Diamond Blackfan Anemia is Mediated by Hyperactive Nemo-Like Kinase

A. Abstract

Ribosomal insufficiency in hematopoietic stem and progenitor cells results in bone marrow failure syndromes, such as Diamond Blackfan Anemia (DBA). We report that Nemo-Like Kinase (NLK) is specifically hyperactivated in erythroid progenitors from murine and human models of DBA, and in patient samples. In addition, inhibition of NLK activity, either genetically or pharmacologically, improves erythroid expansion without affecting other hematopoietic lineages. Hyperactivated NLK directly phosphorylates c-Myb and Raptor in erythroid progenitors, contributing to a block in red blood cell differentiation. Phosphorylation by NLK results in ubiquitination-mediated degradation of c-Myb and a decreased recruitment of mTOR to lysosomes, decreased mTOR activity and increased mTOR-suppressed autophagy. We identified small molecules that promote erythropoiesis in ribosome-insufficient hematopoietic progenitor cells and inhibit NLK activity. Pharmacological inhibition of NLK increases erythroid expansion in murine and human models of DBA as well as in bone marrow stem and progenitor cells from DBA patients. These results demonstrate that hyperactive NLK mediates aberrant erythropoiesis in DBA and is a target for therapy.

B. Introduction

Diamond Blackfan Anemia (DBA) is a congenital bone marrow failure syndrome usually diagnosed within the first year of life[1]. Approximately 70% of DBA patients possess a mutation in one of 19 genes that encode ribosomal proteins, with mutations in Ribosomal Protein S19 (RPS19) accounting for over 25% and RPL11 comprising approximately 5% of cases. Complete loss of ribosomal components is not viable, while mutations resulting in haploinsufficiency cause erythropoiesis failure due to a block in differentiation of early erythroid progenitors[2]. Erythroid specificity of ribosomal insufficiency in DBA is largely due to reduced translational efficiency of genes possessing a short, complex 5'UTR that is highly upregulated, particularly GATA1[3]. However, GATA1 restoration only partially rescues the DBA phenotype[4].

The master erythroid transcription factor c-Myb is highly expressed in hematopoietic stem cells and early progenitors and is highly elevated in early erythropoiesis. Myb is rapidly downregulated in progenitors from both cord and peripheral blood[5,6]. Myb serves a number of cellular roles in erythropoiesis, including transcriptional regulation of the master regulators KLF1 and LMO2[7,8]. Additionally, downregulation of c-Myb has been reported in RPS19-insufficiency[9].

Autophagy involves the wholesale depletion of membrane organelles and extrusion of the nucleus during normal late erythropoiesis and expression profiling indicates sharp upregulation of numerous autophagy-regulating genes including all ATG8 family members and a subset of ATG4 genes[10]. Premature autophagy and increased autophagosomes have been observed in DBA[11] but it remains unclear if, or when, autophagy serves to aid or antagonize healthy erythroid progenitor cells. Indeed pharmacological stimulation of autophagy in an iPS model of DBA facilitates increased erythroblast production[12].

Nemo-like kinase (NLK) is an evolutionarily conserved serine/threonine kinase. It belongs to the proline directed protein kinase superfamily, which consists of mitogen activated protein kinases (MAPKs) and cyclin-dependent protein kinases (CDKs)[13,14]. NLK contributes to cell proliferation, differentiation, apoptosis and morphological changes during early embryogenesis and nervous system development and is involved in the pathogenesis of several human cancers[14,15]. Overexpression of NLK in colorectal, laryngeal, and non-small cell lung cancer, as well as osteosarcomas and neuroblastomas correlate with poor prognosis and more aggressive tumors.

NLK regulates a diverse array of signaling pathways, including the Wnt/β-catenin, Activin, IL-6, and Notch signaling pathways[14]. In Wnt-1-stimulated HEK293T cells, NLK phosphorylates c-Myb, priming it for ubiquitination by the E3-ubiquitin kinase Fbxw7 and subsequent proteasome degradation[16-18]. Raptor is another reported substrate of NLK[19]. In a kinome library screen designed to identify mTOR inhibitors during oxidative and hyperosmotic stress, NLK activation was detected. Subsequent phosphorylation of raptor at S863 prevented mTOR-associated raptor from localizing to the lysosomal membrane for activation[19]. Additional NLK substrates regulated by NLK phosphorylation include ATF5[20], FoxO1[21], Lef1[22] and HDAC[23].

NLK is not ubiquitously expressed and several reports show NLK expression is regulated by microRNAs (miRNAs). Yan et al[24] reported miR208 was upregulated in response to the active ingredient of *ginseng*. Upregulated miR208 bound the 3'UTR of NLK, leading to reduced protein expression. During natural killer (NK) differentiation, miR181 was reported to bind and downregulate NLK expression. Loss of NLK was critical for efficient NK production by increasing the expression of the Notch target Hes5[25]. Hepatic cancer stem cells were found to have elevated miR181 levels and low NLK expression. Inhibition of miR181 resulted in markedly increased levels of NLK[26]. Family members of miR181 may control NLK expression in a variety of tissues[14].

Here we report that Nemo-like Kinase (NLK) is chronically hyper-activated during erythroid differentiation in human and murine DBA models, including human bone marrow and iPSCs from DBA patients. We found that erythroblast specificity of NLK activation is due to upregulation of miR181 in other hematopoietic lineages. Blocking NLK activation, using small inhibitory RNA or pharmacological agents rescues c-Myb and Raptor functions and significantly restores erythrocyte maturation of RPS19-insufficient progenitors. In addition, we characterized a subset of TGFβR1 inhibitory compounds with off-target inhibition of NLK. Treatment with these compounds increased the number of RPS19-insufficient erythroid progenitor cells. Our results demonstrate that NLK is critical to the pathogenesis of DBA and is a target for therapy.

C. Results

1. NLK In Vitro Kinase Assay Recapitulates Intracellular NLK Activity

To examine NLK activity in small numbers of cells, we developed an ultrasensitive ELISA-based in vitro kinase assay. Immuno-purified NLK from cells of interest was incubated in the presence of immobilized, dephosphorylated potential substrates in the presence of ATP and $MgCl_2$. We utilized three endogenous NLK substrates in parallel (NLK itself, c-Myb and raptor) increasing our confidence that phosphorylation was due to NLK activity and not another kinase that co-precipitated with the NLK antibody. Introducing siRNA against NLK in cells prior to immune-precipitation reduced in vitro phosphorylation to baseline, further validating the NLK specificity of the assay. Western blot analysis demonstrated that immuno-precipitated NLK, c-Myb and raptor were phosphorylated at serine/threonine residues. While c-Myb is phosphorylated at several serine residues by NLK[27], autophosphorylation of NLK occurs at T298[28] while raptor is phosphorylated at S863[19]. Intracellular phosphorylation of these residues was detected using phospho-specific antibodies that correlated with NLK in vitro kinase activity. Phosphorylation of raptor at S792 (phosphorylated by active AMPK[29]) or ERK was not modulated and phosphorylation of c-Myc was not observed by in vitro kinase assays or intracellularly.

2. NLK Activation Occurs in Erythroid Progenitors and Human and Murine Models of DBA Bone marrow mononuclear cells from healthy controls or three DBA patients carrying different RPS19 mutations, were analyzed for NLK activity. Following normalization to the same number of healthy control cells, mononuclear cells from DBA patient bone marrow aspirates showed a significant increase in phosphorylation of all three substrates (2.2, 2.0 and 2.2-fold NLK phosphorylation, 3.3, 2.4 and 2.6-fold c-Myb phosphorylation, and 4.8, 4.1 and 4.2-fold raptor phosphorylation). Despite increased NLK activity, reduced NLK expression was observed in bone marrow mononuclear cells from DBA patient samples (0.4, 0.6 and 0.5-fold of healthy control). As expected, RPS19 expression was significantly lower in bone marrow cells from DBA patients (0.6, 0.8 and 0.6-fold) compared to control cells (FIG. 1, panel a).

The transduction of shRNA against ribosomal genes is an accepted model for examining the effects of ribosomal insufficiency during erythropoiesis[30-32]. Knockdown efficiency of these shRNAs is partial, recapitulating the haploinsufficiency of the disease state. RPS19 and RPL11 are two of the most commonly mutated genes in DBA[1]. Thus, CD34+ cells isolated from cord blood were transduced with lentivirus expressing GFP and RPS19, RPL11 or luciferase control shRNA. The specific shRNA sequence was selected for approximately 50% knockdown efficiency (FIG. 1, panel b—lower portions[30]). After 30-48 hours, cells were sorted for GFP expression and plated in media promoting erythroid differentiation for 10 days. Each day, cells were collected and assayed for NLK activity and expression of NLK, RPS19 and RPL11. We observed a mild increase in in vitro phosphorylation of all three substrates at day 3 compared to control cells. These results indicate a transient activation of NLK in control hematopoietic stem and progenitor cells (HSPC) during early differentiation. In contrast, a dramatic and sustained increase in NLK activity was induced in RPS19-insufficient cells with NLK phosphorylation exceeding controls by 4-fold, Myb phosphorylation exceeding by 6-fold, and raptor phosphorylation by 9-fold. Similarly, RPL11-insufficiency induction paralleled RPS19-insufficiency but was less robust (FIG. 1, panel b).

RPS19 and RPL11 are relatively stable proteins and significant reduction does not occur until 4 to 5 days after shRNA transduction (FIG. 1, panel b). CD34+ hematopoietic stem and progenitor cells (HPSCs) generated from induced-pluripotent stem cells (iPSCs) can be differentiated into all hematopoietic lineages[33] and can be generated from DBA patient bone marrow cells[12]. We generated iPSC clones from a healthy control, transduced a tetracycline-inducible shRNA against RPS19 and HSCs were differentiated in the presence or absence of doxycycline (Dox). In the presence of doxycycline, CD34+clonal HSC colonies expressed reduced RPS19 expression, however NLK activity showed no difference from cells cultured in the absence of doxycycline. Not until after 4 days of differentiation in erythroid media, was a sustained, significant increase in NLK activation initiated in RPS19-insufficient cultures, indicating NLK activation occurs in early progenitors and not in CD34+ HSPCs.

iPSCs were generated from a patient heterozygous in the RPS26 gene (p.C74Y) and a patient with an unknown genetic mutation with typical clinical features of DBA. iPSC clones carrying the RPS26 mutation were transduced with a tetracycline-inducible wild-type RPS26. In the absence of doxycycline, robust NLK activation was observed, whereas NLK activity was significantly reduced upon expression of wild-type RPS26. All three clones generated from a patient with unknown genetic background displayed elevated NLK activity during erythroid differentiation compared to healthy control iPSCs.

Subtle differences in erythroid development have been reported between various sources of CD34+ progenitors[5]. We observed low basal NLK activity in differentiating progenitors derived from healthy control cord blood, fetal liver and peripheral blood, with significant upregulation of NLK activity in all three progenitor sources during RPS19-insufficiency.

Despite differences in human and murine erythroid regulation[34], a DBA-like phenotype develops in mice with either RPS19 or RPL11 insufficiency[35,36]. Expansion of hematopoietic progenitor Lin-Kit+ fetal (E14.5) liver cells expressing a tetracycline-inducible shRNA against RPS19 into Ter119+ erythroblasts is significantly reduced when differentiated in doxycycline[35]. Lin⁻Kit+ cells from three tet-shRPS19 mice were cultured in the absence or presence of doxycycline. Compared to untreated cells, increased NLK activity (NLK: 1.9-fold, c-Myb: 3.2-fold, raptor: 5.3-fold) was observed in doxycycline-treated cells.

Similarly, mice expressing a single copy of the RPL11 allele develop anemia[36]. Mice heterozygous for RPL11$^{flox}$ were grown to adulthood before treatment with tamoxifen for 8 weeks to knockout one allele of RPS11. Lin-Kit+ hematopoietic progenitors were isolated and assessed for NLK activity. NLK activity was increased in all three RPL11-haploinsufficient mice (NLK: 2.1-fold, c-Myb: 4.1-fold, raptor: 7.2-fold) compared to tamoxifen-treated wild type mice (FIG. 1, panel c—right portions). Collectively, these data indicate that NLK is activated during ribosomal gene insufficiency in bone marrow aspirates from DBA patients along with human and murine models of the disease.

3. NLK Activation is Dependent on p53

Ribosomal-insufficiency results in p53 stabilization that is critical in mediating the pathogenic effects of DBA[1,37]. To determine if NLK activation requires p53, we transduced shRNA against p53 in control and RPS19-insufficient CB CD34+ progenitors. After 5 days of differentiation, both RPS19 and p53 (FIG. 1, panel d—lower portions) levels were appropriately modulated by shRNA transduction. NLK activity was robustly induced in RPS19-insufficient cultures, however suppression of p53 reduced NLK activity close to baseline levels (FIG. 1, panel d—upper portions), indicating p53 expression is critical for NLK activation during RPS19-insufficiency.

Figure 2:
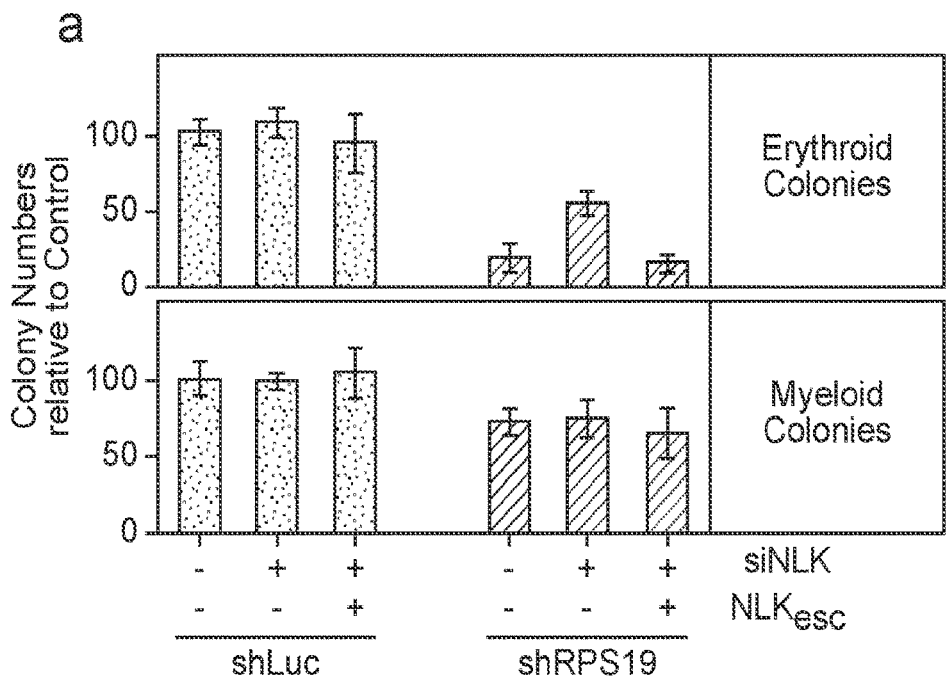
FIG. 2. The 3'-UTR of NLK contributes to aberrant erythropoiesis in RPS19-insufficiency, but not non-erythroid progenitors. (a) Cord blood CD34+ progenitors were transduced with lentivirus expressing shRNA against luciferase (shLuc) or RPS19 (shRPS19) co-expressing GFP, along with siRNA targeting NLK (siNLK) co-expressing RFP and a siNLK-resistant NLK (NLK$_{esc}$) co-expressing puromycin resistance. GFP+RFP+ progenitors were differentiated in methylcellulose for 12-15 days and colonies were scored as either erythroid (upper panel) or myeloid (lower panel). (b) Transduced GFP+, RFP+cord blood CD34+ progenitors were differentiated in erythroid media for 15 days prior to counting and assessment for surface expression of CD235 (erythroid), CD41a (megakaryocyte) and CD11b (myeloid) cellular markers by flow cytometry. After multiplying percentage of cells expressing each differentiation marker by the total number of cells of each culture prior to sorting, values were normalized and expressed as a percentage of control (shLuc/NT) for each lineage. (c) At day 5 during differentiation, 5000 cells from each population were collected and subjected to qRT-PCR and NLK kinase assay to determine NLK expression (upper panel) and NLK activity (lower panel) respectively. (d) After FACs sorting, CD235+, CD41a+ and CD11b+ cells from control (shLuc) or RPS19-insufficient (shRPS19) cultures, 5000 cells were lysed and scrutinized for the ability of immuno-purified NLK to phosphorylate unphosphorylated NLK (upper panel), and assessed for NLK expression by qRT-PCR (lower panel). (E) CD34+ progenitors were transduced with shRNA against a non-targeting sequence, (NT) or RPS19 (shRPS19) and the NLK minimal promoter upstream of the luciferase gene (upper panel) or luciferase gene with the NLK 3'UTR downstream (lower panel). After 12 days of differentiation in erythroid media, cultures were sorted by flow cytometry into designated hematopoietic lineages (CD235+: black, CD41a+: dark grey, CD11b+: light grey), and luciferase activity was assessed.
Figure 2:
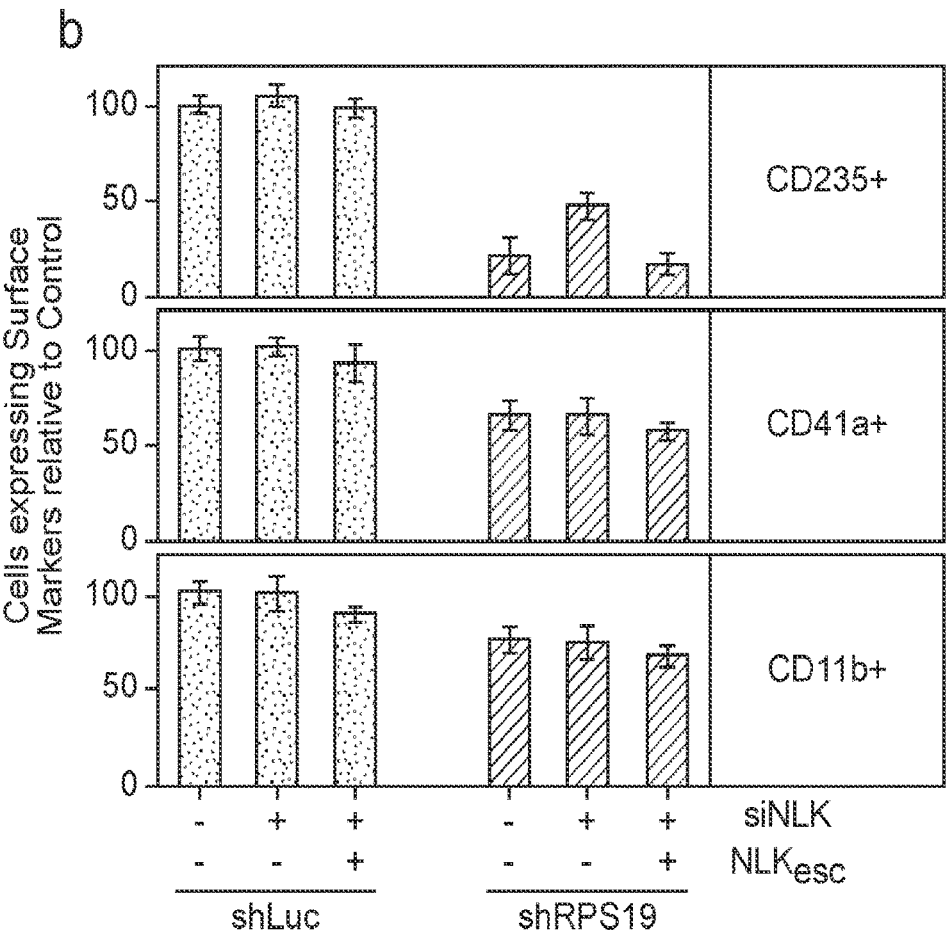
Figure 2:
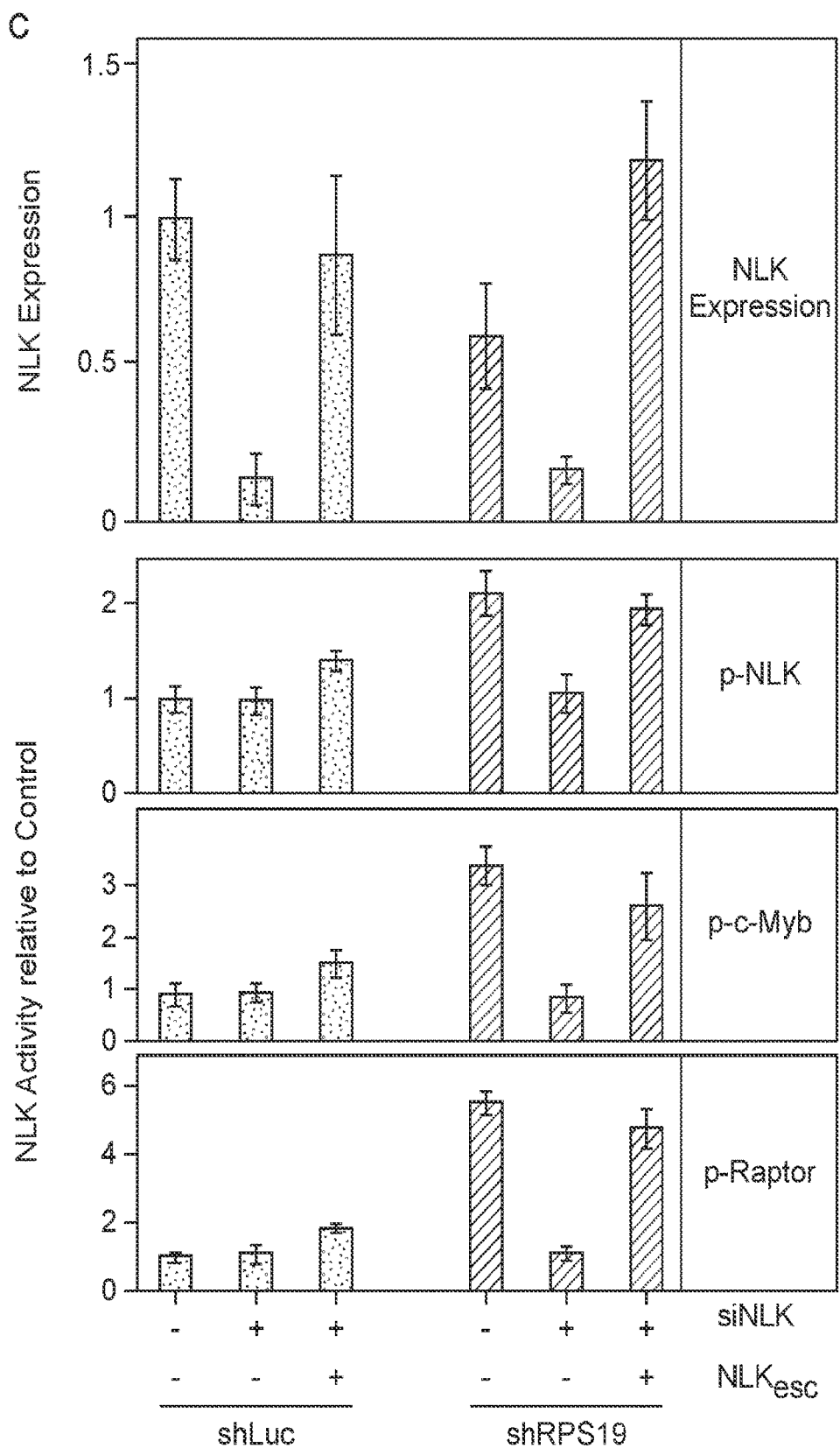
Figure 2:
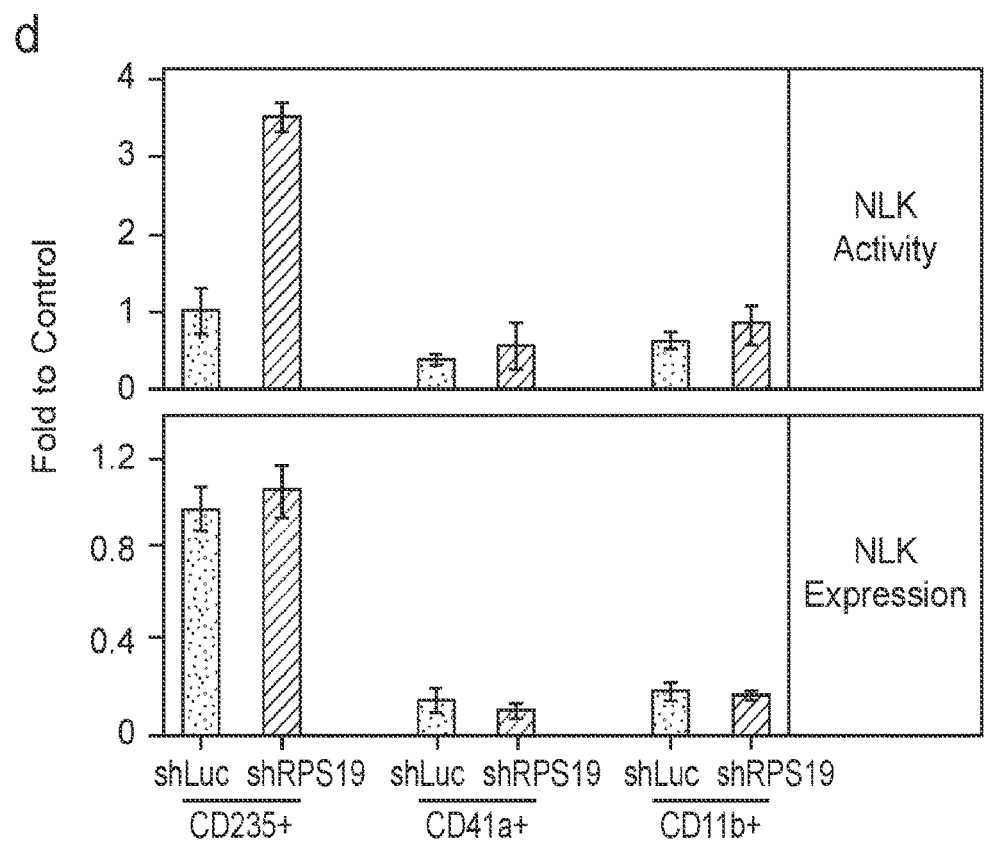
Figure 2:
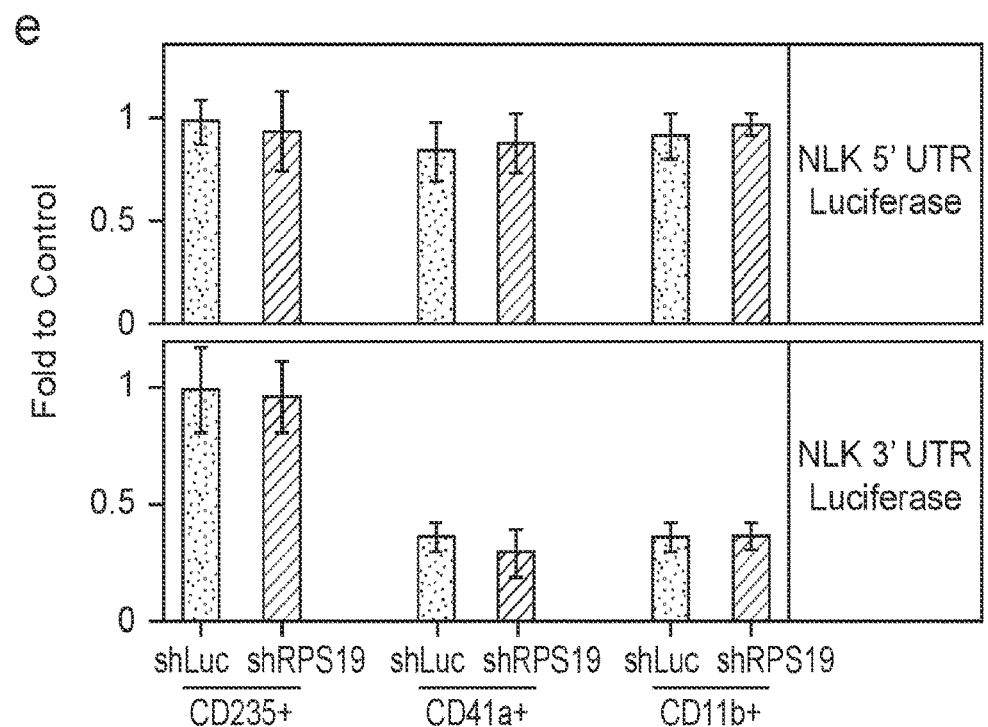

4. Silencing NLK Expression Increases Erythroid Expansion in RPS19-Insufficiency in Human Hematopoietic Progenitors Having determined that NLK is activated in response to ribosomal insufficiency, we sought to examine whether NLK plays a role in the failure of RPS19-insufficient erythroid progenitors to adequately differentiate and proliferate. Human CB CD34+ HSPCs were transduced with combinations of lentivirus expressing shRNA against RPS19 or luciferase (also co-expressing GFP), siRNA against NLK or a non-targeting sequence (also co-expressing RFP), and NLK cDNA resistant to siNLK or a non-targeting sequence (co-expressing puromycin resistance). After sorting, cells were split into two pools; one grown in erythroid-promoting conditions supporting colony growth (FIG. 2, panel a) and the other in liquid culture (FIG. 2, panel b).

As each colony develops from a single, viable progenitor, colonies assays indicate the abundance and ratio of erythroid (BFU-E) and non-erythroid myeloid (CFU-GM) progenitors during early differentiation. The expression of shRPS19 (FIG. 2, panel a—upper portion, black bars) decreased erythroid (BFU-E) colony formation to 18.8% of control (FIG. 2, panel a—upper portion, white bars) and a milder reduction in myeloid (CFU-GM) colonies to 72.4% of control (FIG. 2, panel a lower portion). This parallels the disease condition whereby ribosome-insufficiency primarily targets erythropoiesis.

Modulation of NLK had no impact on erythroid colony formation in shLuc controls. Suppression of NLK by siRNA insignificantly increased colonies to 105.5% of control, while re-introduction of siRNA-resistant NLK yielded 92.4% of control (FIG. 2, panel a upper portion white bars). In contrast, in RPS19-insufficiency, HPCs expressing siRNA against NLK initiated improved erythroid colony formation from 18.8% to 53.6% of control, while re-introduction of NLK returned BFU-E colony formation to 15.3% (FIG. 2, panel a upper portion black bars). Colonies derived from RPS19-insufficient HPCs tended to be smaller in diameter than controls and the silencing of NLK did not dramatically rescue this effect (data not shown). While RPS19 reduced myeloid colonies to 72.4% of control, NLK expression had a negligible impact on the myeloid colony numbers in control and RPS19-insufficient cultures (FIG. 2, panel a lower portion—black bars).

Similar observations were recorded in liquid culture. RPS19-insufficiency reduced maturing CD235+ erythroblast expansion to 21.2% of controls (FIG. 2, panel b—upper portion), but only reduced CD41a+ megakaryocyte expansion to 65.3% of controls (FIG. 2, panel b—middle portion) and CD11b+ myeloid expansion to 74.9% of controls (FIG. 2, panel b—lower portion). As seen in colony assays, silencing of NLK had a negligible impact on RPS19-insufficient megakaryocyte and myeloid cells but increased the expansion of maturing erythroblasts from 21.2% to 46.7% of controls and NLK re-introduction reducing it back to 16.3% (FIG. 2, panel b). As anticipated, NLK activity was modulated parallel to NLK expression in conditions that promoted activation (FIG. 2, panel c).

5. NLK Effects are Limited to Erythroid Progenitors Because NLK Expression is Downregulated in Non-Erythroid Hematopoietic Progenitors by miR181

We demonstrated that NLK is activated in differentiating progenitors during erythropoiesis in ribosomal insufficiency (FIG. 1), and that NLK activity contributes to erythroid failure while not impacting megakaryocyte and other myeloid cell differentiation (FIG. 2, panels a and b). Therefore, we sought to understand the mechanisms by which only erythroid progenitors are influenced by NLK activation. RPS19-insufficient CB CD34+ progenitors differentiated in myeloid- or megakaryocyte-promoting conditions demonstrated significantly less NLK activation and a greater reduction in NLK expression than cultures differentiated in erythroid-promoting conditions (FIG. 1, panel B—left portions). This prompted us to examine if NLK activation was not uniform across hematopoietic lineages. After 12 days of differentiation in erythroid media, control (shLuc) and RPS19-insufficient (shRPS19) cells were FACs sorted into maturing erythroid (CD235+), megakaryocyte (CD41a+), or myeloid (CD11b+) cells and assessed for NLK activity (FIG. 2, panel D—upper portion) and NLK expression (FIG. 2, panel D—lower portion). In control cells transduced with only shLuc, basal NLK activity in CD41+ and CD11b+ samples was only 38% and 61% of CD235+ erythroid levels respectively. In RPS19-insufficiency, NLK activation was markedly increased 3.4-fold in CD235+ erythroblasts but did not increase significantly in megakaryocytes or other myeloid cells (FIG. 2, panel d—upper portions).

Examination of NLK expression demonstrated CD41+ megakaryocytes and CD11b+myeloid cells express only 16% and 20% of the amount of NLK expressed in erythroid cells, however, this was not influenced by RPS19-insufficiency (FIG. 2, panel D—lower portion).

To determine if the disparities in NLK expression were due to influences on the NLK promoter or 3'UTR, we utilized luciferase expressing lentiviral constructs with either the minimal NLK promoter cloned 5' to luciferase, or the NLK 3'UTR cloned 3' to luciferase. The expression of NLK promoter-driven luciferase was not significantly altered between erythroid, megakaryocyte or myeloid cells or by RPS19-insufficiency (FIG. 2E—upper panel). In contrast, luciferase activity was reduced by 73.4% in megakaryocytes and myeloid cells when fused with the NLK 3'UTR (FIG. 2E—lower panel). RPS19-insufficiency had no impact on luciferase-NLK 3'UTR fusion expression (FIG. 2, panel e—lower portion) in any lineage, suggesting erythroid-specific expression of NLK occurs during normal hematopoiesis, while the activation of the available NLK occurs only during RPS19-insufficiency.

The regulation of NLK by miRNA binding to the 3'UTR has been reported previously[24,25]. Yan et al[24] reported miR208 was upregulated in response to the active ingredient of ginseng. Upregulated miR208 bound the 3'UTR of NLK, leading to reduced protein expression. During NK differentiation, miR181 binds to and downregulates NLK expression. Loss of NLK is critical for efficient NK production by increasing the expression of the Notch target Hes5[25] It has been reported that megakaryocytic differentiation critically requires the upregulation of miR181[38]. The inhibition or addition of miR181 influences the erythroid versus megakaryocytic ratio during differentiation[38]. The differentiation of other myeloid and lymphoid lineages is also critically regulated by miR181 and is often downregulated in leukemia[39-41].

Based on these reports, we hypothesized that miR181 induction in non-erythroid progenitors target the 3'UTR of NLK transcripts, leading to a reduction of NLK protein in these cells. Should our hypothesis be correct, uncoupling miR181 from NLK expression would lead to elevated NLK expression in non-erythroid cells, leaving them susceptible to the effects of NLK activation during RPS19-insufficiency. Since miR181 directly influences differentiation independently of NLK, this hypothesis was tested two ways; by expressing recombinant NLK transcripts with modified 3'UTRs, and by mutating the endogenous miR181 binding site within the 3'UTR using CRISPR/Cas9.

Figure 3:
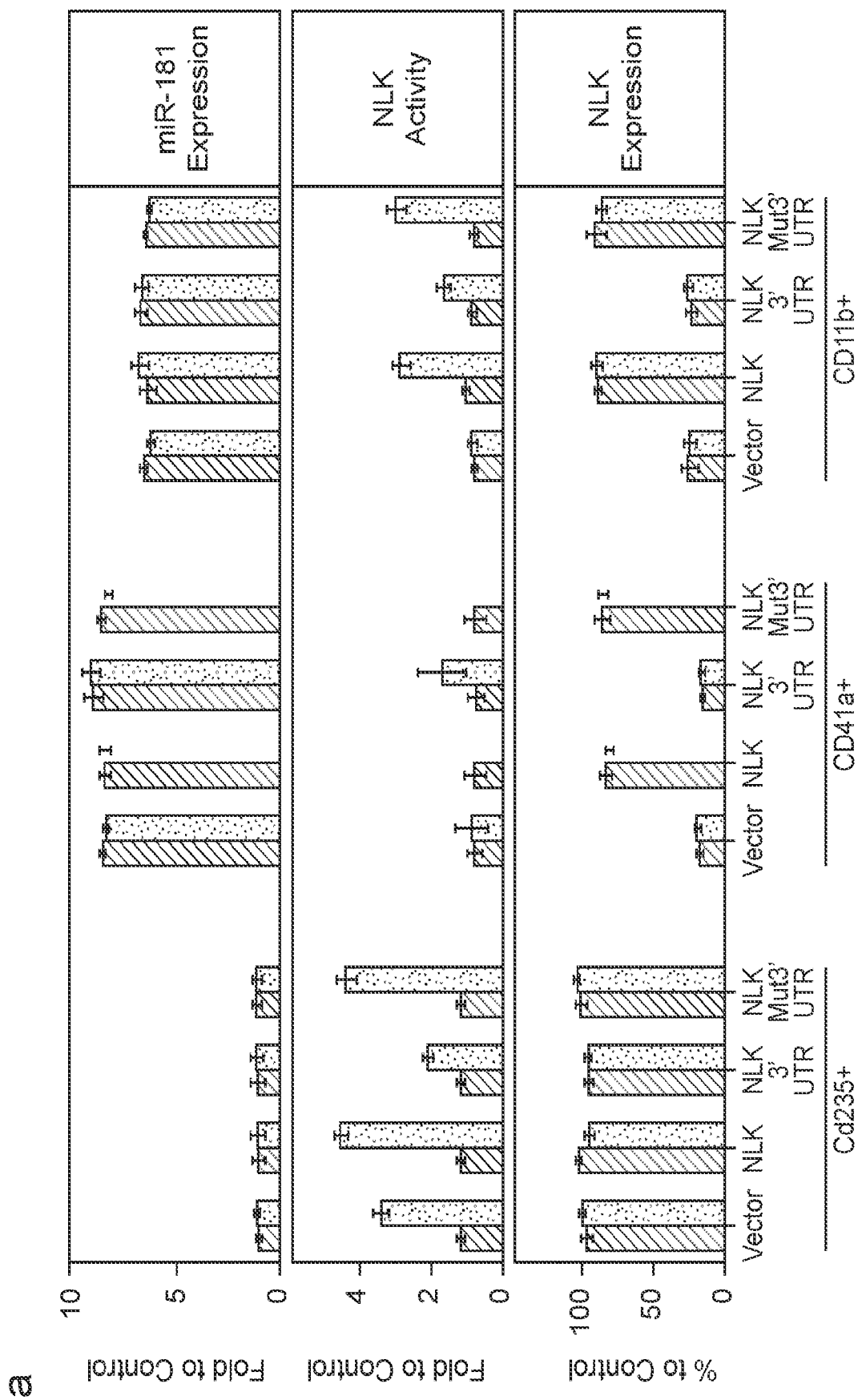
FIG. 3. Upregulation of miR181 suppresses NLK expression in non-erythroid progenitors and protects cells from RPS19-insufficiency. (a) CD34+ progenitors were transduced with shluc (white bars) or shRPS19 (dark bars), in addition to vectors expressing cDNA for NLK behind a hEF1α promoter with either a 3'UTR with 3 stop sequences (NLK stop), the wild type NLK 3'UTR (NLK WT 3'UTR) or 3'UTR with the miR181 binding site mutated (NLK Mut 3'UTR). After differentiation, cells were sorted into hematopoietic lineage and assessed for miR181 expression, (top panel), NLK activity (middle), and NLK expression (bottom) by qRT-PCR and kinase assay. (b) The relative number of each hematopoietic lineage was determined as a percentage of the number observed in controls expressing only endogenous NLK. (c) CD34+ progenitors were electroporated with Cas9 and 1 of 3 gRNAs. The first generated indels within the miR181 binding site of the NLK 3'UTR (d181), the second generated indels just downstream of miR181 binding site (off target), and the third generated indels within the RelA gene (Rel A). After 24 h recovery, cultures were transduced with shLuc or shRPS19 and differentiated for 15 days. After counting and sorting for lineage (grey bars), cells were sequenced to determine the percentage of cells within each population, carrying indels in miR181 binding site (blue) and RelA (red) (c—upper). The percentage of cells carrying indels in NLK 3'UTR miR181 binding site (blue) and RelA (red) in each treatment were further compared for impact on population expansion between lineages (c—lower). This was achieved by determining the number of mutation-baring cells in each cell population and expressing that as a percentage of the number observed without Cas9-generated indels (control).
Figure 3:
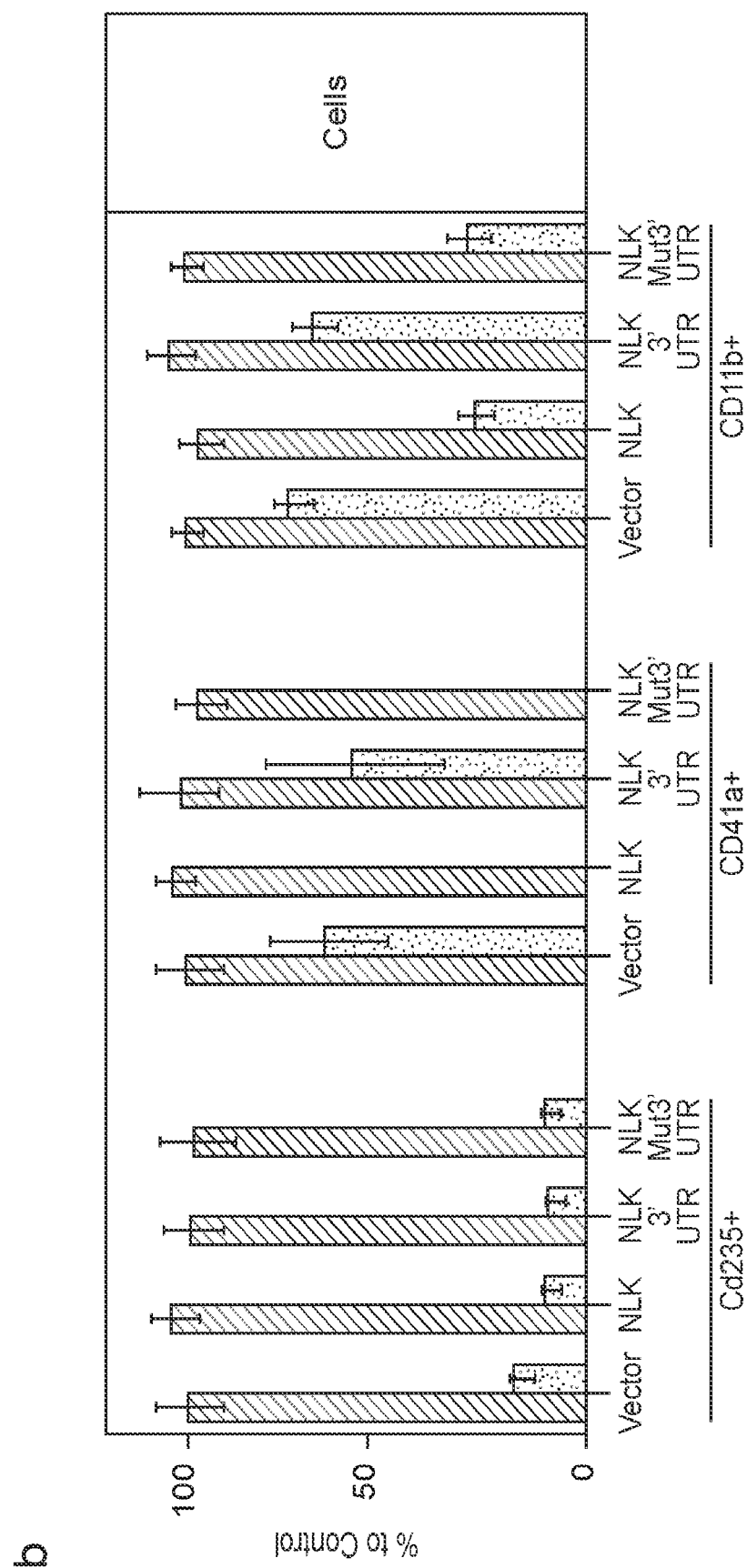
Figure 3:
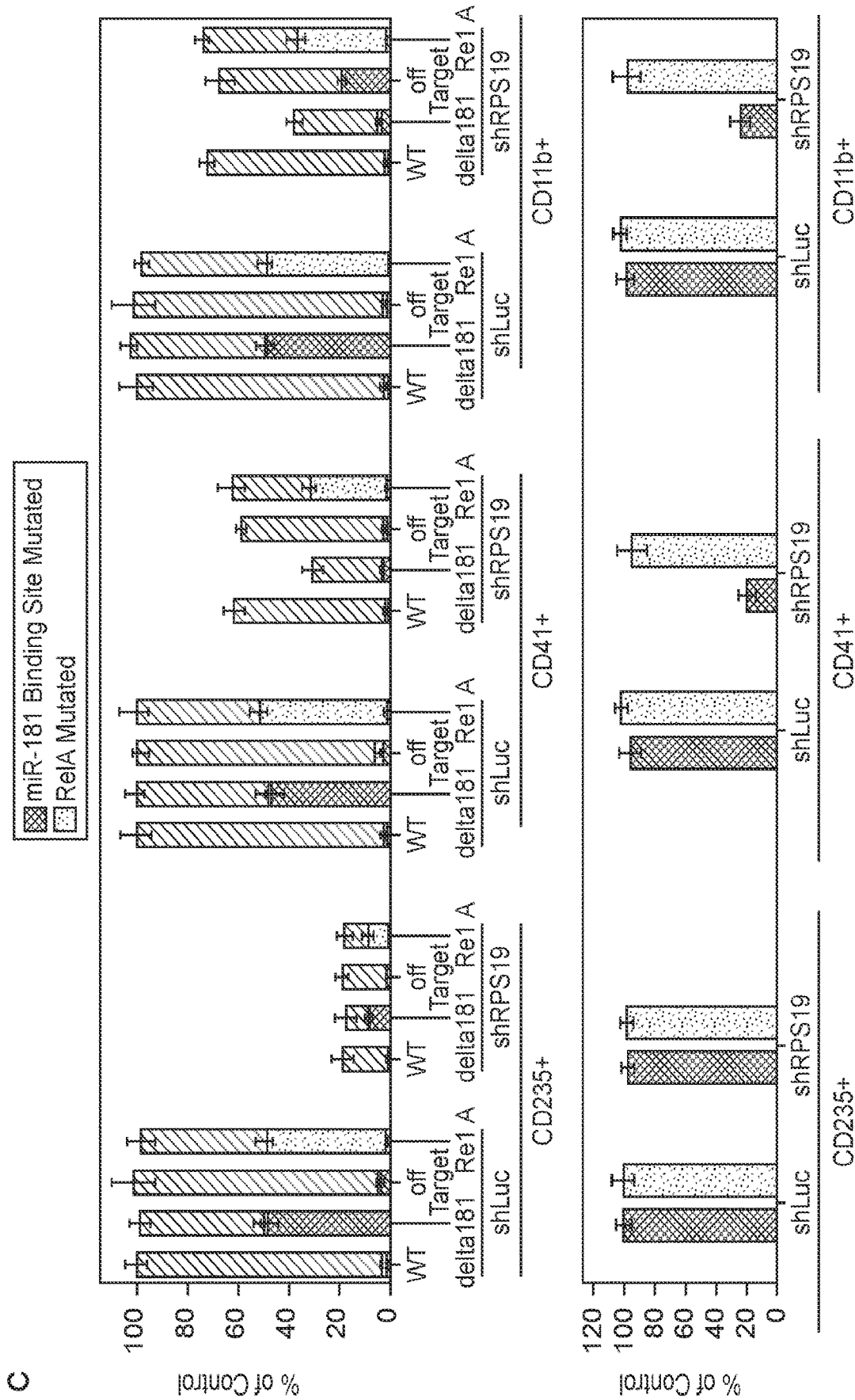

We first introduced NLK cDNA (using lentivirus) into CB CD34+ HPCs driven by the human elongation factor 1a (hEF1a) promoter with either no 3'UTR sequence, the native NLK 3'UTR sequence, or the 3'UTR sequence with the miR181 binding site mutated. As anticipated, miR181 levels were significantly elevated in non-erythroid lineages in comparison to erythroblasts (over 8-fold in CD41+ megakaryocytes and over 6.5-fold in CD11b+ myeloid lineages) and levels were not impacted by the expression of any of the recombinant NLK constructs or RPS19-insufficiency (FIG. 3, panel a—top portion). Similarly, the various NLK 3'UTRs had no impact on NLK activity (FIG. 3, panel a—middle portion), NLK expression (FIG. 3, panel a—bottom portion) or cell numbers (FIG. 3, panel b) during erythroid expansion. In contrast, the transduction of NLK cDNA without an intact miR181-binding site in the 3'UTR displayed dramatically increased NLK expression in megakaryocytes and myeloid cells with wild-type RPS19 levels (FIG. 3, panel a—bottom portion). In RPS19-insufficiency, megakaryocytes and myeloid cells with elevated NLK demonstrated catastrophic defects in lineage expansion. RPS19-insufficiency alone reduced expansion to 64.9% of control, but forced high expression of NLK (either by expressing NLK with no 3'UTR or mutated miR181 binding site) and resulted in such reduced expansion that no CD41+ cells were recovered (FIG. 3, panel b). Transduction of NLK with a wild-type 3'UTR demonstrated virtually identical expansion as RPS19-insufficiency alone (64.9% vs. 58.3% P=0.6799).

Although not abundant, RPS19-insufficient CD11b+ cells with elevated expression of NLK were recovered. RPS19-insufficiency alone reduced the myeloid population to 73.7% of control, but co-expression of NLK with no 3'UTR reduced that number 27.8%. Co-expression of NLK with a mutated miR181 binding site similarly yielded 30.1% of control. Co-expression of NLK with wild-type 3'UTR had similar cell recovery as RPS19-insufficiency alone (73.7% vs. 68.3%) (FIG. 3, panel b). As one might expect, NLK activity was induced in RPS19-insufficient myeloid cells with forced NLK expression (FIG. 3, panel a—middle portion), but not in the absence of RPS19-insufficiency.

In an alternative approach, the miR181 binding site of the NLK 3'UTR was targeted for mutation by CRISPR/Cas9 technology. After screening a selection of guide RNAs (gRNA) for the ability to both disrupt the predicted miR181 binding site sequence and functionally uncouple miR181 expression from NLK activation in a K562 model system, we introduced gRNA and Cas9 into control and RPS19- insufficient CB CD34+ HSPCs and expansion of erythroid, megakaryocyte and myeloid lineages was determined. A previously validated gRNA targeting RelA was utilized as a control. Mutation efficiency ranged from 35-50% in control cells for both NLK 3'UTR (blue bars) and RelA (red bars) guides and was consistent between hematopoietic lineages (FIG. 3, panel c—upper portion). Consistent with the idea that NLK has no role in normal erythropoiesis, the expansion of all 3 lineages (grey bars) were unaffected by NLK 3'UTR mutation in control cells (FIG. 3, panel c—upper portion). The expansion defect of RPS19-insufficient erythroid cells was similarly unaffected by NLK 3'UTR mutagenesis, as miR181 is not expressed in these cells (FIG. 3, panel c—upper portion). Although less than 50% of cells in the population carried NLK 3'UTR mutations, the expansion of these heterogeneous pools of megakaryocytes and myeloid cells displayed significantly less expansion than control populations (FIG. 3, panel c—upper portion). Of note, the percentage of mutation-baring cells ranged from 35-50% when RPS19 was expressed at wild-type levels, but during RPS19-insufficiency very few mutation-baring megakaryocytes or myeloid cells were recovered (FIG. 3, panel c—upper portion), suggesting these cells did not contribute to the expansion of these populations. After normalizing for mutation efficiency, the influence of mutation-baring cells on population expansion in control and RPS19-insufficency was calculated. No significant differences in the expansion of control or RPS19-insufficient erythroid cells were observed in cells carrying RelA or NLK 3'UTR mutations. However, both megakaryocytes and myeloid cells carrying NLK 3'UTR mutations, undergo strikingly less expansion. RelA mutations had a negligible effect in all lineages (FIG. 3, panel c-lower panel).

6. NLK Activation Inhibits Erythropoiesis by Downregulating c-Myb

Figure 4:
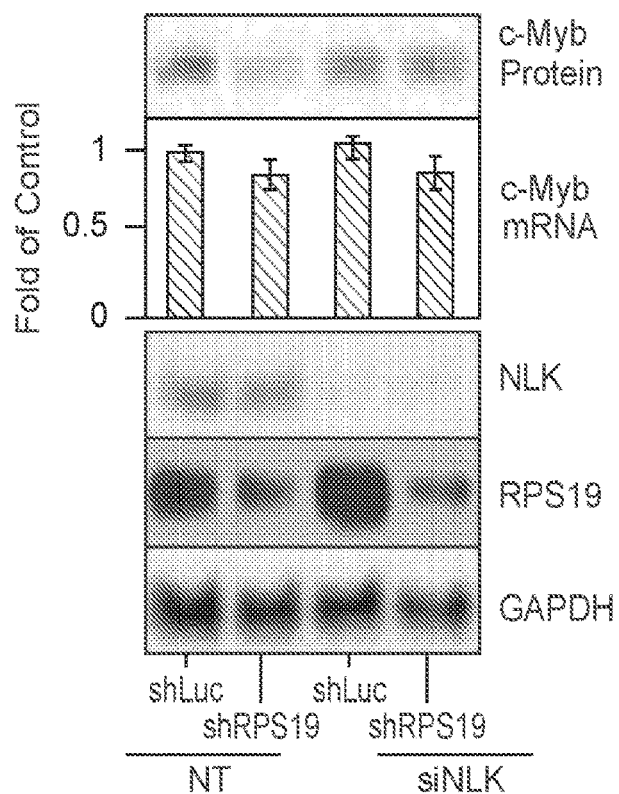
FIG. 4. NLK phosphorylation of c-Myb results in ubiquitination and proteasome degradation. Fetal liver CD34+ progenitors transduced with shRNA against luciferase (shLuc) or RPS19 (shRPS19) in conjunction with siRNA against NLK (siNLK) or a non-targeting sequence (NT). Cells were differentiated for 5 days and split into three aliquots. One aliquot was lysed and probed for c-Myb, NLK, RPS19 and GAPDH protein expression by western blot, while the second aliquot was subjected to qRT-PCR to examine c-Myb mRNA expression (a) The third aliquot was analyzed for NLK activity by kinase assay (b—upper) and ubiquitination assay (b—lower). Orange, blue and green bars represent the extent of NLK, Myb and raptor phosphorylation respectively. Values are expressed as a fold relative to activity in controls (shLuc/NT). White, grey and black bars designate the substrates NLK, c-Myb and raptor respectively with values designating the extent of ubiquitination observed of each substrate relative to control. (c and d) Kp53A1 cells alone, or transfected with plasmids expressing NT or siNLK were cultured for 30 h at 37 or 32° C. prior to lysis and western blotting for c-Myb, NLK and GAPDH. Myb mRNA levels were determined by qRT-PCR. (c) NLK kinase assays and cell ubiquitination assays were performed as above. (e) Kp53A1 cells were cultured at 37 (grey bars) or 32° C. (black bars), in the absence or presence of 1 µM staurosporine, prior to performing NLK kinase (left) and ubiquitination (right) assays examining c-Myb as a substrate. (f) After a 30 minute pretreatment in vehicle alone, lactacystin or chloroquine, Kp53A1 cells were switched from 37° C. to 32° C. for the indicated times. Cells were lysed, normalized for protein and split into two. C-Myb was immunoprecipitated from one sample before western blot analysis for phosphorylated serine, while the other sample was subjected to Western blot for c-Myb and GAPDH. (g) Cord blood CD34+ progenitors were transduced with shRNA against luciferase or RPS19 and siRNA against NLK or a non-targeting sequence and differentiated in erythroid media for 12 days. Expression of the c-Myb-dependent genes LMO2 (left) and KLF1 (right) was examined by qRT-PCR and fold of control are shown.
Figure 4:
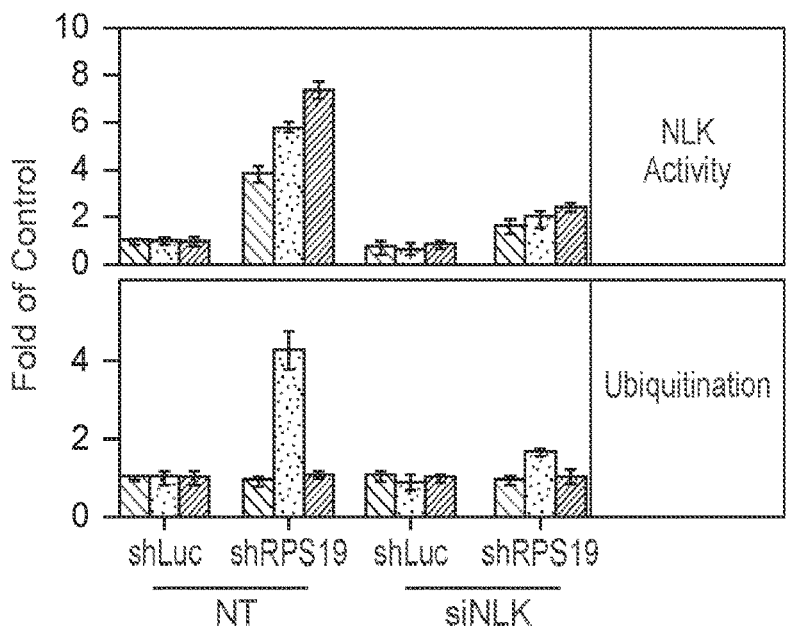
Figure 4:
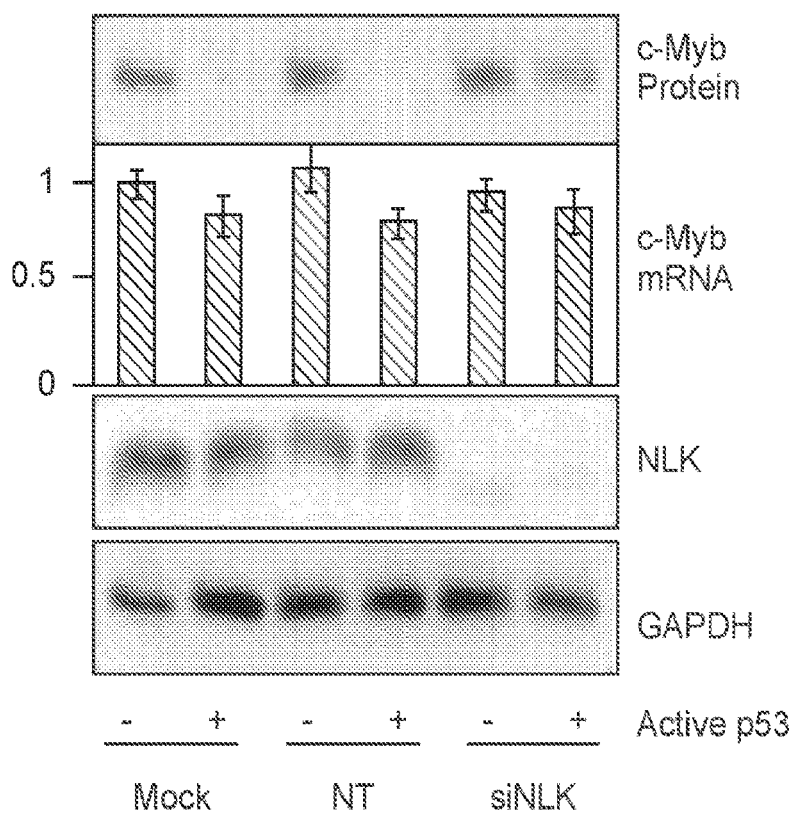
Figure 4:
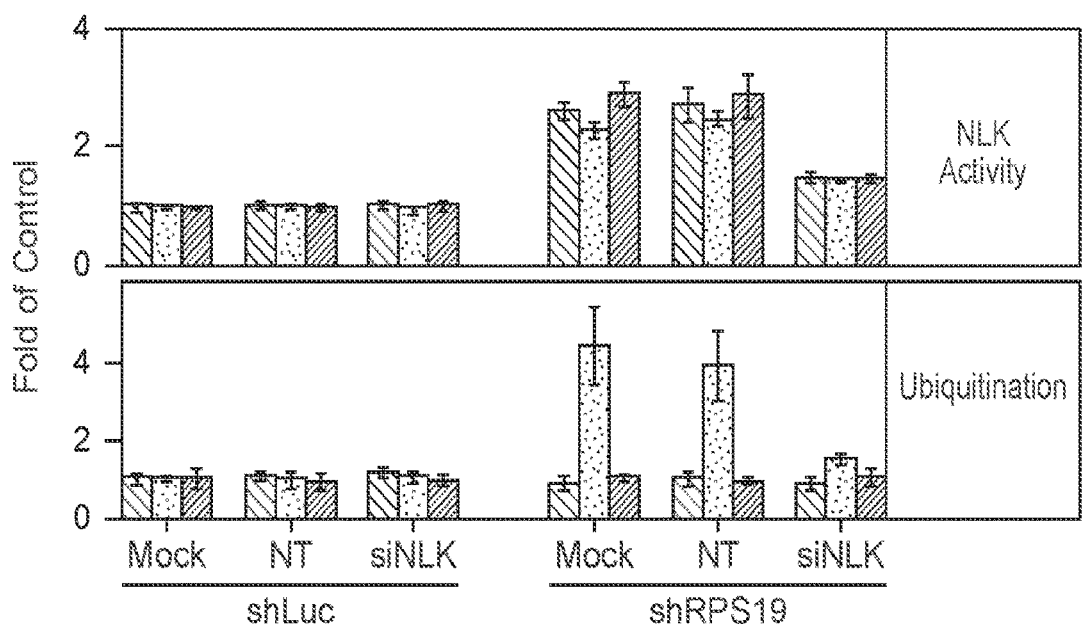
Figure 4:
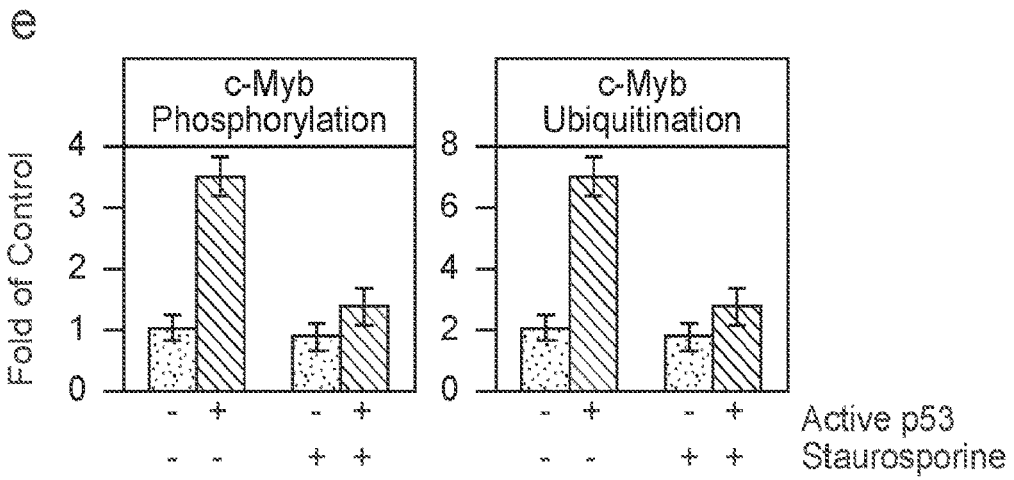
Figure 4:
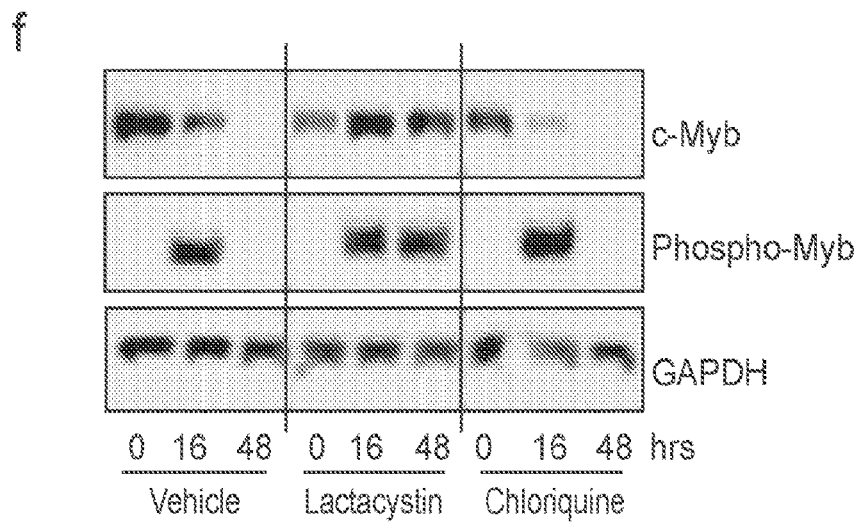
Figure 4:
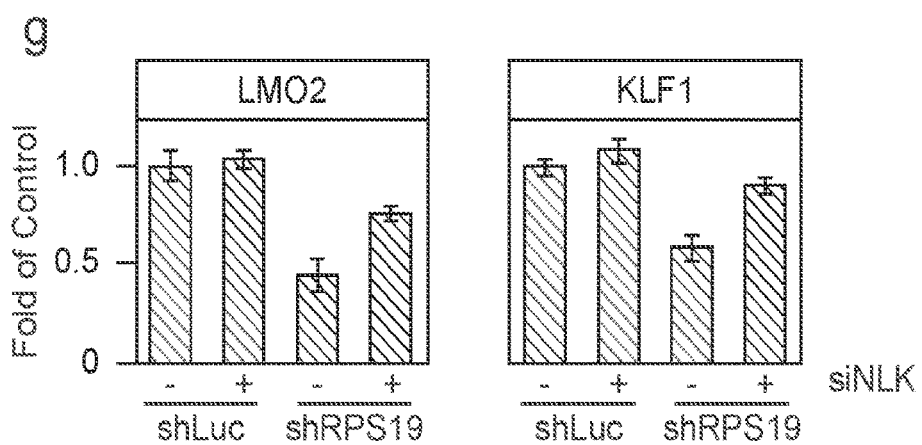

The pro-erythroid transcription factor c-Myb is critical for erythropoiesis[42], partially through upregulation of other erythroid differentiation factors[43]. Reduced c-Myb expression has been reported in DBA[9,44]. RPS19-insufficiency in differentiating CD34+ HSPCs displayed a mild 13% suppression of c-Myb transcription, but c-Myb protein levels decreased by over 80% (FIG. 4, panel a). Silencing NLK restored c-Myb protein expression in RPS19-insufficient cells without affecting transcription (FIG. 4, panel a). Activated NLK has been reported to facilitate c-Myb degradation through the phosphorylation of c-Myb at multiple residues, leading to subsequent ubiquitination and proteasome degradation[27]. We could not examine the phosphorylation status of c-Myb in expanding RPS19-insufficient erythroid progenitors as c-Myb protein is absent. So, to determine if NLK-mediated phosphorylation contributed to c-Myb protein loss, we tested if NLK immuno-purified from RPS19-insufficient cells could facilitate both phosphorylation and ubiquitination of exogenous c-Myb in vitro. As previously demonstrated (FIGS. 1-3), NLK immuno-purified from RPS19-insufficient progenitors increased in vitro phosphorylation of NLK (3.8-fold-orange bars), c-Myb (5.7-fold, blue bars) and raptor (7.3-fold, green bars) compared to controls. Treatment with siRNAs against NLK resulted in insufficient levels of activated NLK in the lysates to phosphorylate any of the substrates (FIG. 4, panel b—upper portion). We next examined ability of lysates extracted from RPS19-insufficient progenitors expressing control (NT) or siRNA against NLK to ubiquitinate the three immobilized substrates. RPS19-insufficient samples robustly increased ubiquitination of c-Myb (4.2-fold), but not NLK (0.9-fold) or raptor (1.1-fold), however only a 1.6-fold increase in c-Myb ubiquitination was observed in RPS19-insufficient progenitors with silenced NLK (FIG. 4, panel b—lower portion).

To obtain enough material for proteomic analysis following NLK activation, we developed a model system that mimicked the activation of NLK in the CML-derived megakaryocyte/erythroid progenitor line K562. These cells (Kp53A1) express a mutant p53 that is largely inactive when cultured at 37° C. and becomes highly active at 32° C.[45]. As observed in DBA, a p53-mediated an increase in p21 protein expression and decrease in both c-Myc and c-Myb protein levels following incubation of these cells at 32° C. Similar to RPS19-insufficient progenitors (FIG. 1, panel d), induction of active p53 (cultured at 37° C.) induced NLK activation leading to NLK (orange bars), c-Myb (blue bars) and raptor (green bars) phosphorylation and c-Myb ubiquitination, along with a reduction in cell numbers. Decreased expression of RPS19 has the same effect as increasing the temperature, although the synergy between RPS19 expression and p53 activity is highly sensitive, with cell death rapidly induced above a certain threshold.

Using the Kp53A1 cell system, we confirmed that c-Myb protein, but not mRNA, expression is reduced when p53 activation is elevated (cultured at 37° C.) and this is attenuated upon NLK silencing. However, NLK expression has no impact on c-Myb transcription (FIG. 4, panel c). Likewise, the in vitro phosphorylation of NLK, c-Myb and Raptor, as well as ubiquitination of c-Myb, was observed in differentiating HPCs (FIG. 4, panel d). To determine if phosphorylation precedes ubiquitination, we treated Kp53A1 cells with the general kinase inhibitor, staurosporine. This inhibitor reduced c-Myb phosphorylation in RPS19-insufficiency from a 4.3-fold increase relative to controls, down to a 1.3-fold increase (FIG. 4, panel e—left portion). Ubiquitination was similarly reduced from a 7.4-fold increase to only 2.3-fold of control (FIG. 4, panel e—right portion) in the presence of lysate with elevated p53 activity, demonstrating ubiquitination cannot occur in the absence of phosphorylation.

After inducing p53 activity, we tracked the intracellular c-Myb protein and phosphorylation alone or in the presence of proteasome or lysosomal inhibitors (lactacystin or chloroquine respectively). With or without chloroquine treatment, c-Myb protein was significantly downregulated 16 hours post p53 activation. In the presence of lactacystin, c-Myb protein levels were sustained (FIG. 4, panel f—upper portion). c-Myb phosphorylation was robust in all treatment groups at 16 h, however only lactacystin treatment sustained phosphorylation to 48 h (FIG. 4, panel f—middle portion). Activation of p53 had minimal impact on GAPDH (FIG. 4, panel f—lower portion). Collectively, these data show RPS19-insufficiency induces NLK activity, resulting in c-Myb phosphorylation. This triggers subsequent ubiquitination and degradation by the proteasome. Upregulation of pro-erythropoiesis transcription factors LMO2 and KLF1 are partially regulated by c-Myb and upregulation is significantly hampered during RPS19-insufficiency. Silencing of NLK in RPS19-insufficient HPCs restored LMO2 and KLF1 upregulation by 50.4% and 64.2% respectively (FIG. 4, panel g). These data indicate c-Myb protein degradation during RPS19-insufficiency is mediated by aberrant NLK activation.

Figure 5:
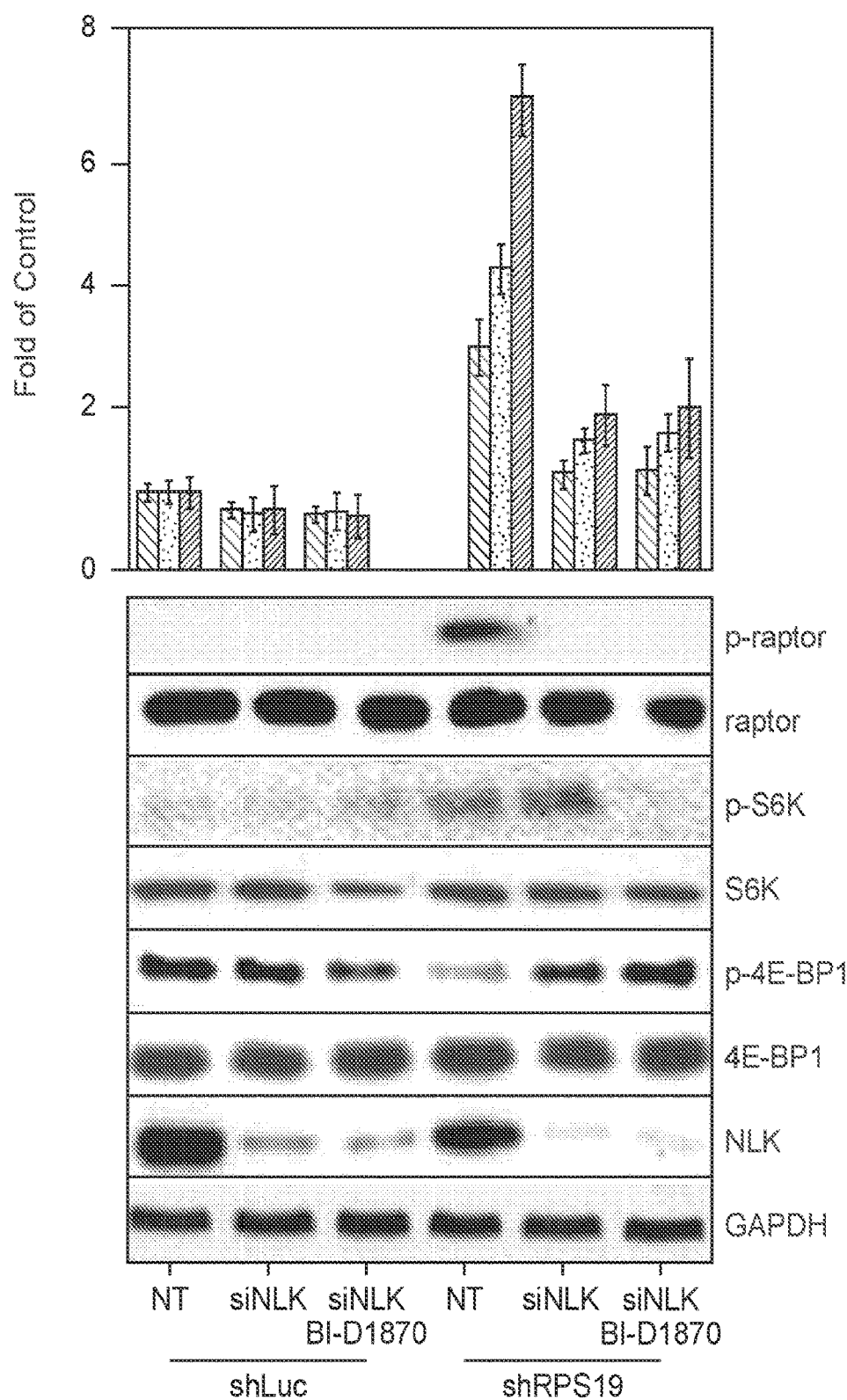
FIG. 5. NLK-mediated phosphorylation of raptor leads to reduced mTOR activity and increased autophagy. (a) Fetal liver CD34+ progenitors were transduced with controls or shRPS19 and differentiated for 5 days in the presence or absence of 5 µM BI-D1870 (RSK inhibitor). Samples were lysed and normalized for protein abundance before being subjected to immunoprecipitation of NLK, raptor, S6K and 4E-BP1. Immunoprecipitated NLK was utilized to examine NLK activity (a—top panel—Orange, blue and green depict NLK, Myb and raptor phosphorylation respectively), while raptor, S6K and 4E-BP1 were subjected to western blotting for phosphorylated serine/threonine residues (bottom panels). In parallel, lysates were probed for total raptor, S6K, 4E-BP1, NLK and GAPDH (bottom panels) by Western blotting. (b) Cord blood CD34+ progenitors were transduced with shRNA against luciferase (shLuc) or RPS19 (shRPS19) and siRNA against NLK (siNLK) or a non-targeting (NT) sequence and differentiated for 8 days. Cells were fixed, permeabilized and incubated with Cy3-labeled antibody against raptor (pseudo-colored red) and lysosomes were visualized by incubation with FITC-labeled antibody recognizing LAMP1 (pseudo-colored green). Areas of co-localization (merge) are indicated in yellow and yellow dotted boxes are magnified in inserts to the far right. (c) Cord blood progenitors were transduced with shRNA against luciferase (top) or RPS19 (bottom) in conjunction with non-targeting (blue peak) or siRNA against NLK (pink peak) and incubated with an intracellular stain visualizing LC3-containing autophagosomes prior to flow cytometry. (d) Cells treated as above were plated in 96 wells and absorbance measured at a wavelength of 520 nm. The bars represent the fold induction above control (shLuc/NT). (e) Cells were treated as above and visualized by immunofluorescence microscopy. Inserts are magnified views of the indicated regions depicting representative cells (top panels). After imagining, 100 cells per group were analyzed and the number of intense fluorescent puncta per cell was scored (lower panels). Data shows the average calculated from three separate experiments.
Figure 5:
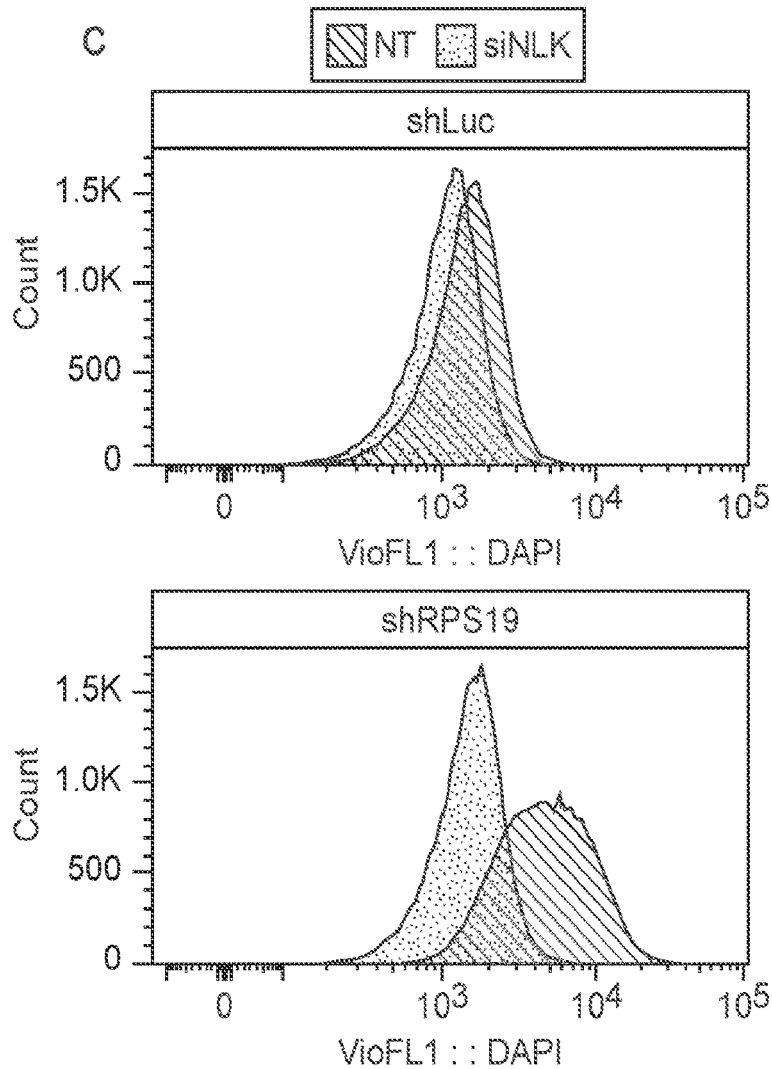
Figure 5:
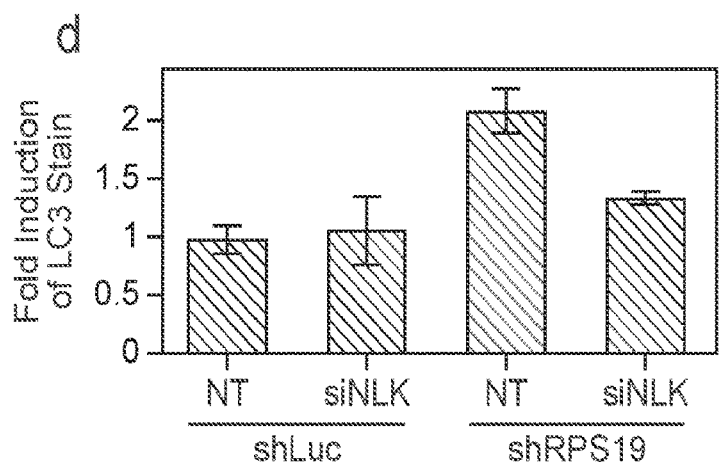
Figure 5:
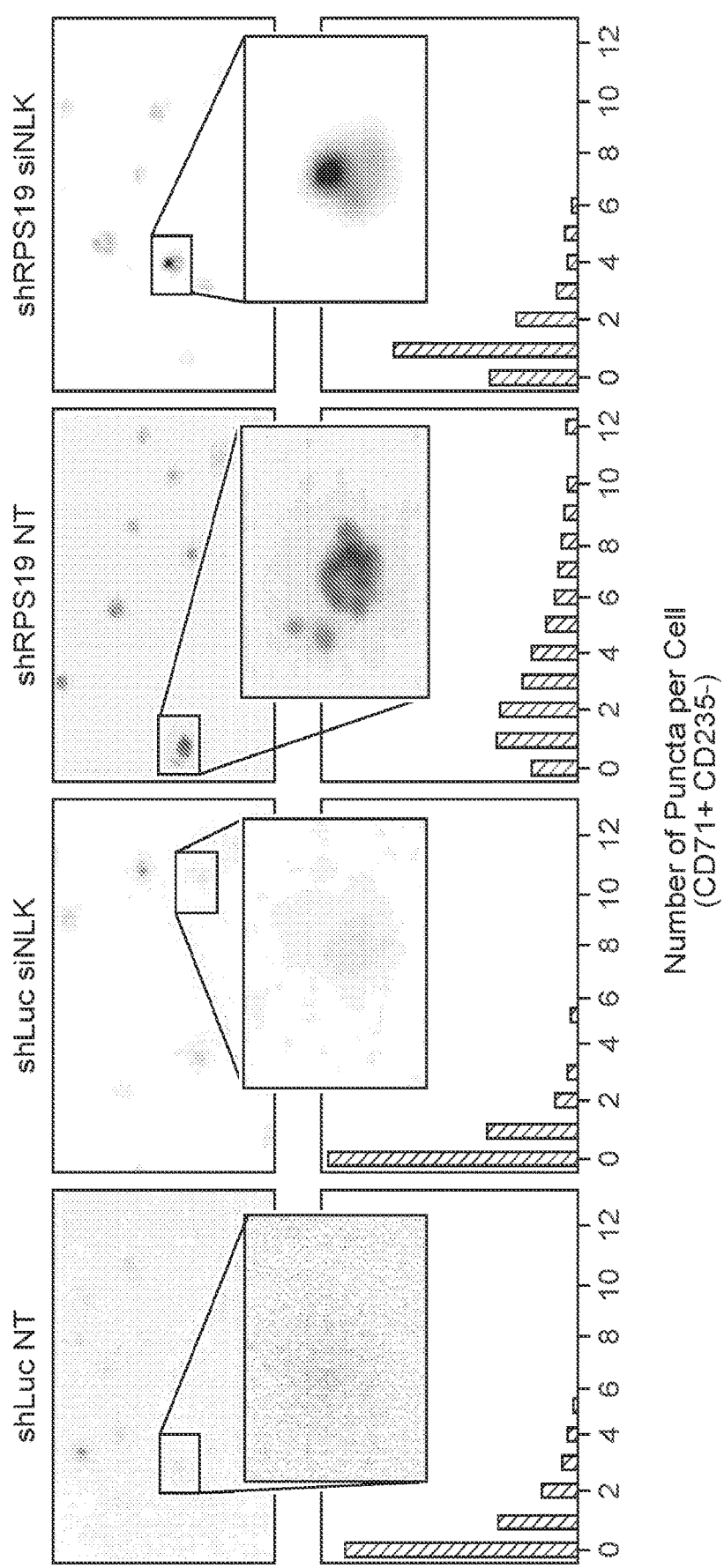

7. NLK Activation in RPS19-Insufficiency Increases Autophagy Through mTOR Deregulation Raptor is the regulatory component of the mTOR Complex 1 and a substrate of NLK in osmotic and oxidative stress. Raptor phosphorylation leads to uncoupling of mTORC1 signaling[19]. We determined immuno-purified NLK from human and murine RPS19- and RPL11-insufficient progenitors, as well as derived from DBA patients can phosphorylate raptor in vitro (FIGS. 1-4). However, to examine if raptor serves as an intracellular substrate we analyzed its phosphorylation status in differentiating control and RPS19-insufficient progenitors from fetal liver, in the presence or absence of siRNA targeting NLK. RPS19-insufficiency induced a robust phosphorylation of raptor (green bars) that did not occur in the absence of NLK (FIG. 5, panel a—top portion). Silencing of NLK was achieved as evidenced by an absence of phosphorylation of any NLK substrates (FIG. 5, panel a—top portion) and pronounced attenuation of NLK protein expression (FIG. 5, panel a, 2nd portion from bottom). As NLK-mediated phosphorylation has been reported to inhibit mTORC1 activity, we examined the phosphorylation status of two mTOR substrates, 4E-BP1 and S6K. Intriguingly, 4E-BP1 phosphorylation was reduced in RPS19-insufficiency, and was rescued upon NLK silencing (FIG. 5, panel a, $5^{th}$ portion from top) however, S6K phosphorylation was increased in RPS19-insufficiency and not influenced by NLK knockdown (FIG. 5, panel a, $3^{rd}$ portion from top). Increased phosphorylation of S6K in human models of DBA has been reported previously[11,46] and phosphorylation can be mediated by a number of kinases. S6K phosphorylation is significantly reduced in murine $RPL11^{+/lox}$ progenitors (data not shown). One potential kinase, RSK has been implicated in S6K phosphorylation in DBA[47]. Addition of BI-D1870 (RSK inhibitor) 5 µM was added to differentiating RPS19-insufficient cells and S6K phosphorylation was reduced to below basal levels (FIG. 5, panel a, 3rd portion from top), suggesting RSK, not mTOR, is the likely kinase in DBA. Changes in phosphorylation levels was not due to increased protein expression as raptor (FIG. 5, panel, 2nd portion from top), S6K (FIG. 5, panel a, 4th portion from top), 4E-BP1 (FIG. 5, panel a, 5th portion from top) and GAPDH (FIG. 5, panel a, bottom portion) total protein levels remained unchanged. NLK-dependent phosphorylation of raptor was also observed in Kp53A1 cells upon increased activation p53.

Three approaches were used to evaluate the ability of raptor to localize to the lysosome for activation by membrane-associated Rheb proteins. For the first approach, we used immunofluorescence microscopy to assess the extent of co-localization of raptor and the lysosomal marker, LAMP1, in control and RPS19-insufficient CB HPCs either expressing siRNA against NLK or a NT control. In control cells, raptor is largely cytoplasmic, however a significant portion co-localizes with LAMP1 at the lysosome (FIG. 5, panel b, upper portion) and this is unchanged in the absence of NLK (FIG. 5, panel b 2nd portion from top). During RPS19-insufficiency the extent of raptor co-localization with LAMP1 is significantly reduced (FIG. 5, panel b—2nd portion from bottom). Silencing NLK largely restores lysosomal co-localization (FIG. 5, panel b, bottom portion), indicating NLK is largely responsible for blockage in raptor trafficking to the lysosomal membrane. The second approach to determine if NLK influences raptor targeting to the lysosome, examines the levels of raptor in enriched lysosomal fractions. Due to constraints using differentiating progenitors, we again utilized Kp53A1 cells. As we observed in immunofluorescence studies (FIG. 5, panel b), the majority of raptor was present in the cytosolic fraction, although a significant percentage was detected in the enriched lysosomal fractions. Lysosomal raptor levels were reduced by approximately 80% in RPS19-insufficiency but significantly rescued (approaching 60%) upon silencing of NLK. Our final approach was also performed in Kp53A1 cells and examined the association of Rheb (localized in lysosomal membrane) with mTOR (complexed with raptor in mTORC1) by co-immunoprecipitation. Although neither Rheb nor mTOR protein levels were influenced by RPS19 or NLK expression, the association of the two proteins was dramatically disrupted in RPS19-insufficiency. However, silencing of NLK restored Rheb and mTOR association to levels similar to controls. Collectively, our data indicate NLK activation in RPS19-insufficiency inhibits mTOR activation by phosphorylation of raptor to prevent mTORC1 localizing to the lysosome to be activated.

Autophagy is regulated by mTORC1[48]. Active, mTOR suppresses autophagy[48], therefore we formulated the hypothesis that NLK activation during RPS19-insufficiency would increase autophagy in DBA erythroid progenitors through raptor phosphorylation. Autophagy is a critical step in enucleation during late erythroid maturation[49], but increased, premature autophagy has been reported in DBA[11,12]. To test our hypothesis that NLK activation is contributing to premature autophagy, we analyzed the incorporation of a fluorescent autophagosome dye in control and RPS19-insufficient differentiating CB HPCs, in the presence or absence of siNLK, by flow cytometry, fluorescence reader, and fluorescence microscopy. An increase in autophagy was detected in differentiating RPS19-insufficient HPCs, by both flow cytometry (FIG. 5, panel c) and a fluorescence plate reader assay (FIG. 5, panel d), which was largely corrected in both assays by silencing NLK.

These findings were confirmed by fluorescence microscopy when the number of large fluorescent puncta (assumed to be autophagosomes) in individual cells was quantified. To ensure non-erythroid and mature erythroblasts didn't convolute our interpretations, differentiating HPCs were sorted to include CD71+ CD235− early erythroid progenitors. Representative images are displayed (FIG. 5, panel e—upper portions) while the percentage of cells containing various numbers of autophagosomes corresponding to each treatment is displayed in the graphs below (FIG. 5, panel 3—lower portions). RPS19-insufficiency shifted the distribution of autophagosome-containing cells from a majority containing none (63%), to a population in which a majority of cells contained 2 or more (68%) (FIG. 5, panel e—lower portions). Silencing NLK expression in RPS19-insufficient erythroid progenitors did not fully rescue the population and the majority of cells still contained at least one autophagosome, however the majority of these contained only a single autophagosome (50%) (FIG. 5, panel e—lower portions). Kp53A1 cells expressing increased active p53 also displayed NLK-dependent autophagy as determined by flow cytometry and fluorescence plate reader assay. Taken together, our data indicate NLK activation in RPS19-insufficiency induces autophagy in erythroid progenitors by inhibiting mTORC1 activation through direct phosphorylation of raptor.

Figure 6:
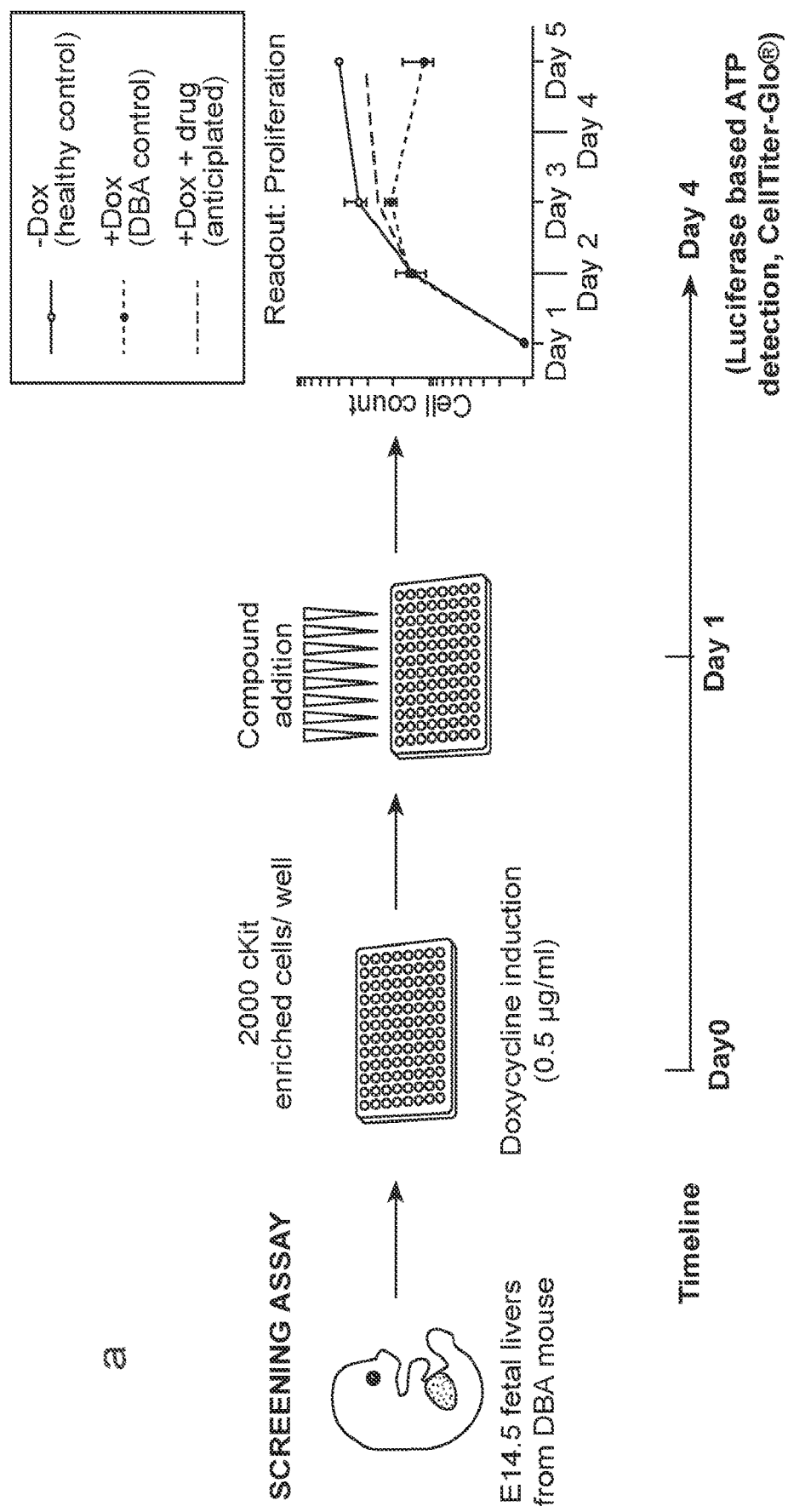
FIG. 6. TGFβR1 inhibitors that also decrease NLK activity improve erythropoiesis in hematopoietic stem cells from murine models of RPS19-insufficiency. (a) Schematic of assay utilized to screen compounds for effects on erythroid progenitor cell expansion. Lin-Kit+fetal liver cells were obtained from mouse embryos expressing tet-on shRNA against RPS19, at day E14.5-15.5. Cells were plated at 2000 cell per well in 96-well plates in the presence or absence of doxycycline. Relative amounts of live cells were quantified by luciferase-based Cell titer-Glo® assay. (b) TGFβR1 inhibitors including SB431542 were assessed for their ability to increase cell expansion in RPS19-insuffiency. As a control, untreated (no doxycycline) is represented at the far left while all other samples were treated with doxycycline to induce RPS19-insufficiency. (c) Kit+ erythroid progenitors were grown in the absence of doxycycline and in the presence of 10 µM of indicated compound. As a comparison, samples with no inhibitor added are represented in grey. In addition, cells were either left untreated, or treated with 5 ng/ml of TGFβ1 for 5 days before being subjected to Cell TiterGlo® assay. (d) Schematic indicating Smad2 and Smad3 serve as substrates for activated TGFβR1 while NLK, c-Myb and raptor serve as substrates for activated NLK (upper panel). K562 cells were stimulated with 5 ng/ml TGFβ1 for 10 min and TGFβR1 was immunopurified after cell lysis and protein normalization. TGFβR1 was added to purified Smad2 (middle panel) and Smad3 (lower panel) in the presence of ATP and Mg$^{2+}$ at 37° C. for 30 min. As per NLK kinase assay, phosphorylation of substrates was detected by antibody raised against phosphorylated serine residues. Compounds with inhibitory properties against TGFβR1, other TGFB pathway factors, or NLK expression were added to the kinase reactions at concentrations known to inhibit TGFB signaling. The most potent stimulator of murine erythropoiesis (SD208) is depicted with a star. (e) Active NLK was immunopurified from Kp53A1 cells cultured at 32° C. for 24 h and added to NLK substrates NLK (upper), c-Myb (middle) and raptor (lower), in the presence of the same inhibitory compounds.
Figure 6:
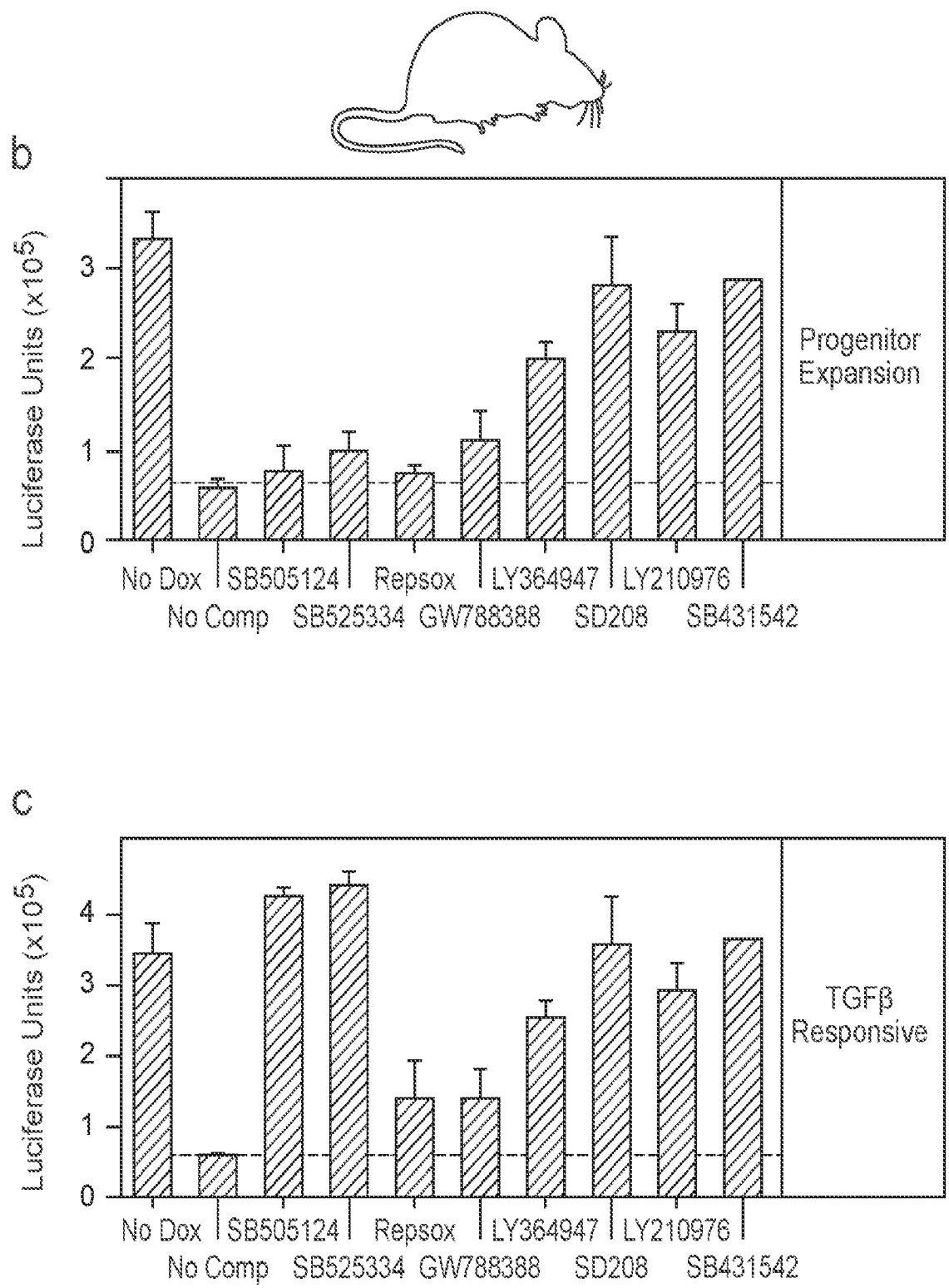
Figure 6:
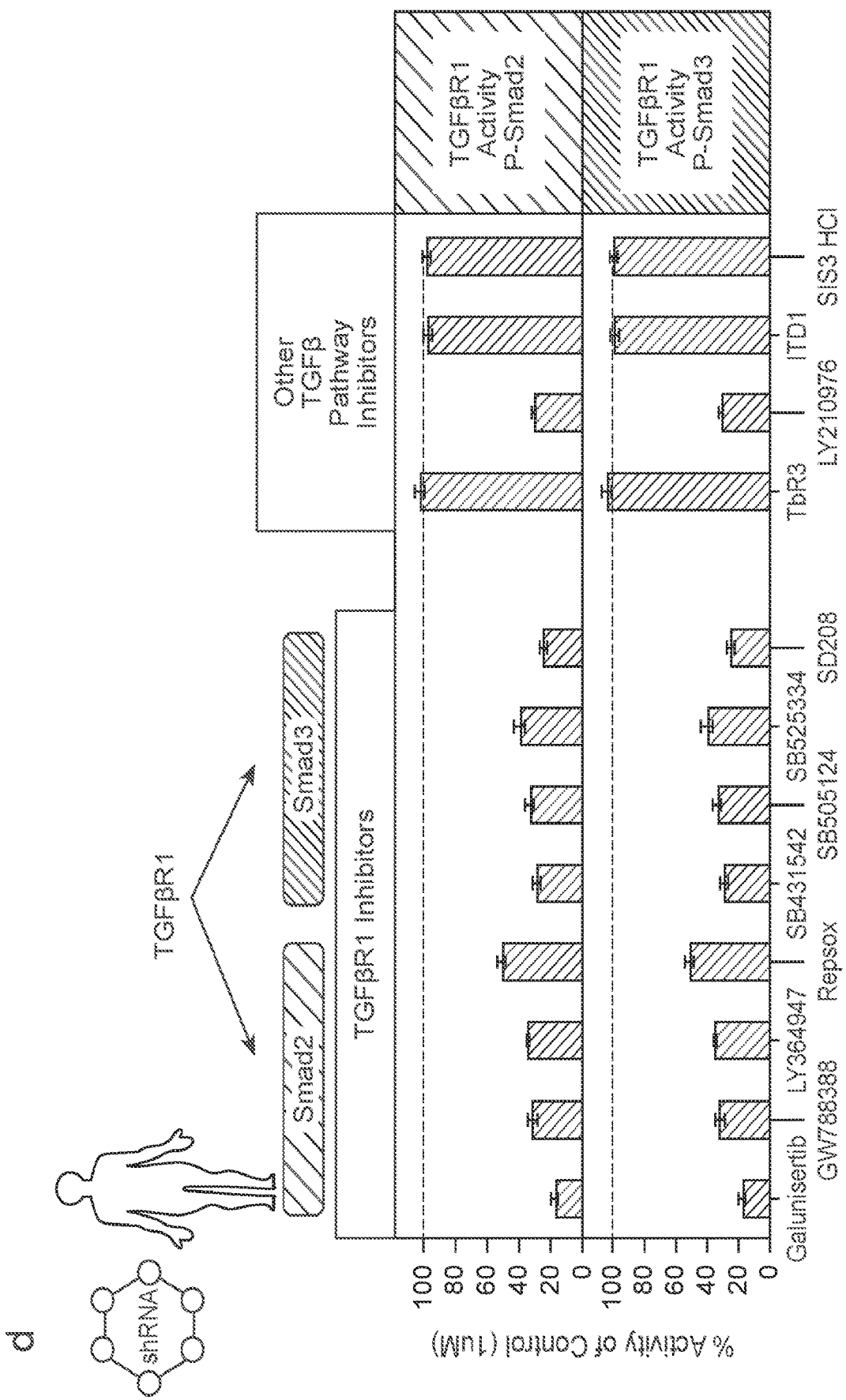
Figure 6:
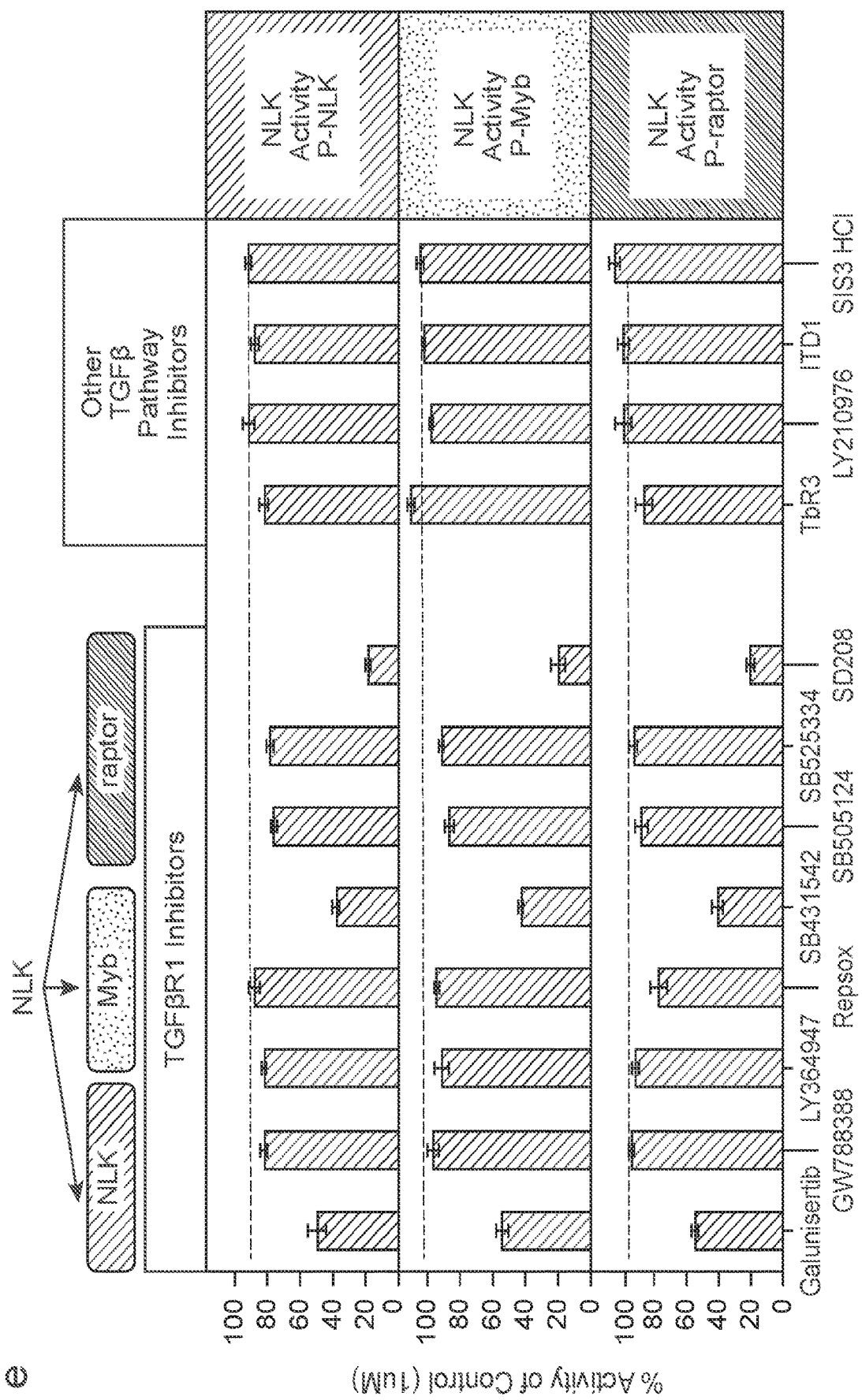

8. Increased Erythropoiesis by Subset of TGFβ Inhibitors is Through Off-Target NLK Inhibition Utilizing fetal livers at E14.5-E15.5 from tetracycline-inducible shRPS19-inducible mice, compounds were screened for the ability to rescue c-Kit+ erythroid expansion in doxycycline-treated hematopoietic progenitors over 4 days (FIG. 6, panel a) and compound SB431542, a known inhibitor of the TGFβ pathway through inhibition of ALK4,5 and 7, was amongst the strongest hits. This compound was also identified in a similar screen using reprogrammed hematopoietic progenitors[12]. Several TGFβ inhibitors in the murine RPS19-insufficient model were thus tested at 10 µM and only SB431542 and SD208 significantly rescued c-Kit+ erythroid expansion, while six other TGFβ inhibitors displayed no significant effect (FIG. 6, panel b). Erythroid growth in murine RPS19-insufficiency by SB431542 and SD208 were rescued with $EC_{50s}$ of 5 μM and 0.7 μM respectively. All of the compounds inhibit TGFβ in our murine model, as all rescued proliferation of TGFβ-treated c-Kit+ cells to varying extents (FIG. 6, panel d). Collectively, this suggests the TGFβ pathway is not the most relevant target of SB431542 and SD208 in rescuing erythroid expansion in murine RPS19-insufficiency.

Kinase Profiling of SD208 indicated NLK to be a robust target and kinase activity is 96.8% inhibited at 10 μM (data not shown), suggesting activated NLK may serve as a target in the RPS19-insufficiency murine model, but also in other DBA model systems and DBA patients. To systematically address this possibility, we first assessed the effect of eight commercially available TGFβR1 inhibitors, including SD208 and SB431542, along with inhibitors of four other proteins in the TGFβ signaling pathway.

The ability of the compound panel to inhibit active NLK and TGFβR1 (immuno-purified from activated Kp53A1 and TGFβ-treated K562 cells respectively) in vitro kinase activity was assessed at 0.1, 1 and 10 μM. Similar to the murine functional assay, all the TGFβR1 inhibitors tested inhibited the phosphorylation of TGFβR1 substrates, Smad2 and Smad3 (FIGS. 6, panel d) at 1 μM, ranging from approximately 50% to 90% efficiency. In contrast, the two compounds that increased erythroid expansion in murine RPS19-inisufficiency (SD208 and SB431542) inhibited NLK activity by approximately 80% and 55%. Although not tested in the murine model, we also observed significant (40-45%) NLK inhibition by Galunisertib (FIGS. 6, panel e). Apart from LY210976, which is a dual inhibitor of both TGFβR1 and R2, we would not have anticipated direct inhibition of TGFβR1 in vitro as the selected inhibitors target other members of the TGFβ pathway.

Figure 7:
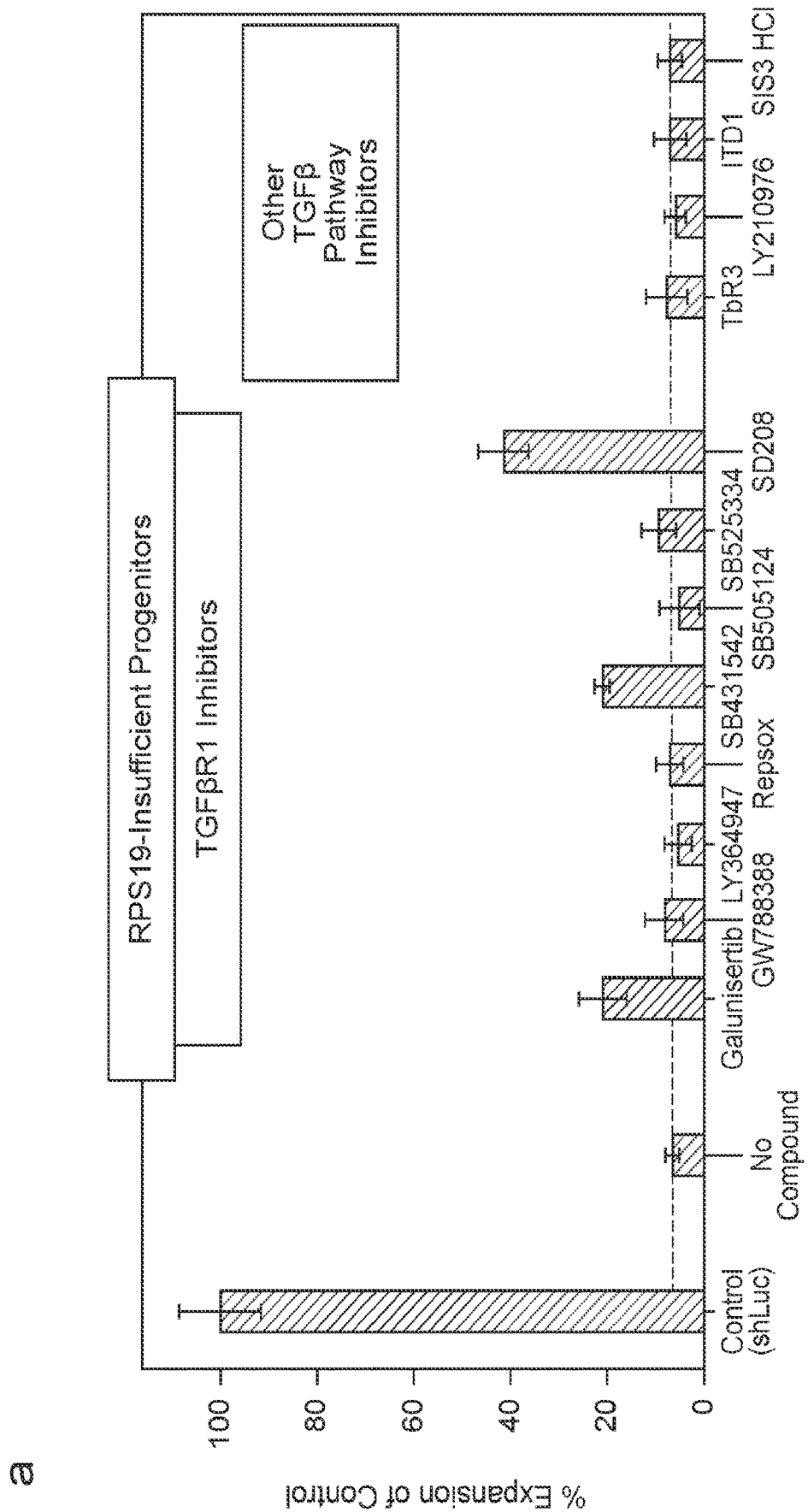
FIG. 7. SD208 increases erythroid expansion in human model of DBA through inhibition of NLK and not TGFβ. (a) Differentiating cord blood CD34+ progenitors were transduced with shRNA against luciferase or RPS19 and treated with inhibitors at working concentrations for TGFβ inhibition every three days. Cells were counted and CD235+ erythroid cells were assessed by flow cytometry after 15 days. (b) Prior to flow cytometry, 5000 cells per group were taken from differentiating cultures for NLK kinase assay. (c) CD34+ progenitors were transduced with shRNA against luciferase or RPS19 and non-targeting or siRNA against NLK. After sorting, samples were split into two groups and either treated with vehicle or SD208 every three days. After 15 days cells were counted and subject to flow cytometry to compare the expansion of maturing CD235+ erythroid (left panel) and CD11b+ myeloid cells (right panel). (d) Cord Blood CD34+ progenitors were transduced with shRNA against luciferase (left panel) or RPS19 (right panel) differentiated in erythroid media for 15 days alone, or in the presence of SB525334 or SD208 at 5 µM. Cells were counted and CD235+ erythroid (D—upper) and CD11b+ myeloid cell (D—lower) percentages were determined by flow cytometry. The number of erythroid or myeloid cells is expressed as a percentage of the number of that lineage with no cytokine or drug treatment.
Figure 7:
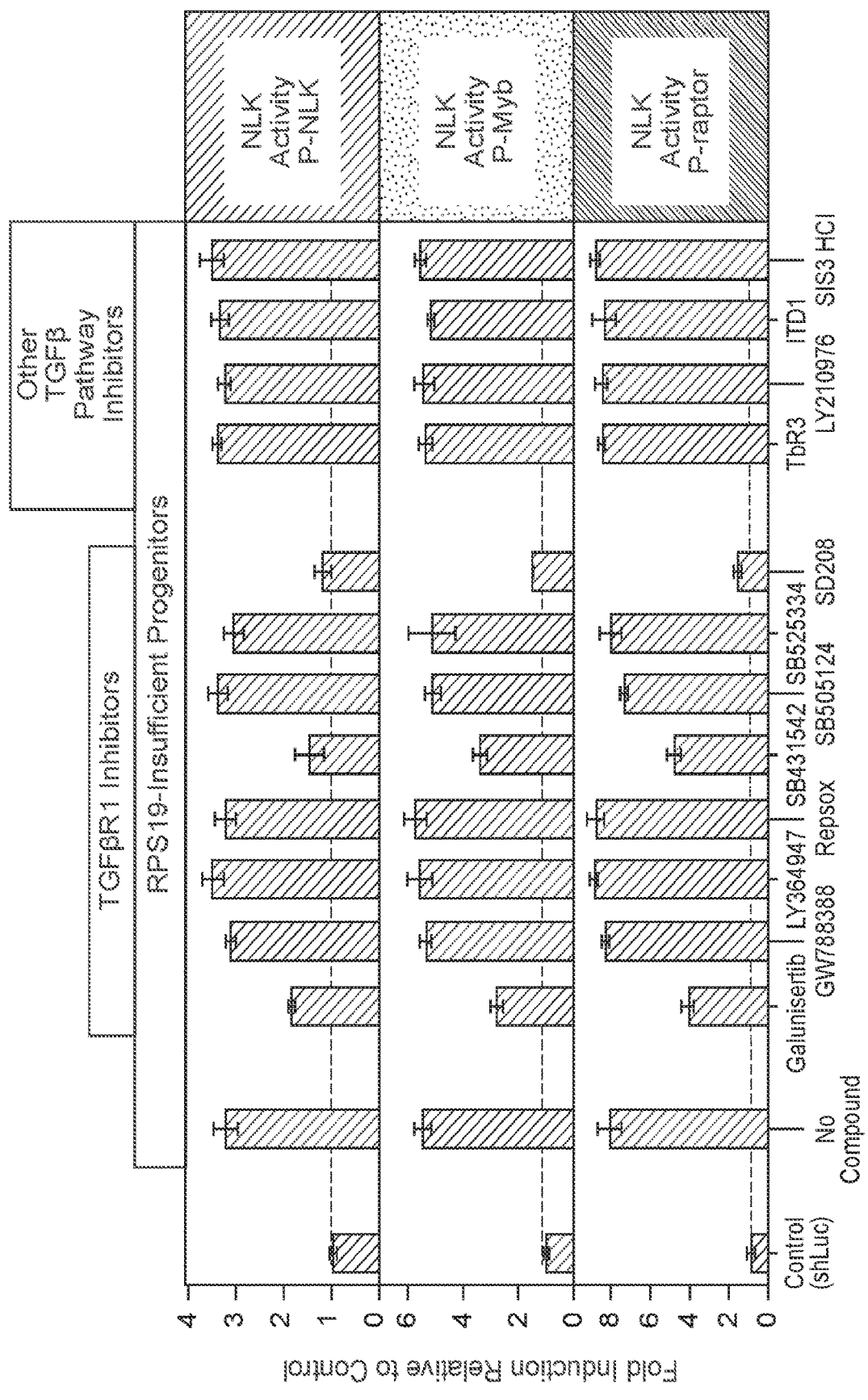
Figure 7:
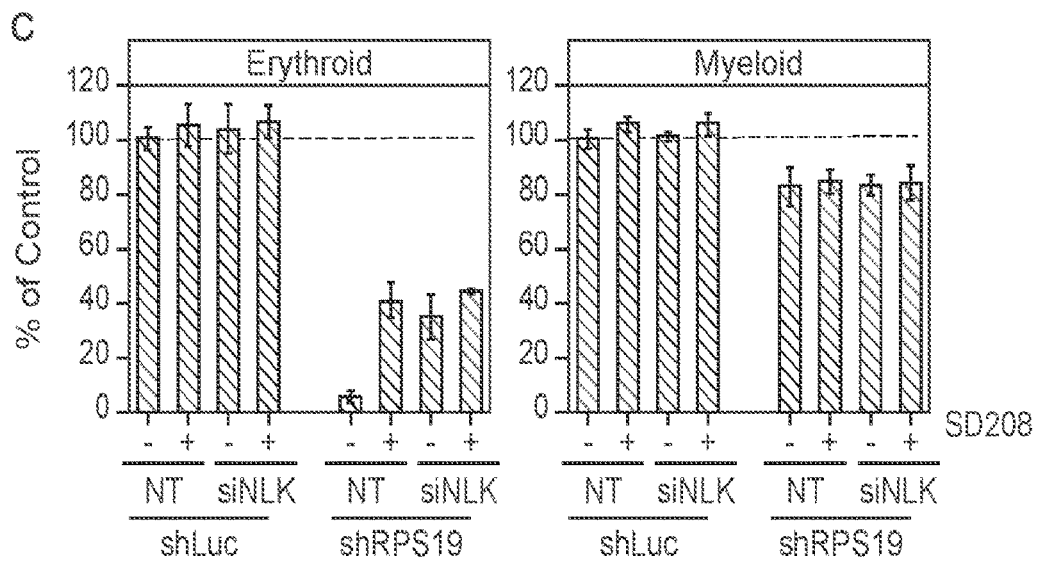
Figure 7:
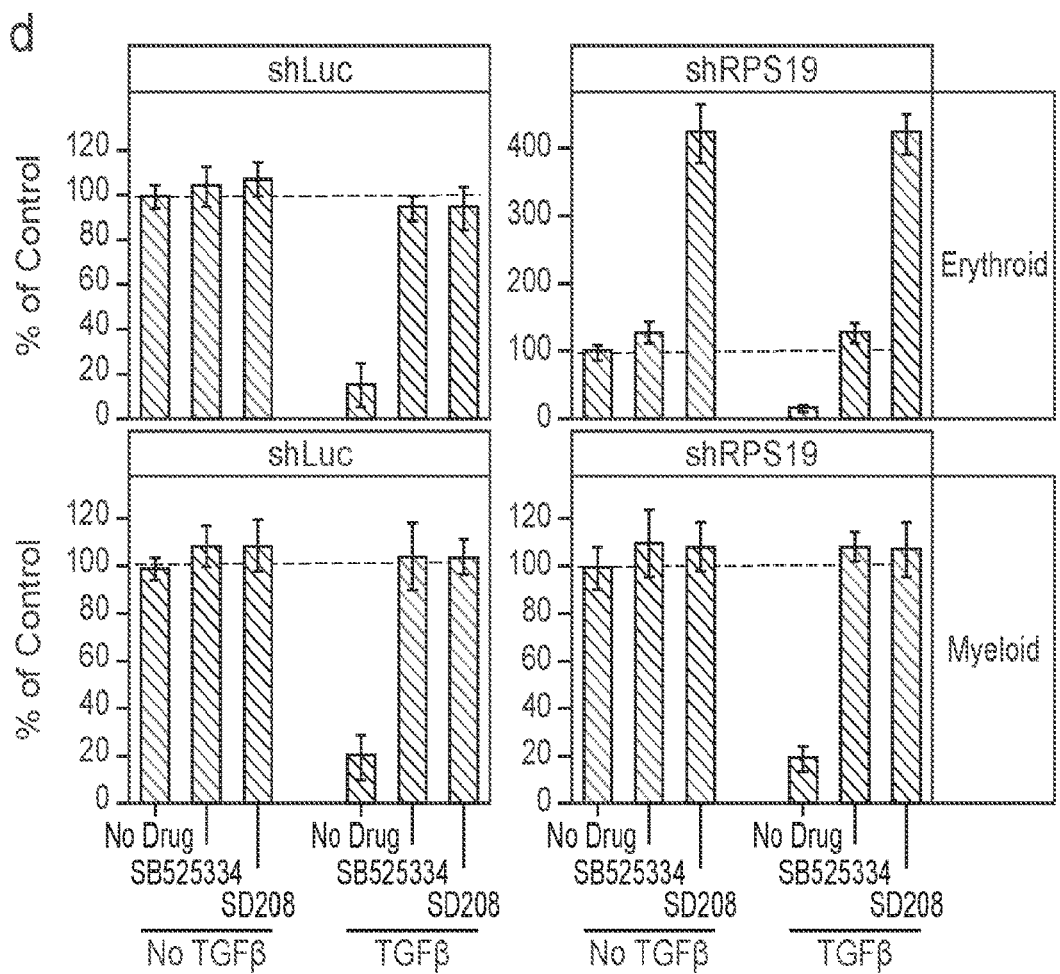

Having determined a number of compounds could inhibit both NLK activity in vitro and increase erythroid expansion in murine RPS19-insufficiency, we examined the ability of these inhibitors to influence erythroid expansion and NLK activity in human control and RPS19-insufficient progenitors undergoing erythropoiesis at concentrations published to efficiently block intracellular TGFβ signaling. Transduction of shRNA against RPS19 reduced CD235+erythroblast expansion to 6.6% of controls (shLuc). SD208, SB431542 and Galunisertib increased erythroid expansion in RPS19-insufficiency by 6.3-fold, 3.2-fold and 3.2-fold respectively (FIG. 7, panel a), correlating to 41.5%, 21% and 21% of control (FIG. 7, panel b). NLK immuno-precipitated from SD208-treated cultures demonstrated a 92.5% reduction in kinase activity. In the same assay, SB431542 reduced NLK activity by 73.6% and Galunisertib by 61.2%. Other TGFβ pathway inhibitors had a negligible impact (FIG. 7, panel b). As was observed following NLK knockdown, the effect of NLK inhibition was restricted to erythroid expansion with no significant effect in megakaryocyte or myeloid expansion. No inhibitor had a significant effect on expansion of any hematopoietic lineages in controls (shLuc), although all TGFβ inhibitors had a mild increase on megakaryocyte and myeloid expansion and an increasing trend in erythroid cells.

9. SD208 Improved Erythropoiesis Through NLK Inhibition

Off-target effects of SD208, SB431524 and Galunisertib, other than NLK, may contribute to erythroid expansion. However, NLK gene silencing and SD208 treatment yielded similar improved erythroid expansion as siNLK (FIGS. 2 and 7, panel a). To further scrutinize the role of off-target drug effects, we utilized siRNA against NLK concurrent with SD208 treatment. Similar to FIG. 7, panel a, SD208 treatment improved CD235+ erythroblast expansion to 40.3% observed in controls. Consistent with FIG. 2, siRNA against NLK improved erythropoiesis to 34.2% of controls. SD208 treatment in RPS19-insufficient erythroid progenitors expressing siRNA against NLK failed to show significant improvement in erythroid expansion over either treatment alone, with 43.6% of the erythroblasts generated in controls (FIG. 7, panel c). This strongly suggests the most relevant target of these compounds in ribosomal-insufficiency is NLK.

TGFβ inhibits proliferation and differentiation of early hematopoietic progenitors in murine and human systems[50]. RPS19-insufficiency inhibited erythroid expansion by 93% and the addition of exogenous TGFβ (5 ng/ml) to control (shLuc) also reduced erythroid progenitors by 85% (FIG. 7, panel d—top left portion) as well as reduced myeloid progenitors by 80% (FIG. 7, panel d—bottom left portion). Interestingly, exogenous TGFβ further hampered erythroid expansion of RPS19-insufficient progenitors by an additional 86% (FIG. 7, panel d), which was almost identical to the level of inhibition of control cells. The addition of a TGFβR1 inhibitor with no NLK-inhibitory activity (SB505124) was able to restore erythroid and myeloid expansion of control and RPS19-insufficiency to levels of at least 95% of that observed in cultures not treated with TGFβ (FIG. 7, panel d). This contrasts with SD208 (both TGFβR1 and NLK inhibitory activities). While in control cells and RPS19-insufficient myeloid cells, SD208 restored expansion similar to untreated cultures, RPS19-insufficient erythroid expansion was significantly enhanced increased above 100% (4.1-fold) of non-TGFβ-treated cells (FIG. 7, panel d—top right portion). The overall erythroid expansion mediated by SD208 in RPS19-insufficiency displayed no difference between TGFβ-treated or -untreated cells, further supporting a model in which SD208 improves erythropoiesis independent of TGFβ suppression.

Figure 8:
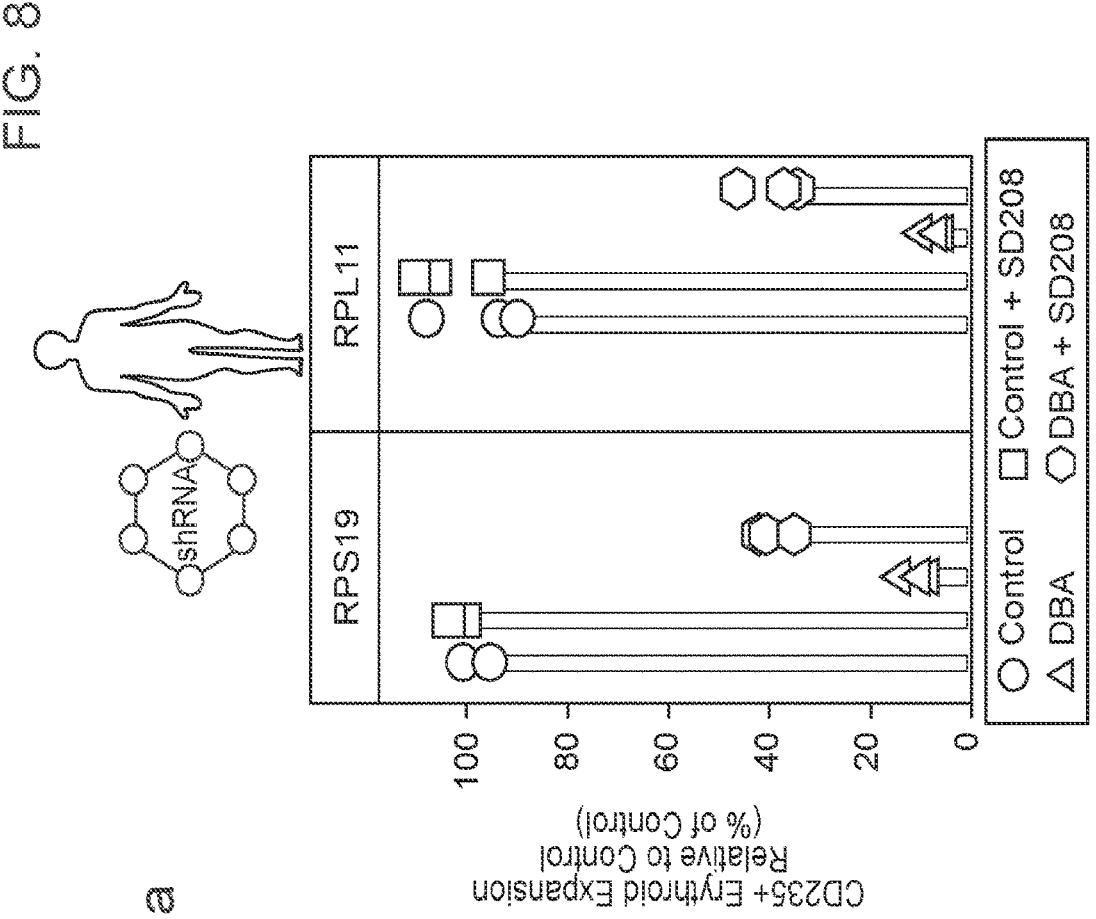
FIG. 8. NLK inhibition increases expansion of erythroid progenitors from human and murine models of DBA. Human cord blood CD34+ progenitors were transduced with lentivirus co-expressing GFP with shRNA against luciferase (shLuc), RPS19 (shRPS19) or RPL11 (shRPL11). After 36 hours cells GFP+ cells were differentiated in erythroid media in the presence or absence of 5 µM SD208 for 15 days. Cells were counted and assessed for cell surface expression of CD235. (a) The percentage of CD235+ cells was multiplied by the cell count and values were compared as a percentage of untreated controls. (b) Normalizing values relative to untreated RPS19-insufficiency progenitors facilitates direct comparison of erythropoiesis between untreated and SD208-treated cultures. (c) Approximately 3000 cells were removed from differentiating treatments at day 6 and NLK activity was assessed. Values were normalized to reflect a fold induction relative to untreated controls. (d) Lin-Kit+ hematopoietic progenitors were obtained from three mouse embryos expressing tetracycline-inducible shRNA against RPS19 at day E14.5 or three untreated mice, and thee mature RPL11$^{+/+}$ or three mature RPL11$^{+/lox}$ mice treated with tamoxifen for eight weeks. Cells were grown in the presence or absence of doxycycline and/or SD208 for eight days prior to counting and assessing for ter119 surface expression. Values were expressed as a percentage relative to untreated controls (e) and directly comparing the effect of SD208 on erythropoiesis in ribosomal-insufficiency by expressing values relative to untreated ribosome-insufficient cultures (f). At day 5 approximately 3000 cells were assayed for NLK kinase assay (g). CD34+ HSPCs were isolated from three healthy control and three DBA patient mononuclear bone marrow aspirates by magnetic bead sorting and differentiated in the presence or absence of SD208 for 14 days. After counting the total cell population, the ratio of CD235+ erythroblasts was determined by flow cytometry and number of CD235+ erythroblasts calculated. This was expressed as a percentage of the average number of erythroid cells present in untreated healthy controls. (h) The direct effect of SD208 on erythroid expansion in DBA patient samples was calculated following normalization of untreated DBA patient samples as 1-fold, (i) At day five, 3000 cells from each of the differentiating cultures was analyzed for NLK activity by kinase assay and are expressed as a fold induction relative to untreated healthy controls.
Figure 8:
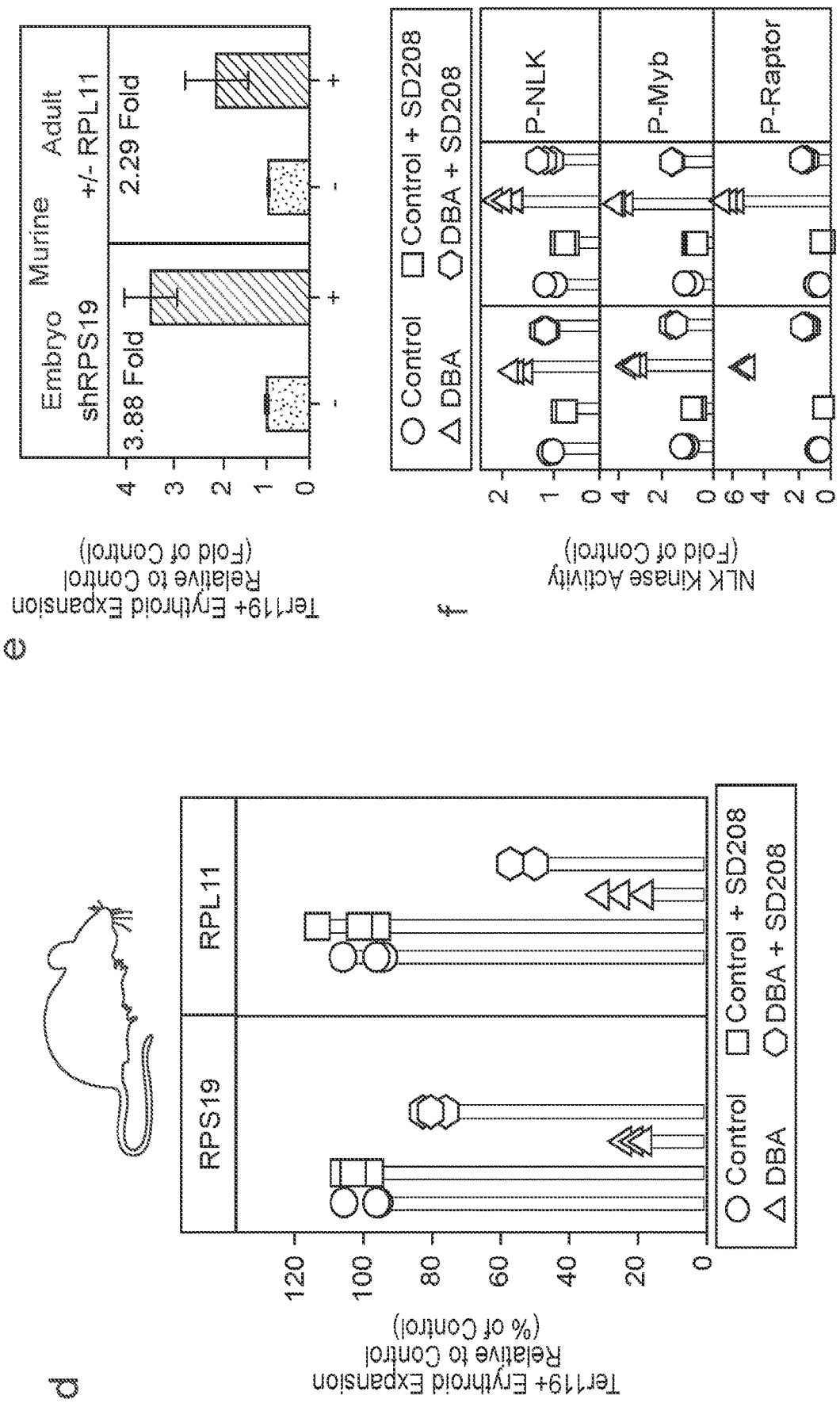
Figure 8:
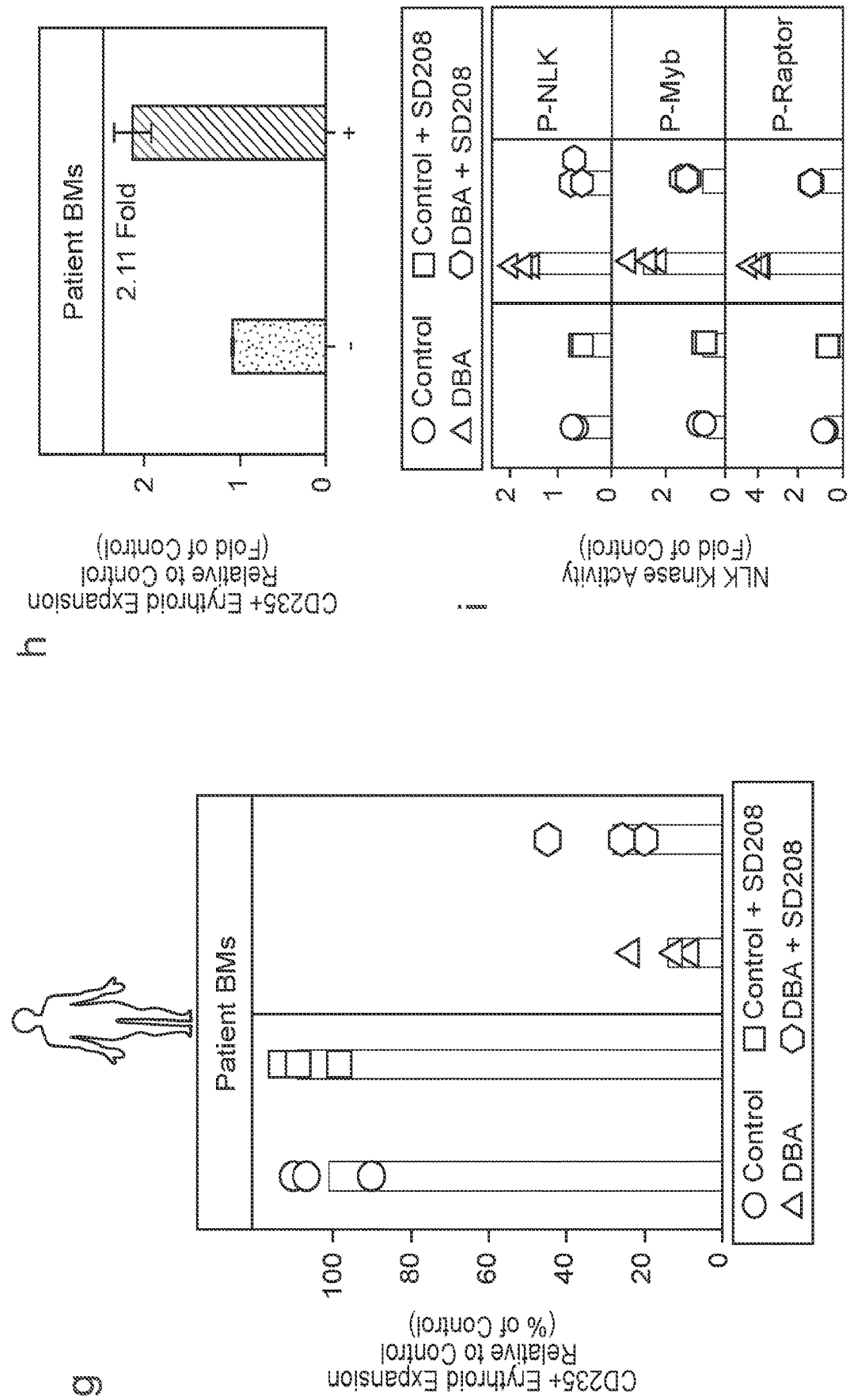

10. Pharmacological Inhibition of NLK Enhanced Erythropoiesis in Human and Murine Models of DBA NLK is activated in hematopoietic cells from RPS19- and RPL11-insufficient mice (FIG. 1, panel c) and SD208 and SB431542 improved erythropoiesis in RPS19-insufficient murine hematopoietic progenitors (FIG. 7). For direct comparison of the effects of SD208 on erythropoiesis between murine and human DBA models as well as from healthy and DBA patients, we isolated CD34+ (human) and Lin-Kit+ (murine) HSPCs from control and disease states and differentiated them in erythroid media in the presence or absence SD208 at 5 μM. SD208 did not significantly impact erythroid expansion of human CB CD34+ HSPCs transduced with control shRNA (100% to approximately 105%), however SD208 increased erythroid expansion in both RPS19- and RPL11-insufficiency from 8.7% to 38.7% and 5.8% to 36.7% respectively (FIG. 8, panel a). This increase represents a 4.7-fold increase in RPS19-insufficiency and 6.9-fold increase in RPL11-insufficiency in response to SD208 (FIG. 8, panel b). As seen in FIG. 1, NLK activity was elevated in both RPS19-(an average of 3.5-fold for NLK, 5.2-fold for Myb and 8.4-fold for raptor) and RPL11-insufficient cells (an average of 3.0-fold for NLK, 4.6-fold for Myb and 7.3-fold for raptor). This was reduced in the presence of SD208 (an average of 1.2-fold for NLK, 1.5-fold for Myb and 1.7-fold for raptor in RPS19-insufficiency and 1.2-fold for NLK, 1.38-fold for Myb and 1.6-fold for raptor in RPL11-insufficiency). A decrease in NLK activity (between 10 and 30%) was also observed in controls, suggesting a low basal activity is retained during normal differentiation (FIG. 8, panel c).

In mice, Lin-Kit+ cells include the hematopoietic stem and progenitor cells and are abundant in the fetal liver[35]. We purified murine HSPCs from the fetal liver of three mice encoding a tetracycline-inducible shRNA against RPS19 and differentiated them for 8 days in erythroid media in the absence or presence of doxycycline and/or SD208. Induction of RPS19-insufficiency in the absence of SD208 reduced Ter119+ erythroblasts to 24.3%, 20.3% and 18.5% of populations differentiated in the absence of doxycycline. The presence of SD208 with doxycycline improved erythropoiesis to 83.2%, 81.1% and 76.6% (FIG. 8, panel c—left portion).

Lin-Kit+ HSPCs are most abundant in the bone marrow of mature mice[51]. Three mature RPL11$^{+/lox}$ mice were treated with tamoxifen for eight weeks to induce heterozygous deletion of RPL11. As controls, three RPL11$^{+/+}$ littermate mice of the same strain were treated with tamoxifen. Lin-Kit+ HSPCs were isolated from the bone marrow and differentiated in erythroid media in the presence or absence of SD208 for 8 days. As observed in other DBA models, RPL11-insufficiency reduced erythropoiesis to 31.2%, 26.4% and 18.6% of controls. The presence of SD208 improved erythropoiesis to 57.3%, 56.8% and 50.3% (FIG. 8, panel d—right portion). These data represent fold increases of 3.88 in RPS19- and 2.29 in RPL11-insufficiency in response to SD208 (FIG. 8, panel e).

NLK immuno-precipitated from differentiating hematopoietic progenitors at day 5 from both RPS19- and RPL11-insufficient displayed elevated kinase activity relative to controls. NLK activity was increased (NLK phosphorylation averaged 1.9-fold, Myb phosphorylation averaged 3-fold, and raptor phosphorylation averaged 5.8-fold above controls) in doxycycline-treated tetracycline-inducible shRPS19 cultures. NLK from RPL11 heterozygous null differentiating progenitors also increased activity (average NLK phosphorylation was 2.0-fold, average Myb phosphorylation was 4.0-fold and raptor phosphorylation averaged 7.0-fold) (FIG. 8, panel f). Similar to human models, NLK activity was drastically inhibited in ribosomal insufficiency (FIG. 8, panel f). But although the absolute numbers varied, SD208 increased erythroid expansion in RPS19- and RPL11-insufficiency in both human and murine models of DBA.

11. Increased Erythropoiesis in DBA Patient HSPCs Treated with SD208

CD34+ HSPCs were isolated from mononuclear bone marrow aspirates from three healthy controls and three DBA patient bone marrow biopsies and cultured in erythroid media in the presence or absence of 5 μM SD208. In the absence of SD208, differentiation of CD235+ erythroblasts from CD34+ HPCs from DBA patients was 23.0%, 11.6% and 8.4% of healthy controls. The presence of SD208 increased this to 43.7%, 24.7% and 19.4% (FIG. 8, panel g). This correlates to a mean increase in erythroid expansion of 2.11-fold in the presence of SD208 (FIG. 8, panel h). Each of the complete DBA patient biopsy samples displayed elevated NLK activity relative to healthy controls (FIG. 1, panel a) and differentiating progenitors derived from CD34+ HSPCs similarly activated NLK. Immuno-purified NLK from differentiating cultures at day 6 phosphorylated NLK an average of 2.3-fold, c-Myb an average of 2.8-fold, and raptor an average of 4.4-fold more than NLK from healthy controls (FIG. 8, panel i). This provides proof of concept that pharmacological targeting of NLK activation improves erythropoiesis in DBA patients.

D. Results

NLK is activated in erythroid progenitors from DBA models including RP-knockdown human cord blood cells, bone marrow and iPSCs from DBA patients and mouse models, suggesting that NLK contributes to disease pathogenesis. Our results also demonstrated that NLK plays a role during normal erythropoiesis. We observed a transient increase in NLK activation in normal human erythroid progenitors during early differentiation of cord blood CD34+progenitor cells. However, the molecular mechanisms contributing to NLK hyperactivation and the pathways regulating normal and aberrant erythropoiesis are not understood.

NLK activity has been reported to suppress WNT signaling[52]. In normal human cord blood HSPCs, NLK suppresses this signal in early hematopoiesis. However, as this transient peak is less pronounced in myeloid-favoring conditions, it is likely that NLK activation is erythroid specific. During normal erythropoiesis, c-Myb expression is low, but there is a transient increase in expression during the transition between BFU-E and CFU-E stages[5]. NLK-mediated phosphorylation may aid in the rapid loss of c-Myb required to bring c-Myb levels back down. Alternatively, the BFU-E to CFU-E transition may require increased autophagy to aid organelle turnover and recycling facilitated by temporary phosphorylation of raptor by NLK. Interestingly, this transient activation is not induced in differentiating cultures derived from iPSCs.

Human cord blood CD34+ cells expressing shRNA against RPS19 and RPL11 increase NLK activity, but NLK expression is reduced relative to control cells (FIG. 1, panel b). As the kinase assays are normalized to cell number, and not NLK levels, this would indicate that NLK activity is higher than actually reflected. These cultures reflect a pool of erythroid, megakaryocyte and myeloid cells and the ratio of each cell population changes with the introduction of shRNAs against RPS19 and RPL11 (reduced erythroblasts). Differences in NLK expression in the culture therefore may not be uniform across all cell types and only reflect the changes in each cell population.

Our results demonstrated that NLK expression is significantly reduced in non-erythroid lineages. Consistent with this result, ribosomal insufficiency leads to an increased percentage of myeloid cells and a correspondingly lower level of NLK protein compared to controls. In conditions favoring megakaryocyte and myeloid differentiation, the expression of NLK is further downregulated, which supports this hypothesis. Comparison of NLK expression indicated no differences between control and RPS19-insufficient CD235+ erythroblasts, again suggesting NLK expression is not altered during erythropoiesis and the observed reductions in mixed cultures reflects NLK suppression in other lineages.

Ribosomal insufficiency in our culture system has a mild impact on megakaryocyte and other myeloid progenitors. It is possible that the bone marrow niche offers an environment that supports hematopoiesis and can buffer against milder intrinsic cellular defects. Reports of DBA patients with megakaryocyte and other myeloid anomalies are not uncommon[53], indicating manifestations of ribosomal insufficiency may occur in other hematopoietic lineages when exposed to certain cell intrinsic or environmental stress. It should be noted that manipulation of NLK did not have any impact on the mild inhibitory effects of ribosomal insufficiency on other lineages, indicating NLK inhibition probably would not be an effective therapeutic option to alleviate these non-erythroid defects.

An important erythroid transcription factor c-Myb is highly elevated in early erythropoiesis and is rapidly downregulated in both cord and peripheral blood progenitor cells[5,6]. By the polychromatic erythroblast stage, c-Myb is virtually undetectable, although, as previously discussed, a dramatic, transient elevation in c-Myb expression occurs at the BFU-E to CFU-E transition[5]. Myb serves a number of cellular roles in erythropoiesis, including transcriptional regulation of KLF1 and LMO2[43]. KLF1 expression steadily rises after early erythroid commitment but peaks between late basophilic and orthochromatic erythroblast stages[54]. LMO2 expression decreases between MEP and BFU-E stages, but then increases to the late basophilic stage before dramatic downregulation and is almost undetectable by orthochromatic erythroblast stage[5]. In this way, deregulation of c-Myb during early erythropoiesis by NLK phosphorylation likely manifests influence on red blood cell production through later stages of differentiation. Intriguingly, the ubiquitin ligase that degrades NLK-phosphorylated c-Myb, Fbxw7[55] is highly expressed in hematopoietic cells[56,57] and contributes to GATA2/GATA1 switching in erythropoiesis[58], perhaps contributing to the erythroid-specific effects observed in ribosomal insufficiencies.

The stabilization of p53 has been documented as critical in the pathogenesis of DBA[1,37]. NLK activation during RPS19-insufficiency requires p53, as no NLK activation was observed when shRNA against p53 was expressed. It is unclear if NLK activation in RP-insufficiency requires only p53 or a p53-independent component is also required. NLK has also been reported to stabilize p53 independently of kinase activity[59]. It is possible NLK contributes to DBA pathogenesis through a feed-forward loop with both kinase-dependent and -independent mechanisms. As NLK expression is normally restricted to erythroid progenitors, this is an intriguing possibility.

Autophagy is an intracellular degradative process that occurs both constitutively, to clear damaged organelles, recycle long-lived proteins during normal homeostasis, and can be induced in response to nutrient starvation, hypoxia, growth factors and energy depletion[48] for cell maintenance or contribute to cell death[60,61]. The process involves the formation of double-membrane vesicles, called autophagosomes in which autophagy related proteins (ATGs) assemble to conjugate the inactive light chain protein 3 (LC3-I) to phosphatidylethanolamine. This generates the active, lipidated form (LC3-II), which are inserted into autophagosome membranes[62]. In normal erythropoiesis, one, or a few large autophagosome/endosome structures develop and this correlates with contraction of lysosomes during the polychromatic erythroid stage, however autophagosomes remain abundant until enucleation[10,63]. Expression profiling during erythropoiesis reveals upregulation of autophagy-regulating genes including ATG8 and ATG4 family genes[10] MATOR1, MATOR5, HMOX1, TOLLIP and ATP6VOE1 occurring between late basophilic and orthochromatic erythroid stages[5].

A key modulator of autophagy is the serine/threonine kinase mammalian Target of Rapamycin (mTOR). This kinase can exist within two functionally distinct complexes recognized as mTOR-Complex 1 (mTORC1) and mTOR-Complex 2 (mTORC2) and the two are distinguished by the presence of raptor (mTORC1) or rictor (mTORC2) within the complex. Only mTORC1 can directly regulate autophagy[48]. Autophagy events independent of mTOR exist[64] although our understanding of these events in erythropoiesis is unknown and may, or may not, be influenced by NLK. Apart from autophagy, many other cellular functions are regulated by mTORC1 and are likely to be impacted from NLK-mediated raptor phosphorylation and should be investigated.

Despite differences in mechanisms regulating erythroid production in humans and mice, DBA-like phenotypes are observed in both species in response to ribosomal insufficiency[35,36], suggesting a conserved molecular mechanism. Interestingly, the magnitude of rescue in the adult RPL11$^{+/lox}$ murine model more closely resembled patient-derived progenitors compared to the embryonic RPS19 shRNA model (FIG. 8). Whether this similarity reflects the specificity of ribosomal defects in DBA is an intriguing possibility. Our data demonstrate that small molecules are capable of inhibiting NLK activity. Our observation that NLK activation is conserved and contributes to erythroid defects highlights the relevance of using these model systems to study DBA and developing novel approaches to target NLK in the future.

E. Materials and Methods

1. Cell Culture

Primary human CD34$^+$ hematopoietic stem and progenitor cells were purified from cord or peripheral blood (New York Blood Center) or from human fetal liver tissue (Advanced Bioscience Resources and University of California, Los Angeles Center for AIDS Research) by using magnetic-activated cell sorting (Miltenyi Biotec) and were cryopreserved. Upon thawing, cells were cultured in x-Vivo15 media (Lonza) containing 10% fetal bovine serum, fms-related tyrosine kinase 3 (50 ng/mL), thyroid peroxidase (50 ng/mL), interleukin-3 (IL-3; 20 ng/ml), interleukin-6 (IL-6; 20 ng/ml), and stem cell factor (50 ng/ml). When applied, TGFβ1 was added at 5 ng/ml. Kp53A1 cells were obtained from Javier Leon and cultured in DMEM supplemented with 10% fetal bovine serum at 37 or 32° C. Stable cell lines expressing shRNA against RPS19 with differing efficiencies; shRPS19 #8 (high), shRPS19 #1 (moderate), and shRPS19 #3 (low) were generated by co-transfecting shRNA-carrying vectors (pLVTH) with neomycin-carrying vector (pcDNA3.1) using Lipofectamine® 2000 (Thermo Fisher). Individual clones were harvested and expanded in 100 μg/ml neomycin and RPS19 expression examined by Western blot and qRT-PCR. CD34+ progenitors were obtained from mononuclear bone marrow DBA patient samples using magnetic-activated cell sorting (Miltenyi Biotec) and differentiated for 12 days.

2. Lentiviral Transduction

Primary CD34$^+$ cells were transduced as published[30] with lentivirus expressing shRNA against RPS19, RPL11, p53 or luciferase (Luc), siRNA against NLK or a non-targeting (NT) sequence, or cDNA expressing NLK with wild type 3'UTR, a mutated 3'UTR or no 3'UTR or "escape" NLK. Virus co-expressed GFP, RFP, mCherry or puromycin to enable selection.

3. Compounds

Small molecule inhibitors were purchased from Selleck-Chem, with the exception of SD208 (Tocris), ITD-1 (Adooq Bioscience) and were diluted in dimethylsulfoxide (DMSO). The RSK inhibitor BI-D1870 was synthesized by Samanta Capolicchio. Inhibitors were added to cells at indicated concentrations with a final DMSO concentration of 0.5%. Staurosporine, lactacystin and chloroquine were purchased from Sigma Aldrich and diluted according to manufacturer's instructions, and added to cells at a concentration of 1 µM, 10 µM and 30 µM respectively.

4. Colony Assays

Sorted hematopoietic cells were seeded in methylcellulose medium containing IL-3, stem cell factor, granulocyte macrophage colony-stimulating factor, and erythropoietin (H4434; STEMCELL Technologies) in triplicate, with 1000 cells per plate. Erythroid (burst-forming unit erythroid) and myeloid (colony-forming unit, granulocyte-macrophage) colonies were counted 14-18 days later. In some cases, 3000 (shRPL11) or 5000 (shRPS19+TGFβ) cells per plate were added to ensure enough colonies for robust statistical analysis.

5. Flow Cytometry

For cell surface flow cytometry, cells were incubated with human Fc receptor binding inhibitor (#14-9161-73; eBioscience, Inc.) followed by primary antibodies CD235-APC (#306607; BioLegend) CD41-FITC (#303703; BioLegend) and CD11b-PE/Cy5 (#101209; BioLegend). Data were collected on a DxP10 flow cytometer (Cytek) and analyzed by using FlowJo Software, v.9.7.2.

6. Kinase and Ubiquitin Assays

For NLK kinase analysis, cultures were treated as indicated and lysed for 30 min at 4° C. in 750 µl of kinase lysis buffer (50 mM Tris [pH 7.4], 5 mM EDTA, 250 mM NaCl, 0.1% Triton X-100, 50 mM NaF, 0.1 trypsin inhibitor unit of aprotinin per ml, 50 µg of phenylmethylsulfonyl fluoride per ml, 100 µM sodium vanadate, 1 µg of leupeptin per ml). For TGFβR1 kinase analysis, cells were lysed in membrane kinase buffer (10 mM Tris-HCl (pH8.0), 140 mM NaCl, 300 mM KCl, 0.5% Triton X-100 and 0.5% sodium deoxycholate with complete protease inhibitor cocktail (Roche)). Extracts were clarified, and equivalent protein was incubated overnight at 4° C. with antibody (NLK: #AB97642; Abcam, TGFβR1: V22; Santa Cruz Biotechnology). Immune complexes were collected with Catch and Release® V2.0 Reversible Immunoprecipitation System and diluted in kinase buffer (25 mM Tris [pH 7.4], 10 mM $MgCl_2$, 1 mM dithiothreitol). When cell numbers were limiting, NLK activity was amplified by adding 0.5 µg dephosphorylated NLK prior to performing kinase reaction. 50 µl of kinase buffer containing NLK or TGFβR1 sample and 5 µM ATP was incubated in the presence of biotinylated substrate (NLK, c-Myb or raptor for NLK and Smad2 or Smad3 for TGFβR1) immobilized on streptavidin-coated 96-well plates. The kinase reaction was allowed to proceed for 30 min at 37° C. before kinase was removed. After vigorous washing in kinase buffer, substrates were incubated for 60 min with antibody against phosphor-Serine/Threonine (#525280; Calbiochem), and detected by HRP-conjugated anti-mouse antibody (#170-6516; BioRad) and SuperSignal® West Pico Chemiluminescent Substrate (Thermo Scientific). Signal was detected at 428 nm by Synergy™ H1 hybrid multi-mode microplate reader (BioTek®). Prior to kinase analysis, NLK c-Myb, raptor, Smad2 and Smad3 were immunopurified by Catch and Release® V2.0 Reversible Immunoprecipitation System and biotinylated as per manufacturer's instructions (EZ Link™ NHS Biotin; Thermo Scientific) and immobilized on Pierce® NeutrAvidin-coated 96-well plates (Thermo Scientific). Background phosphorylation was removed by 30 min incubation in the presence of 0.1 unit/ml calf intestinal phosphatase (New England Biolabs). Ubiquitination assays were performed similarly to kinase assays, except lysates are added directly to immobilized substrates and substrates are interrogated with antibody against ubiquitin (#P4D1; Santa Cruz Biotechnology), rather than phosphorylation.

7. qRT-PCR

RNA was extracted by using total RNA mini kit (Bio-Rad). RNA was transcribed into cDNA by using the iScript cDNA Synthesis Kit (Bio-Rad). The quantitative RT-PCR (qRT-PCR) reaction was run with iQ SYBR Green MasterMix (Bio-Rad) using the CFX384 Touch Real-Time PCR Detection System (Bio-Rad). 7SL small cytoplasmic RNA14 was used as an internal control. miRNA was quantified using TaqMan® Small RNA Assays (Applied Biosystems) as per manufacturer's directions and normalized to snoRNA. Fold change of mRNA and miRNA was calculated by using the comparative Ct method.

8. Luciferase Assay

The NLK minimal promoter (1019 5'nucleotides) and NLK 3'UTR (1885 3' nucleotides) were cloned upstream, or downstream respectively, of firefly luciferase in pLenti-GIII-CMV-RFP-2A-Puro (abm). Transduced into CD34+ cord blood progenitors were differentiated in 1 µg/ml puromycin for 6 days. Transduction efficiency was normalized by RFP expression and firefly luciferase activity determined by Luciferase Assay Reagent II (LAR II) from Dual-Luciferase® Reporter (DLR™) Assay System (Promega). Luminescence was assessed using a Synergy™ H1 hybrid multi-mode microplate reader (BioTek®).

9. Immunoprecipitation and Blotting

Antibodies against RPS19 (#AB40833; Abcam; 1:200 dilution), NLK (#AB97642; Abcam; 1:1000 dilution) c-Myb (#12319; Cell Signaling; 1;1000 dilution), raptor (#AB26264; Abcam 1;1000 dilution), phosphor-Serine (#525280; Calbiochem; 1:1000 dilution), S6K (#9202; Cell Signaling; 1:500 dilution), and 4E-BP1 (#9452; Cell Signaling; 1:500 dilution), and GAPDH (#MAB374; Millipore; 1:10000) were used according to manufacturer's instructions. The target proteins were analyzed by using SuperSignal® West Pico Chemiluminescent Substrate for horseradish peroxidase (Thermo Scientific). Densitometry was performed using Image J software (http://rsb.info.nih.gov/ij/). When indicated, proteins were co-immunoprecipitated prior to immunoblotting. Cell lysates were normalized for protein before preclearing with Protein A/G Agarose (Upstate) for 30 min, before incubating with indicated antibody overnight. Immune complexes were precipitated with Protein A/G Agarose and separated by SDS-PAGE, before being subjected to immunoblotting.

10. Immunofluorescent Confocal Microscopy

At the conclusion of the experiment, cells were washed twice in DME pH2.0, twice in DME pH7.0 and twice in cold PBS before fixation with 4% paraformaldehyde at Room Temperature for 20 min and permeabilization for 3 min with 0.1% Triton X100. After 60 min blocking (0.05% Saponin (Sigma-Aldrich, St Louis, Missouri)/2% FBS in PBS) cells were incubated with antibodies recognizing lysosome-specific LAMP1-FITC (#130-102-191; MiltenyiBiotec; mouse) and raptor ((#AB26264; Abcam; rabbit), followed by Cy3-conjugated antibody against rabbit (#AP132C; EMD Millipore; goat) and 3 minute incubation with DAPI. Slides were mounted using Vectashield (Vector Laboratories, Cambridgeshire, UK) and confocal images were acquired on an inverted Zeiss LSM multiphoton laser scanning confocal microscope. No three-dimensional reconstructions, surface or volume rendering, or gamma adjustments were performed and only results are included that could be validated by a minimum of three repeats with the majority of cells on the slide sharing the reported phenotype. Where possible, multiple cells showing the observed phenotype are displayed in each field.

11. Autophagy

Autophagy was detected using the Autophagy Assay Kit (Sigma Aldrich) as per manufacturer's instructions. Briefly, cells were incubated in the presence of autophagosome detection reagent for 45 min at 37° C. in 5% $CO_2$, followed by 4 vigorous washes. Fluorescence intensity was detected ($\lambda_{ex}$=360/$\lambda_{em}$=520 nm) by flow cytometer, plate reader and Leica DM IRBE inverted microscope using the DAPI channel. The number of puncta in 100 cells was scored and averaged. Experiments were performed in triplicate.

12 Mice

The RPS19-deficient mouse model contains a doxycycline-regulatable Rps19-targeting shRNA (shRNA-D) located downstream of the collagen A1 locus, allowing dose-dependent downregulation of Rps19 expression (PMID: 21435508). Mice were maintained at the Lund University animal facility (Sweden) and all animal experiments were performed with consent from the Lund University animal ethics committee.

Inducible RPL11 heterozygous deletion mice[36] were fed a standard chow diet ad libitum. When indicated, standard chow diet was replaced by tamoxifen diet (Teklad, Harlan Laboratories) to induce activation of the CreERT2 transgene. All animals were maintained at the Spanish National Cancer Research Centre (CNIO) under specific pathogen-free conditions, in agreement with the recommendations of the Federation of European Laboratory Animal Science Association (FELASA). All animal procedures were evaluated and approved by the Ethical Committee of the Carlos III Health Institute, Madrid, Spain (#54-2013-v2).

13. Cloning and CRISPR/Cas9

Generation of lentiviral constructs expressing NLK cDNA, NLK cDNA with various 3'UTR mutants, and NLK with an alternative nucleotide sequence at the siRNA targeting site (escape NLK), as well as luciferase gene fused to the NLK 5' or 3' UTR, were generated with standard molecular biology techniques. For CRISPR-Cas9 disruption of the miR181-binding sequence within the NLK 3'UTR, a series of sgRNAs were purchased from Synthego and screened for the ability to disrupt miR181 binding. K562 cells stably expressing luciferase fused to the NLK 3'UTR were electroporated with sgRNAs and Cas9. Cells were differentiated towards erythroid or myeloid lineages with hemin or TCA respectively. After 36 hours, luciferase activity was assessed. Control TPA-treated cells induce miR181 and have reduced luciferase activity so maintained elevated luciferase in TPA treated group indicates miR181-binding site disruption. A control sgRNA, a poor NLK-targeting sgRNA and an efficient NLK-targeting sgRNA were electroporated with Cas9 into CD34+ progenitors and transduced with shRNA against RPS19 and luciferase. After 15 days differentiation populations were counted and assessed by flow cytometry for expression of CD235, CD41a and CD11b. The indel frequency of each sorted population was determined after DNA sequencing. Designing primers and analyzing indel frequency was performed using Snap-Gene®.

14. Statistics

P values for statistical significance were obtained by using a paired Student t test. The data are representative of at least 3 independent experiments.

F. References

1 Da Costa, L., Narla, A. & Mohandas, N. An update on the pathogenesis and diagnosis of Diamond-Blackfan anemia. F1000Research 7, doi: 10.12688/f1000research.15542.1 (2018).

2 Mirabello, L. et al. Novel and known ribosomal causes of Diamond-Blackfan anaemia identified through comprehensive genomic characterisation. Journal of medical genetics 54, 417-425, doi: 10.1136/jmedgenet-2016-104346 (2017).

3 Khajuria, R. K. et al. Ribosome Levels Selectively Regulate Translation and Lineage Commitment in Human Hematopoiesis. Cell 173, 90-103.e119, doi: 10.1016/j.cell.2018.02.036 (2018).

4 Ludwig, L. S. et al. Altered translation of GATA1 in Diamond-Blackfan anemia. Nature medicine 20, 748-753, doi: 10.1038/nm.3557 (2014).

5 Yan, H. et al. Developmental differences between neonatal and adult human erythropoiesis. American journal of hematology 93, 494-503, doi: 10.1002/ajh.25015 (2018).

6 Merryweather-Clarke, A. T. et al. Distinct gene expression program dynamics during erythropoiesis from human induced pluripotent stem cells compared with adult and cord blood progenitors. BMC genomics 17, 817, doi: 10.1186/s12864-016-3134-z (2016).

7 Bengtsen, M. et al. c-Myb Binding Sites in Haematopoietic Chromatin Landscapes. PloS one 10, e0133280, doi: 10.1371/journal.pone.0133280 (2015).

8 Huang, Y., Jiang, Y., Lu, W. & Zhang, Y. Nemo-like kinase associated with proliferation and apoptosis by c-Myb degradation in breast cancer. PloS one 8, e69148, doi: 10.1371/journal.pone.0069148 (2013).

9 Sieff, C. A., Yang, J., Merida-Long, L. B. & Lodish, H. F. Pathogenesis of the erythroid failure in Diamond Blackfan anaemia. British journal of haematology 148, 611-622, doi: 10.1111/j.1365-2141.2009.07993.x (2010).

10 Betin, V. M., Singleton, B. K., Parsons, S. F., Anstee, D. J. & Lane, J. D. Autophagy facilitates organelle clearance during differentiation of human erythroblasts: evidence for a role for ATG4 paralogs during autophagosome maturation. Autophagy 9, 881-893, doi: 10.4161/auto.24172 (2013).

11 Heijnen, H. F. et al. Ribosomal protein mutations induce autophagy through S6 kinase inhibition of the insulin pathway. PLOS genetics 10, e1004371, doi: 10.1371/journal.pgen.1004371 (2014).

12 Doulatov, S. et al. Drug discovery for Diamond-Blackfan anemia using reprogrammed hematopoietic progenitors. Science translational medicine 9, doi: 10.1126/scitranslmed.aah5645 (2017).

13 Brott, B. K., Pinsky, B. A. & Erikson, R. L. Nlk is a murine protein kinase related to Erk/MAP kinases and localized in the nucleus. Proceedings of the National Academy of Sciences of the United States of America 95, 963-968 (1998).

14 Ishitani, T. & Ishitani, S. Nemo-like kinase, a multifaceted cell signaling regulator. Cellular signalling 25, 190-197, doi: 10.1016/j.cellsig.2012.09.017 (2013).

15 Lv, M. et al. Lentivirus-mediated knockdown of NLK inhibits small-cell lung cancer growth and metastasis. Drug design, development and therapy 10, 3737-3746, doi: 10.2147/dddt.S87435 (2016).

16 Kanei-Ishii, C. et al. Fbxw7 acts as an E3 ubiquitin ligase that targets c-Myb for nemo-like kinase (NLK)-induced degradation. The Journal of biological chemistry 283, 30540-30548, doi: 10.1074/jbc.M804340200 (2008).

17 Kanei-Ishii, C., Nomura, T., Tanlkawa, J., Ichikawa-Iwata, E. & Ishii, S. Differential sensitivity of v-Myb and 18 Kurahashi, T., Nomura, T., Kanei-Ishii, C., Shinkai, Y. & Ishii, S. The Wnt-NLK signaling pathway inhibits A-Myb activity by inhibiting the association with coactivator CBP and methylating histone H3. Molecular biology of the cell 16, 4705-4713, doi: 10.1091/mbc.e05-05-0470 (2005).
19 Yuan, H. X. et al. NLK phosphorylates Raptor to mediate stress-induced mTORC1 inhibition. Genes & development 29, 2362-2376, doi: 10.1101/gad.265116.115 (2015).
20 Zhang, Z. Y. et al. Stabilization of ATF5 by TAK1-Nemo-like kinase critically regulates the interleukin-1beta-stimulated C/EBP signaling pathway. Molecular and cellular biology 35, 778-788, doi: 10.1128/mcb.01228-14 (2015).
21 Kim, S., Kim, Y., Lee, J. & Chung, J. Regulation of FOXO1 by TAK1-Nemo-like kinase pathway. The Journal of biological chemistry 285, 8122-8129, doi: 10.1074/jbc.M110.101824 (2010).
22 Ota, S. et al. NLK positively regulates Wnt/beta-catenin signalling by phosphorylating LEF1 in neural progenitor cells. The EMBO journal 31, 1904-1915, doi: 10.1038/emboj.2012.46 (2012).
23 Masoumi, K. C. et al. NLK-mediated phosphorylation of HDAC1 negatively regulates Wnt signaling. Molecular biology of the cell 28, 346-355, doi: 10.1091/mbc.E16-07-0547 (2017).
24 Yan, X. et al. Impact of miR-208 and its Target Gene Nemo-Like Kinase on the Protective Effect of Ginsenoside Rb1 in Hypoxia/Ischemia Injured Cardiomyocytes. Cellular physiology and biochemistry: international journal of experimental cellular physiology, biochemistry, and pharmacology 39, 1187-1195, doi: 10.1159/000447825 (2016).
25 Cichocki, F. et al. Cutting edge: microRNA-181 promotes human NK cell development by regulating Notch signaling. Journal of immunology (Baltimore, Md.: 1950) 187, 6171-6175, doi: 10.4049/jimmunol.1100835 (2011).
26 Ji, J. et al. Identification of microRNA-181 by genome-wide screening as a critical player in EpCAM-positive hepatic cancer stem cells. Hepatology (Baltimore, Md.) 50, 472-480, doi: 10.1002/hep.22989 (2009).
27 Kanei-Ishii, C. et al. Wnt-1 signal induces phosphorylation and degradation of c-Myb protein via TAK1, HIPK2, and NLK. Genes & development 18, 816-829, doi: 10.1101/gad.1170604 (2004).
28 Ishitani, S., Inaba, K., Matsumoto, K. & Ishitani, T. Homodimerization of Nemo-like kinase is essential for activation and nuclear localization. Molecular biology of the cell 22, 266-277, doi: 10.1091/mbc.E10-07-0605 (2011).
29 Roca, H., Varsos, Z. S. & Pienta, K. J. CCL2 is a negative regulator of AMP-activated protein kinase to sustain mTOR complex-1 activation, survivin expression, and cell survival in human prostate cancer PC3 cells. Neoplasia (New York, N.Y.) 11, 1309-1317 (2009).
30 Bibikova, E. et al. TNF-mediated inflammation represses GATA1 and activates p38 MAP kinase in RPS19-deficient hematopoietic progenitors. Blood 124, 3791-3798, doi: 10.1182/blood-2014-06-584656 (2014).
31 Flygare, J. et al. Deficiency of ribosomal protein S19 in CD34+ cells generated by siRNA blocks erythroid development and mimics defects seen in Diamond-Blackfan anemia. Blood 105, 4627-4634, doi: 10.1182/blood-2004-08-3115 (2005).
32 Miyake, K. et al. Development of cellular models for ribosomal protein S19 (RPS19)-deficient diamond-blackfan anemia using inducible expression of siRNA against RPS19. Molecular therapy: the journal of the American Society of Gene Therapy 11, 627-637, doi: 10.1016/j.ymthe.2004.12.001 (2005).
33 Matsumoto, K. et al. Stepwise development of hematopoietic stem cells from embryonic stem cells. PloS one 4, e4820, doi: 10.1371/journal.pone.0004820 (2009).
34 An, X. et al. Global transcriptome analyses of human and murine terminal erythroid differentiation. Blood 123, 3466-3477, doi: 10.1182/blood-2014-01-548305 (2014).
35 Jaako, P. et al. Mice with ribosomal protein S19 deficiency develop bone marrow failure and symptoms like patients with Diamond-Blackfan anemia. Blood 118, 6087-6096, doi: 10.1182/blood-2011-08-371963 (2011).
36 Morgado-Palacin, L. et al. Partial Loss of Rpl11 in Adult Mice Recapitulates Diamond-Blackfan Anemia and Promotes Lymphomagenesis. Cell reports 13, 712-722, doi: 10.1016/j.celrep.2015.09.038 (2015).
37 Dutt, S. et al. Haploinsufficiency for ribosomal protein genes causes selective activation of p53 in human erythroid progenitor cells. Blood 117, 2567-2576, doi: 10.1182/blood-2010-07-295238 (2011).
38 Li, X. et al. MiR-181 mediates cell differentiation by interrupting the Lin28 and let-7 feedback circuit. Cell death and differentiation 19, 378-386, doi: 10.1038/cdd.2011.127 (2012).
39 Weng, H., Lal, K., Yang, F. F. & Chen, J. The pathological role and prognostic impact of miR-181 in acute myeloid leukemia. Cancer genetics 208, 225-229, doi: 10.1016/j.cancergen.2014.12.006 (2015).
40 Su, R. et al. MiR-181 family: regulators of myeloid differentiation and acute myeloid leukemia as well as potential therapeutic targets. Oncogene 34, 3226-3239, doi: 10.1038/onc.2014.274 (2015).
41 Zimmerman, E. I. et al. Lyn kinase-dependent regulation of miR181 and myeloid cell leukemia-1 expression: implications for drug resistance in myelogenous leukemia. Molecular pharmacology 78, 811-817, doi: 10.1124/mol.110.066258 (2010).
42 Bianchi, E. et al. MYB controls erythroid versus megakaryocyte lineage fate decision through the miR-486-3p-mediated downregulation of MAF. Cell death and differentiation 22, 1906-1921, doi: 10.1038/cdd.2015.30 (2015).
43 Bianchi, E. et al. c-myb supports erythropoiesis through the transactivation of KLF1 and LMO2 expression. Blood 116, e99-110, doi: 10.1182/blood-2009-08-238311 (2010).
44 Gazda, H. T. & Sieff, C. A. Recent insights into the pathogenesis of Diamond-Blackfan anaemia. British journal of haematology 135, 149-157, doi: 10.1111/j.1365-2141.2006.06268.x (2006).
45 Ceballos, E. et al. c-Myc antagonizes the effect of p53 on apoptosis and p21WAF1 transactivation in K562 leukemia cells. Oncogene 19, 2194-2204, doi: 10.1038/sj.onc.1203541 (2000).
46 Payne, E. M. et al. L-Leucine improves the anemia and developmental defects associated with Diamond-Blackfan anemia and del (5q) MDS by activating the mTOR pathway. Blood 120, 2214-2224, doi: 10.1182/blood-2011-10-382986 (2012).

47 Taylor, A. M. & Zon, L. I. Modeling Diamond Blackfan anemia in the zebrafish. Seminars in hematology 48, 81-88, doi: 10.1053/j.seminhematol.2011.02.002 (2011).
48 Paquette, M., El-Houjeiri, L. & Pause, A. mTOR Pathways in Cancer and Autophagy. Cancers 10, doi: 10.3390/cancers10010018 (2018).
49 Mortensen, M. et al. Loss of autophagy in erythroid cells leads to defective removal of mitochondria and severe anemia in vivo. Proceedings of the National Academy of Sciences of the United States of America 107, 832-837, doi: 10.1073/pnas.0913170107 (2010).
50 Moses, H. L., Roberts, A. B. & Derynck, R. The Discovery and Early Days of TGF-beta: A Historical Perspective. Cold Spring Harbor perspectives in biology 8, doi: 10.1101/cshperspect.a021865 (2016).
51 Parekh, C. & Crooks, G. M. Critical differences in hematopoiesis and lymphoid development between humans and mice. Journal of clinical immunology 33, 711-715, doi: 10.1007/s10875-012-9844-3 (2013).
52 Luis, T. C., Ichii, M., Brugman, M. H., Kincade, P. & Staal, F. J. Wnt signaling strength regulates normal hematopoiesis and its deregulation is involved in leukemia development. Leukemia 26, 414-421, doi: 10.1038/leu.2011.387 (2012).
53 Da Costa, L. et al. Diamond-Blackfan anemia, ribosome and erythropoiesis. Transfusion clinique et biologique: journal de la Societe francaise de transfusion sanguine 17, 112-119, doi: 10.1016/j.tracli.2010.06.001 (2010).
54 Giampaolo, S., Wojcik, G., Klein-Hessling, S., Serfling, E. & Patra, A. K. NFAT-mediated defects in erythropoiesis cause anemia in 1I2(−/−) mice. Oncotarget 9, 9632-9644, doi: 10.18632/oncotarget.23745 (2018).
55 Kitagawa, K. et al. Fbw7 promotes ubiquitin-dependent degradation of c-Myb: involvement of GSK3-mediated phosphorylation of Thr-572 in mouse c-Myb. Oncogene 28, 2393-2405, doi: 10.1038/onc.2009.111 (2009).
56 Thompson, B. J. et al. Control of hematopoietic stem cell quiescence by the E3 ubiquitin ligase Fbw7. The Journal of experimental medicine 205, 1395-1408, doi: 10.1084/jem.20080277 (2008).
57 Matsuoka, S. et al. Fbxw7 acts as a critical fail-safe against premature loss of hematopoietic stem cells and development of T-ALL. Genes & development 22, 986-991, doi: 10.1101/gad. 1621808 (2008).
58 Nakajima, T. et al. Regulation of GATA-binding protein 2 levels via ubiquitin-dependent degradation by Fbw7: involvement of cyclin B-cyclin-dependent kinase 1-mediated phosphorylation of THR176 in GATA-binding protein 2. The Journal of biological chemistry 290, 10368-10381, doi: 10.1074/jbc.M114.613018 (2015).
59 Zhang, H. H. et al. Nemo-like kinase is critical for p53 stabilization and function in response to DNA damage. Cell death and differentiation 21, 1656-1663, doi: 10.1038/cdd.2014.78 (2014).
60 Shimizu, S. et al. Role of Bcl-2 family proteins in a non-apoptotic programmed cell death dependent on autophagy genes. Nature cell biology 6, 1221-1228, doi: 10.1038/ncb1192 (2004).
61 Yu, L. et al. Regulation of an ATG7-beclin 1 program of autophagic cell death by caspase-8. Science (New York, N.Y.) 304, 1500-1502, doi: 10.1126/science.1096645 (2004).
62 Mizushima, N., Yoshimori, T. & Levine, B. Methods in mammalian autophagy research. Cell 140, 313-326, doi: 10.1016/j.cell.2010.01.028 (2010).
63 Griffiths, R. E. et al. The ins and outs of human reticulocyte maturation: autophagy and the endosome/exosome pathway. Autophagy 8, 1150-1151, doi: 10.4161/auto.20648 (2012).
64 Sarkar, S. Regulation of autophagy by mTOR-dependent and mTOR-independent pathways: autophagy dysfunction in neurodegenerative diseases and therapeutic application of autophagy enhancers. Biochemical Society transactions 41, 1103-1130, doi: 10.1042/bst20130134 (2013).

II. Metformin-induced suppression of Nemo-like kinase improves erythropoiesis in preclinical models of Diamond-Blackfan anemia through induction of miR-26a A. Abstract Diamond Blackfan Anemia (DBA) results from haploinsufficiency of ribosomal protein subunits in hematopoietic progenitors in the earliest stages of committed erythropoiesis. Nemo-like kinase (NLK) is chronically hyperactivated in committed erythroid progenitors and precursors in multiple human and murine models of DBA. Inhibition of NLK activity, or suppression of NLK expression, both improve erythroid expansion in these models. Metformin is a well-tolerated drug for type 2 diabetes mellitus with multiple cellular targets. Here we demonstrate that metformin improves erythropoiesis in human and zebrafish models of DBA. Our data shows that the effects of metformin on erythroid proliferation and differentiation is mediated by suppression of NLK expression through induction of miR-26a, which recognizes a binding site within the NLK 3'UTR to facilitate transcript degradation. We propose that induction of miR-26a is an approach to treat DBA and could improve anemia in DBA patients without the potentially adverse side effects of metformin in a DBA patient population.

B. Introduction

Diamond Blackfan Anemia (DBA) is one of the inherited bone marrow failure syndromes and presents with a macrocytic red blood cell aplasia usually within the first year of life (1). Over 70% of patients carry genetic mutations that lead to haploinsufficiency in one of at least 22 genes encoding ribosomal proteins (2). RPS19 and RPL11 genes are commonly mutated and account for approximately 25% and 5% of cases respectively (1). Ribosomal insufficiency leads to reduced translational efficiency of a subset of mRNA transcripts, including the master erythropoiesis transcription factor GATA1 (3). Irrespective of the driving ribosomal gene mutation, ribosomal insufficiency increases p53 protein stabilization (1, 4), contributing to aberrant activation of the serine-threonine protein kinase, nemo like kinase (NLK). Suppression of NLK expression or functional activity, significantly improves expansion of DBA erythroblasts in pre-clinical models, with minimal impact on other hematopoietic lineages (5).

NLK protein expression is significantly higher in erythroblasts than other hematopoietic lineages, and is not influenced by ribosome insufficiency. Rather, the increased activity in DBA is due to post-translational stimulation (5). Unlike in wild type hematopoietic lineages, NLK kinase activity increases in megakaryocyte and erythroid progenitors (MEPs) in DBA, and is maintained through the progenitor and precursor stages (5). The erythroid-specific effects of ribosome-insufficiency are partially due to the erythroid-specific expression of NLK, and may also explain why targeting NLK does not affect other lineages (5).

NLK is an orthologue of the *Drosophila* Nemo. It is an atypical member of the mitogen-activated protein kinases (MAPK) family. The kinase domain shares a high degree of sequence conservation with other MAPKs and cyclin-dependent kinases (Cdks) (6) which has hampered attempts to develop small molecules that specifically inhibit NLK. Off-target inhibition of NLK kinase activity with broad kinase inhibitors, such as SD208, have improved erythropoiesis in pre-clinical DBA models, but these compounds are not clinically useful due to low potency and poor solubility (data not shown). Therefore, alternative strategies to suppress NLK offer promise in the treatment of diseases affected by aberrant NLK activity.

Previous work has shown that NLK expression is significantly suppressed in response to a number of microRNAs (miRNAs), including miR-181 (7), miR-208 (8), miR-101 (9), miR-199 (10) and miR-221 (11). MicroRNAs are small RNAs, 21-24 base in length that are key regulators of post-transcriptional gene expression and RNA silencing. Hundreds of miRNAs have been identified with expression often highly tissue specific (12). Most miRNAs exert an inhibitory effect through binding a short 6-8 nucleotide sequence in the 3' untranslated region (3'UTR) of a target gene transcript. Binding is facilitated by the complementary seed sequence within the miRNA, which triggers recruitment of the RNA-induced silencing complex (RISC) leading to mRNA degradation (13). Often miRNAs only moderately perturb expression of the targeted transcript (13), however the significant susceptibility of NLK mRNA offers the potential to facilitate targeted regulation of NLK expression by the modulation of specific miRNAs.

One strategy to modulate miRNA function and, in turn, NLK expression could involve metformin, a synthetic analog of guanidine and approved therapeutic for type 2 diabetes. Metformin use has increased dramatically for pediatric type 2 diabetes and has been used in the adult population for many years. The drug is well tolerated and remains the mainstay of therapy along with diet and exercise (14). In addition to treatment of type 2 diabetes, metformin is effective in polycystic ovary syndrome and is being explored as an antiviral and anticancer agent in adult populations (15). Notably, although the mechanistic effect of metformin on NLK activity has not been thoroughly investigated, one study has demonstrated that metformin does suppress NLK expression in lung carcinoma models (16). Furthermore, metformin has been reported to deregulate miRNA profiles in a myriad of tissues (17). Collectively, these data led us to hypothesize that metformin may suppress NLK expression through miRNA modulation. Indeed, many of the miRNA perturbations mediated by metformin have potential clinical implications including the modulation of disease and homeostasis in healthy individuals (18-26).

Although metformin is well tolerated in a general pediatric population and the promise of NLK suppression is exciting, the mechanism of suppression is not understood and potential side-effects may adversely impact DBA patients. For example, metformin is known to reduce mTOR signaling and protein synthesis; this effect would likely be deleterious in DBA where there is already reduced translation brought about by ribosomal-insufficiency. Understanding the mechanism through which metformin suppresses NLK will facilitate design of more NLK-specific inhibitors without the potentially adverse side-effects associated with metformin.

Here we report the impact of metformin on erythroid expansion in human, murine and zebrafish DBA models and define the mechanism through which metformin suppresses NLK to mediate this effect.

C. Methods

1. Cell Culture

Human CD34+ HSPCs were purified from cord blood (New York Blood Center) using magnetic-activated cell sorting (Miltenyi Biotec) and differentiated as described previously (5). Luciferase, or luciferase fused to various permutations of the NLK 3' or 5'UTRs, were cloned in pcDNA3.1 expressing RFP and transfected into K562 or Kp53A1 cells using Lipofectamine® 2000 (Thermo Fisher).

2. Lentiviral Transduction

CD34$^+$ cells were transduced as published (27) with lentivirus expressing shRNA against RPS19, RPL11, or luciferase (Luc). Virus co-expressed GFP, RFP, mCherry or puromycin to enable selection.

3. Metformin and miRNAs

Metformin was purchased from SelleckChem and added to cells at indicated concentrations with a final DMSO concentration of 0.5%. MISSION® synthetic miRNAs, inhibitors and mimetics were purchased from Sigma Aldrich and transfected according to manufacturer's instructions.

4. Colony assays

Sorted HSPCs were seeded in cytokine-containing methylcellulose medium (H4434; STEMCELL Technologies) in triplicate, with 1000 cells per plate. Erythroid (burst-forming unit erythroid) and myeloid (colony-forming unit, granulocyte-macrophage) colonies were counted 14-18 days later.

5. Flow cytometry

Cells were incubated with human Fc receptor binding inhibitor (#14-9161-73; eBioscience) followed by primary antibodies CD235-APC (#306607; BioLegend) and CD11b-PE/Cy5 (#101209; BioLegend). Data were collected on a DxP10 flow cytometer (Cytek) and analyzed by using FlowJo Software, v.9.7.2.

6. Kinase Assays, Western Blotting

NLK kinase activity was performed as published (5). For Western blotting, antibodies against NLK (#AB97642; Abcam; 1:1000 dilution) and GAPDH (#MAB374; Millipore; 1:10000) were used according to manufacturer's instructions.

7. qRT-PCR

MessengerRNA was quantified as described (5). MicroRNA was quantified using TaqMan® Small RNA Assays (Applied Biosystems) as per manufacturer's directions and normalized to snoRNA.

8. Luciferase Assay

The NLK minimal promoter (1019 5' nucleotides) and or NLK 3'UTR (1885 3' nucleotides) were cloned upstream, or downstream respectively, of firefly luciferase and transfected into K562 cells. Transfection efficiency was normalized by RFP expression and firefly luciferase activity determined by Luciferase Assay Reagent II (LAR II) from Dual-Luciferase® Reporter (DLR™) Assay System (Promega). Luminescence was assessed using a Synergy™ H1 hybrid multi-mode microplate reader (BioTek®). Mutations and truncations in NLK 3'UTR were introduced using QuikChange® II XL Site-directed Mutagenesis (Agilent).

9. Mice

The RPS19- and RPL11-deficient mouse models have been described previously (5, 28-30). Kit progenitors were isolated from E14.5 liver cells of tet-shRPS19-expressing fetuses and differentiated in vitro in the presence or absence of doxycycline. Lin Kit+ HSPCs were isolated from femur bone marrow of inducible RPL11 heterozygous deletion adult mice. All animal experiments were performed with consent from the Lund University animal ethics committee or the Ethical Committee of the Carlos III Health Institute, Madrid, Spain (#54-2013-v2) and in agreement with the recommendations of the Federation of European Laboratory Animal Science Association (FELASA).

10. Zebrafish

Zebrafish were reared and injected with control or rps19-specific morpholino (MO) at the 1-cell stage as previously described (27), and treated with 20 mM metformin 4 to 5 hours post fertilization (hpf). At day 3, embryos were stained with o-dianizidine to detect hemoglobin. Embryos were obtained by natural spawning. UCLA Animal Committee approved the study.

11. Statistics

P values for statistical significance were obtained by using a paired Student t test. Significance was designated as $p<0.05$. The data are representative of at least 3 independent experiments. When possible, variability between replicates was normalized for by designating values of controls to 100% (or 1-fold), and comparing variables against that.

D. Results

Figure 9:
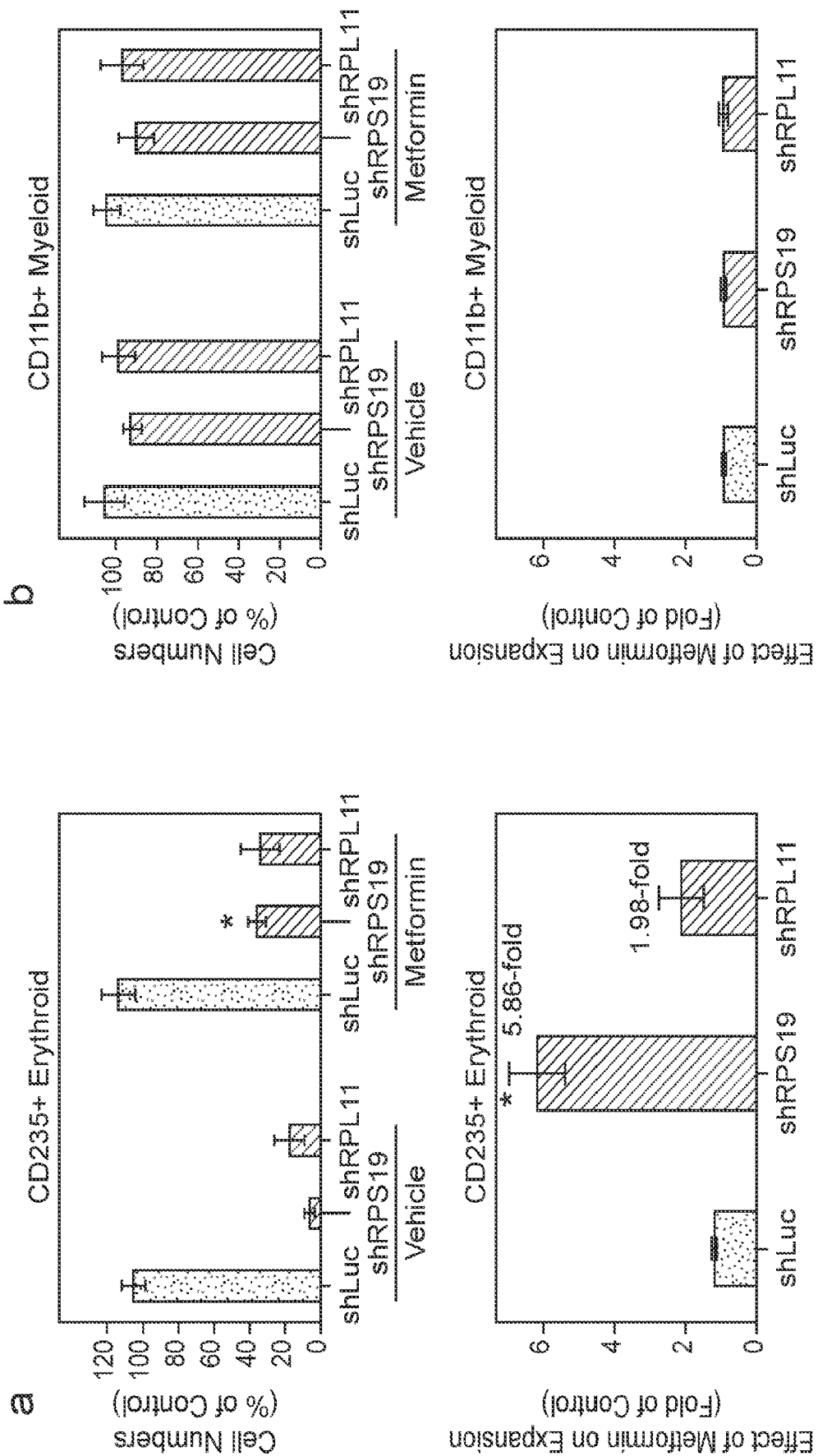
FIG. 9. Metformin improves expansion of CD235+ erythroblasts and BFU-E erythroid colony formation in human RPS19- and RPL11-insufficiency from CB CD34+ progenitors. (Panel A). CD34+ HSPCs were transduced with shRNA against control (shLuc), RPS19 (shRPS19) or RPL11 (shRPL11) and after sorting, were differentiated for 14 days in the presence or absence of 50 mM metformin. Cells were counted and the percentage expressing CD235+ erythroid (left) and CD11b+ myeloid (right) was determined by flow cytometry. Obtained values were multiplied to give an overall number that was normalized to the untreated control (grey columns). Values are presented as a percentage of the untreated control. (Panel B) Direct comparison between metformin treated and untreated cultures is facilitated by normalizing the metformin-treated values to the untreated values in control, RPS19- and RPL11-insufficient groups. Values are expressed as a fold induction relative to untreated. (Panel C) Transduced and sorted CD34+ progenitors were cultured in methylcellulose in the presence or absence of metformin for 16 days and BFU-E erythroid (left) and CFU-GM myeloid (right) colonies scored. Values are represented as the percentage of colonies induced in untreated controls (grey columns). (Panel D). To directly compare the effect of metformin in each group, metformin-treated cultures were normalized to untreated cultures and are expressed as a fold induction of the untreated control. (Panel E) Representative images of BFU-E colonies at day 14.Scale bar=200 µM. Data are displayed as means+/−SD. Statistics: two-tailed Student's t test, significant *P<0.05
Figure 9:
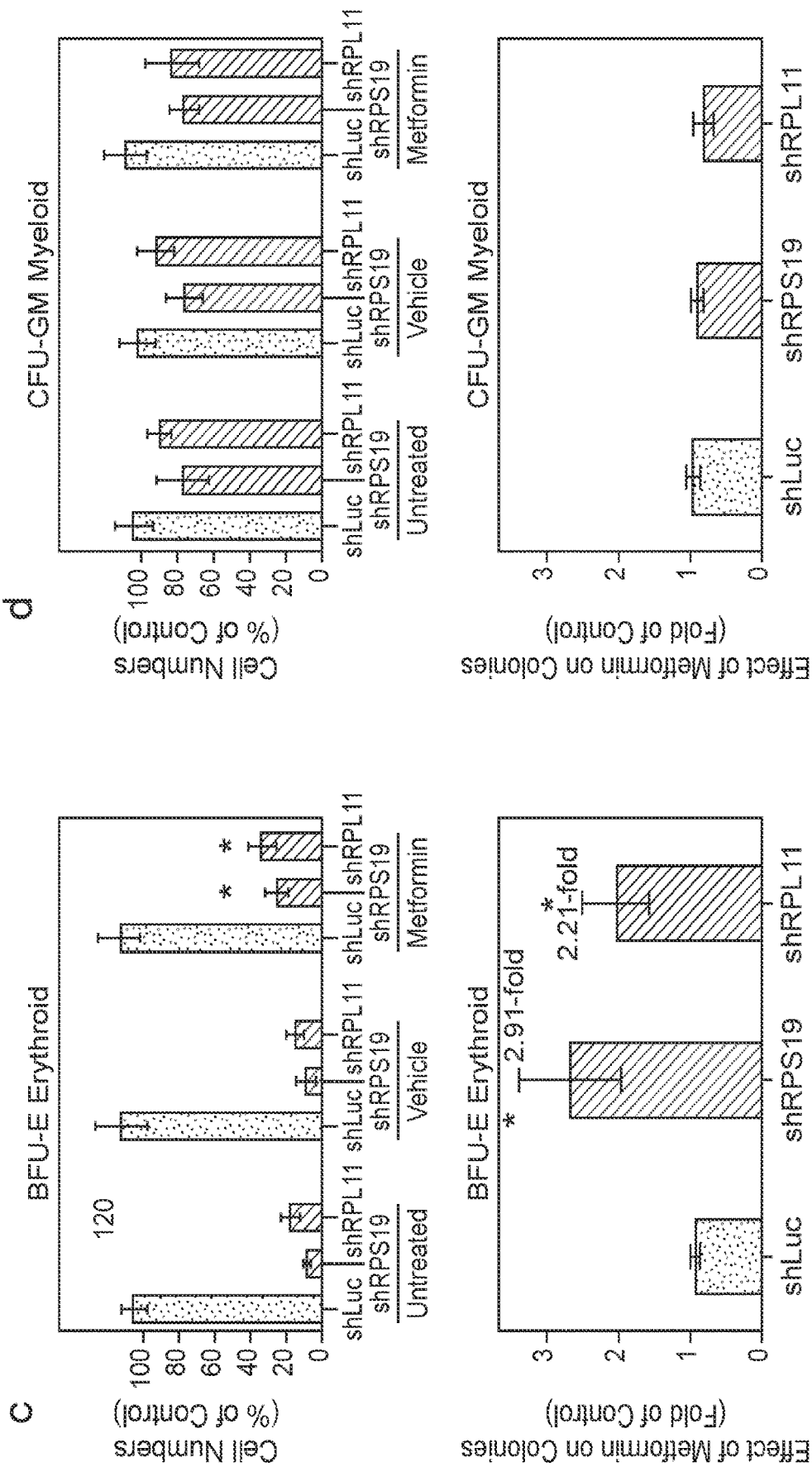
Figure 9:
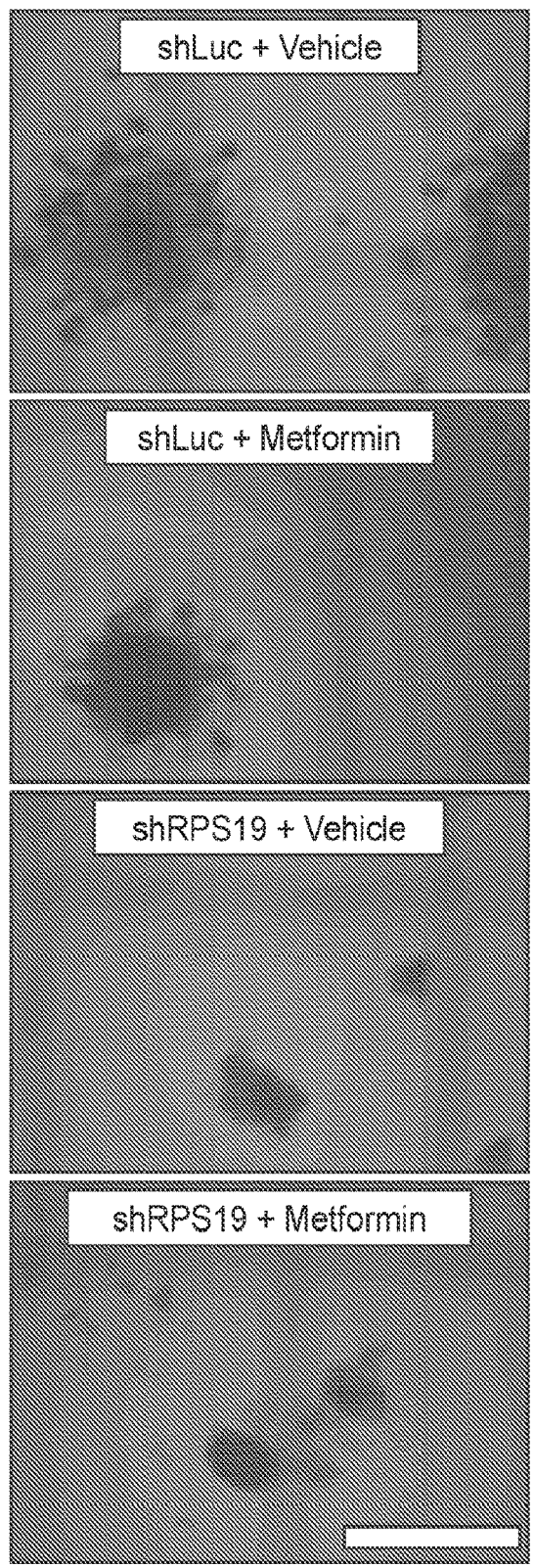

1. Metformin Suppresses NLK Expression Leading to Improved Erythropoiesis in Human Models of Diamond Blackfan Anemia Transduction of shRNA against RPS19 and RPL11 into CD34+ HSPCs have been demonstrated to induce erythroid defects as a model of DBA (27, 31, 32). CD235+ erythroid progenitors are reduced to 5.7% (p=0.0004) of control in RPS19-insufficiency and 16.4% (p=0.0032) in RPL11-insufficiency when expanded in erythroid liquid culture (FIG. 9A upper). A mild reduction in the non-erythroid CD11b+ myeloid population occurs (13% (p=0.0436) and 7% (p=0.2758) reduction in RPS19- and RPL11-insufficiency respectively) (FIG. 9B upper). When cultured in the presence of 50 mM metformin, CD235+ erythroid expansion increased from 5.7% to 33.3% (p=0.0008) and 16.4% to 32.7% (p=0.0951), which constituted an increase of 5.9-fold and 2.0-fold in RPS19- and RPL11-insufficiency respectively (FIG. 9A lower). The presence of metformin had a negligible influence on CD11b+expansion (FIG. 9B-lower). Metformin $EC_{50}$ was 11.4 mM and significant erythroid improvement was detected at concentrations above 8 mM.

Metformin also improved erythropoiesis in colony assays. Compared to vector control (shLuc), BFU-E erythroid colonies were increased from 7.7% to 16.3% (p=0.0292) in RPS19-insufficiency and 8.2% to 14.3% (p=0.0257) in RPL11-insufficiency (FIG. 9C upper), corresponding to 2.9- and 2.2-fold increases (FIG. 1D lower). Metformin did not affect CFU-GM colonies (FIG. 9D). RPS19-insufficient progenitors formed markedly smaller BFU-E colonies than controls. Metformin treatment appeared to only modestly improve the size of these colonies (FIG. 9E).

As metformin influences NLK in other cell systems (16), we examined NLK activity and expression in RPS19-insufficiency in the presence and absence of metformin. NLK immunoprecipitated from 5000 differentiating RPS19-insufficient progenitor cells robustly phosphorylated NLK, c-Myb and raptor in vitro (FIG. 10A). Metformin treatment reduced NLK activity from the same number of RPS19-insufficient progenitors, reducing phosphorylation of NLK, c-Myb and raptor by 48.5%, 39.8% and 40.2% respectively (FIG. 10A). SD208 is a Transforming Growth Factor-beta receptor small molecule inhibitor that inhibits NLK activity as an off-target in these cells (5). The effects of SD208 and metformin were compared. Examination of NLK expression in metformin-treated cultures revealed significantly less NLK expression, independent of RPS19 status. Metformin treatment reduced NLK protein expression by 62.6% and 65.4% in control and RPS19-insufficient cultures respectively. In contrast, SD208 did not significantly influence NLK expression (FIG. 10B).

SD208 inhibited the kinase activity of NLK (5) (FIG. 10A), but did not reduce NLK expression (FIG. 10B). We speculated that metformin reduced NLK kinase activity and improved erythropoiesis through suppression of NLK expression, rather than inhibiting the kinase activity directly. The addition of metformin to activated NLK in in vitro kinase assays did not influence NLK activity, supporting our hypothesis that reduced intracellular NLK activity is due to reduced NLK expression, rather than inhibition of kinase activity (FIG. 10C). NLK activity was robustly inhibited by SD208 (FIG. 10C). Expression of siRNA against NLK improved erythropoiesis in RPS19-insufficiency by 7.0-fold (4.9%-34.2% of control; p=<0.0001), however metformin treatment did not significantly increase CD235+ erythroblast expansion (7.0- to 7.5-fold; p=0.6284) (FIG. 10D) in control cultures. SD208 and NLK silencing similarly improve erythropoiesis in both RPS19 and RPL11-insufficient models (5). Because of this, we propose the observed effect of metformin in RPL11-insufficient cultures (FIG. 9) is also the result of NLK suppression.

Figure 11:
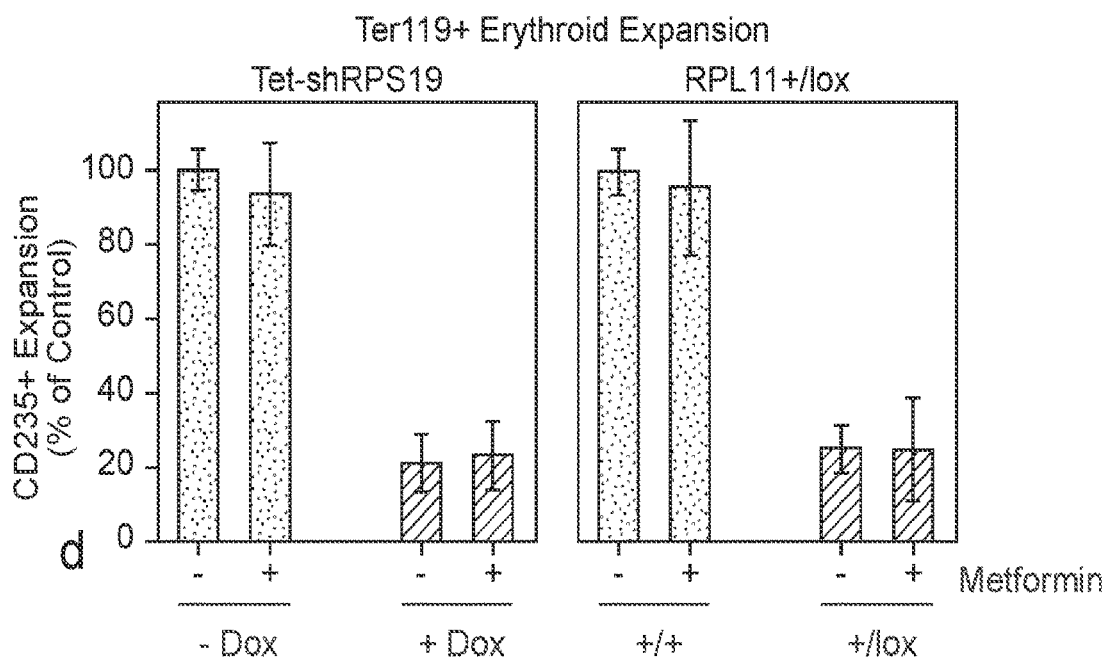
FIG. 11. Metformin improves erythropoiesis in zebrafish model of DBA but not murine models. (Panel A, left portion) Murine fetal liver Kit+ progenitors expressing tetracycline-regulatable shRNA against RPS19 were cultured in the absence (grey columns) or presence (black columns) of doxycycline either alone, or treated with metformin. After 8 days, the number of ter119+ erythroblasts were calculated. (A right) RPL11+/lox mice were left untreated (grey columns) or treated (black columns) with tamoxifen for 5 weeks prior to isolation of bone marrow Lin-Kit+ progenitors. Progenitors were differentiated in the presence or absence of metformin for 8 days before assessing the number of Ter119+ erythroblasts. (Panel B) In conjunction with flow cytometry, cultures were subjected to qRT-PCR for NLK expression and (Panel C) kinase NLK kinase activity was assessed by in vitro kinase assay. (Panel D) Zebrafish were reared and injected with control or rps19-specific morpholino and treated with 20 mM metformin 4 to 5 hours post fertilization (hpf). At day 3, embryos were stained with o-dianizidine to detect hemoglobin. Data are displayed as means+/−SD. Statistics: two-tailed Student's t test, significant *P<0.05
Figure 11:
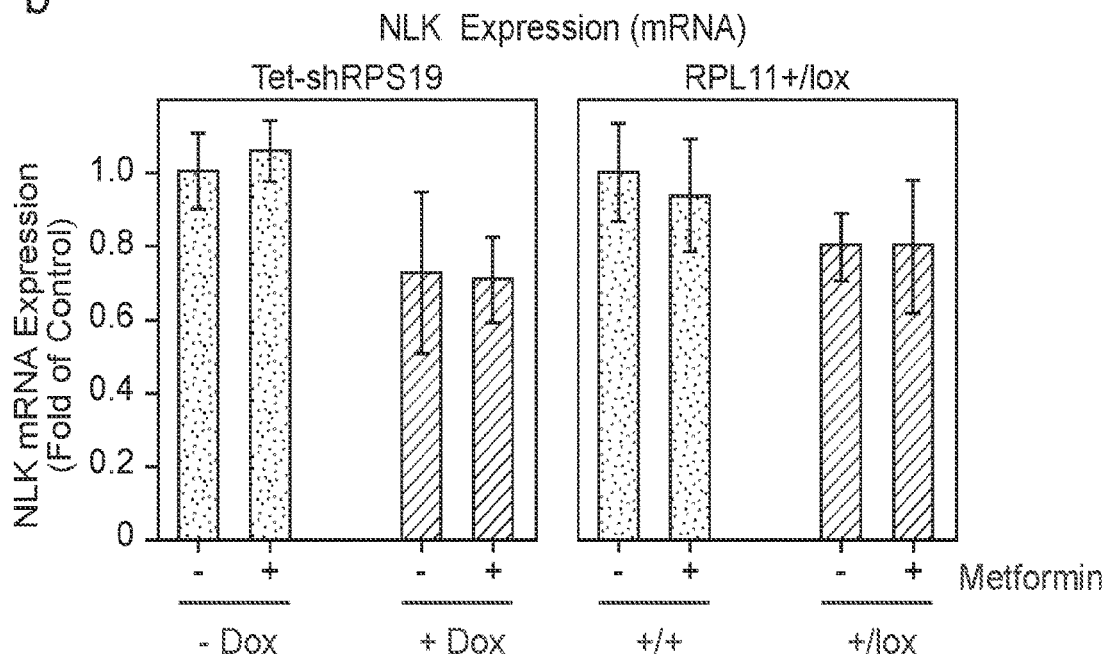
Figure 11:
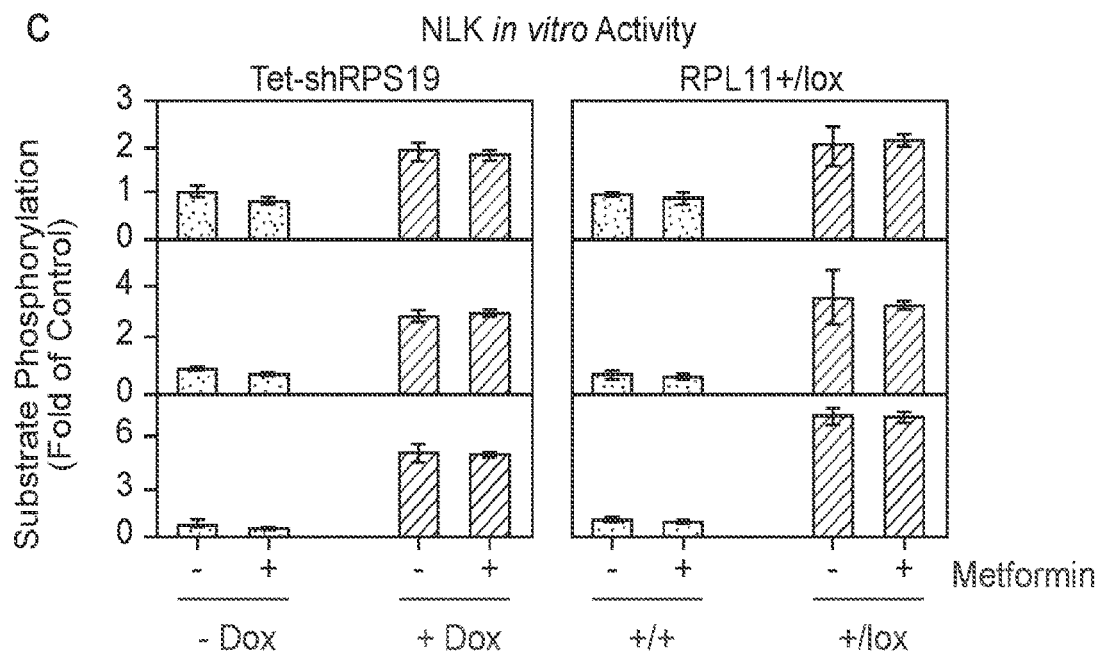
Figure 11:
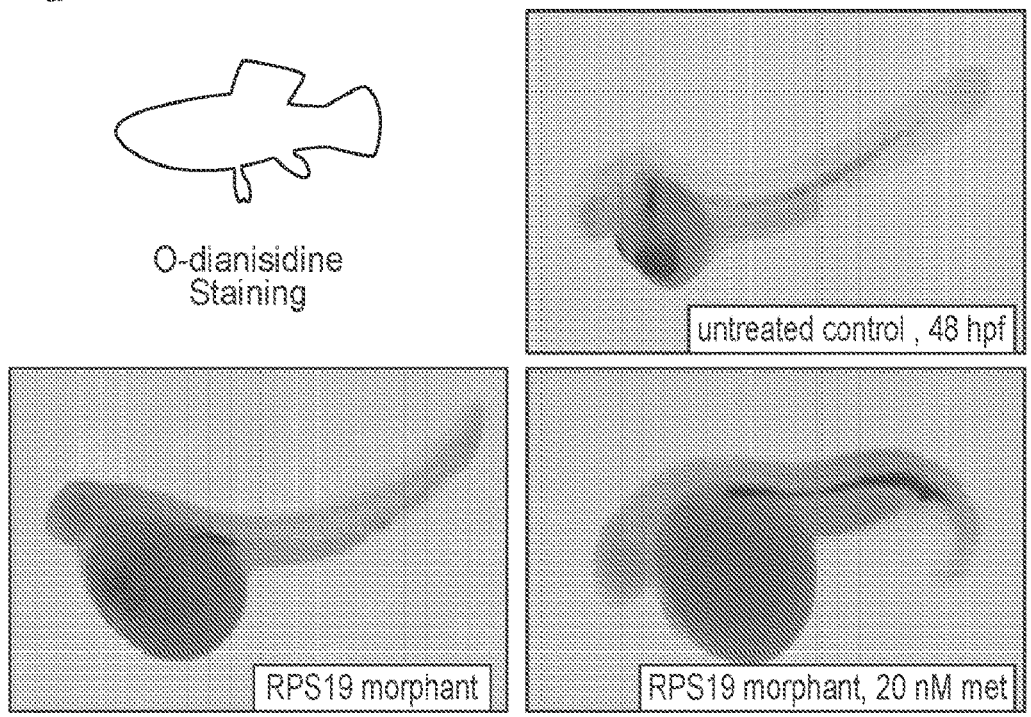

2. Metformin Improves Erythroid Expansion in Zebrafish but not Murine Models of DBA NLK activation has been observed to contribute to erythropoiesis defects in murine models of DBA (29, 33). However, metformin treatment did not rescue Ter119+ erythroblast expansion in RPS19- or RPL11-insufficiency (FIG. 11A). In contrast to human models, metformin had no impact on NLK expression (FIG. 11B) or NLK activity (FIG. 11C) in control or either RPS19- or RPL11-insufficient mice. In zebrafish (*Danio rerio*) anemia reminiscent of DBA occurs with RPS19-insufficiency (34). We induced RPS19-insufficiency by morpholino in the presence or absence of 20 mM metformin and examined hematopoiesis/hemoglobin activity in embryos by O'dianisidine staining. In RPS19-insufficiency, loss of O'dianisidine staining was significant, along with accompanying heart failure (FIG. 11D middle). Although heart conditions persisted, metformin dramatically restored O'diansidine staining, particularly along the midline (FIG. 11D right).

3. Metformin Sensitivity is Mediated Through a miR-26a-Binding Site within the NLK 3'UTR Having demonstrated that metformin improved erythropoiesis in ribosomal-insufficiency through NLK suppression in human models, we sought to determine the mechanism of action. The influence of miRNA on gene expression is often subtle (13), but it has been demonstrated that NLK expression can be extensively suppressed by miR-181 (7), miR-208 (8), miR-199 (10), miR-101 (9) and miR-221 (11). As miRNA influence is typically through binding to elements within the 3'UTR (13) we asked if metformin induced NLK degradation through the NLK 3'UTR.

Fusion of the NLK 3'UTR to the luciferase gene, but not 5' promoter sequence, resulted in a dose-dependent, metformin-mediated degradation of luciferase (67.5% decrease at 50 mM) similar to endogenous NLK suppression (FIG. 12A). Expression of luciferase alone, or fused with an alternative 3'UTR from SATB1, did not result in metformin sensitivity. In parallel with measuring luciferase activity, the response of endogenous NLK protein expression was monitored by Western blot analysis with a high degree of correlation.

Having determined that the suppressive effect of metformin on NLK in human hematopoietic cells is mediated by the 3'UTR, we asked if the lack of metformin sensitivity in mice was due to differences in the murine 3'UTR sequence. When expressed in human K562 cells, human, murine and zebrafish 3'UTR sequences all facilitated a dose-dependent reduction in luciferase activity (FIG. 12B), indicating all 3 species retain a conserved metformin-responsive element within the 3'UTR. The human 3'UTR facilitated a 65.4% (p=0.0056) decrease while the murine and zebrafish sequence reduced luciferase activity by 61.6% (p=0.008) and 43.6% (p=0.031) respectively (FIG. 12B).

The NLK 3'UTR sequence contains approximately 30 potential miRNA binding sequences. We generated a series of truncations in the human NLK 3'UTR sequence and analyzed the metformin-responsiveness (FIG. 13A). Luciferase fused to 3'UTR sequence lacking only the smallest deletions (truncations 1 and 2) retained metformin-sensitivity, while deletion of more nucleotides lost sensitivity (FIG. 13B). We conclude that the 261 nucleotides between truncations 2 and 3 are required for metformin-mediated suppression. This includes potential binding sites for 4 miRNA species; let-7, miR-30, miR-181 and two sequential binding sites for miR-26a (FIG. 13C). While comparison of human and mouse nucleotide sequence in this region reveals a high degree of sequence conservation (92.7% identical), the zebrafish sequence shares little conservation with the exception of a small region containing a miR-181 and one copy of the miR-26a binding sequences. Let-7, miR-181 and both miR-26a binding sequences are shared between human and mouse, while the miR-30 binding sequence found in the human sequence is lost in mice (FIG. 13D).

Figure 14:
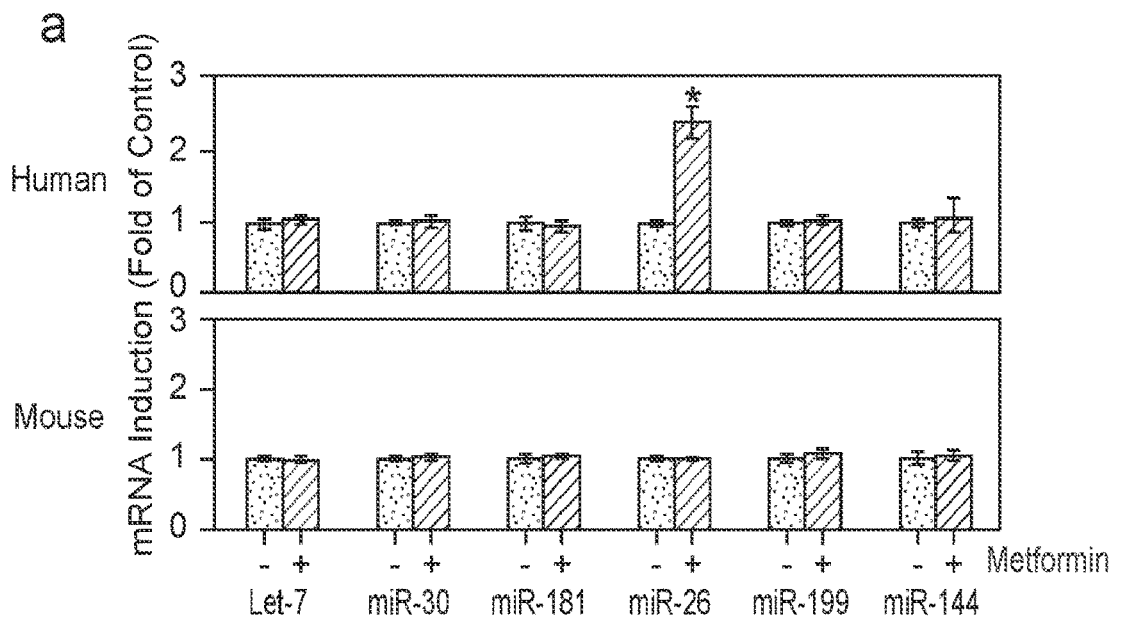
FIG. 14. Metformin-mediated upregulation of miR-26a in human progenitors suppresses NLK expression. (Panel A) Human CD34+ (upper) and murine Lin-Kit+ (lower) progenitors were differentiated for 8 days in the presence or absence of metformin and the levels of indicated miRNAs were assessed by qRT-PCR. (Panel B) K562 cells stably expressing the luciferase gene coupled to the NLK 3'UTR were mock transfected, transfected with indicated miRNA mimetics, or treated with metformin, and cultured in the presence or absence of metformin for 72 hrs. After lysis, luciferase activity was determined and endogenous NLK and GAPDH protein expression was analyzed by Western blot. (Panel C) K562 cells were mock transfected, or transfected with either miR-34 or miR-26 sponges, prior to being left untreated or treated with metformin for 72 hrs. Lysed cells were subjected to luciferase assay and western blotting to examine NLK and GAPDH protein expression. Data are displayed as means+/−SD. Statistics: two-tailed Student's t test, significant *P<0.05
Figure 14:
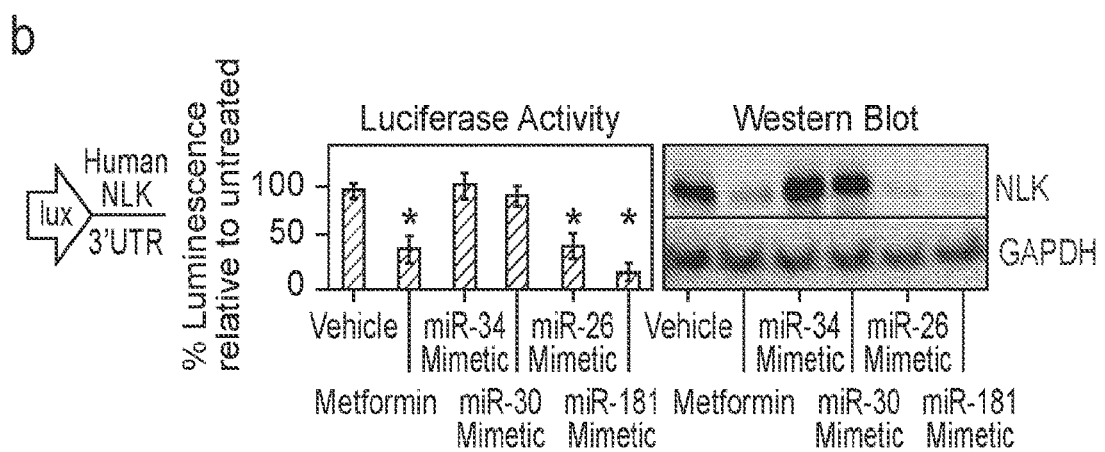
Figure 14:
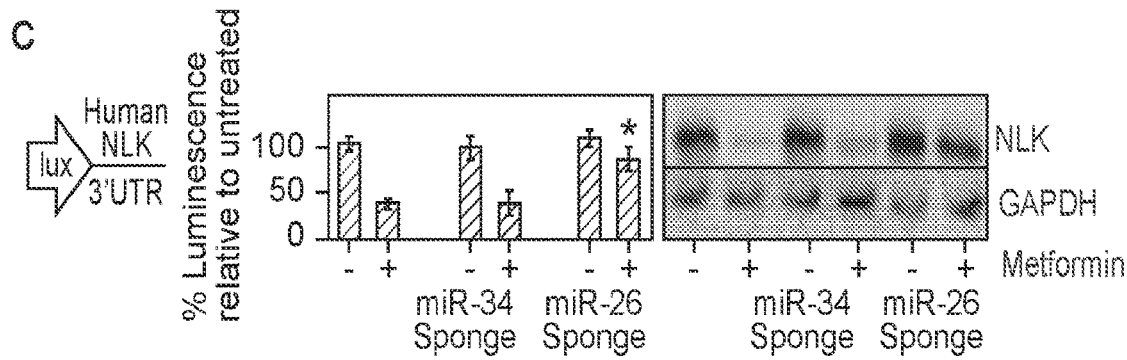
Figure 14:
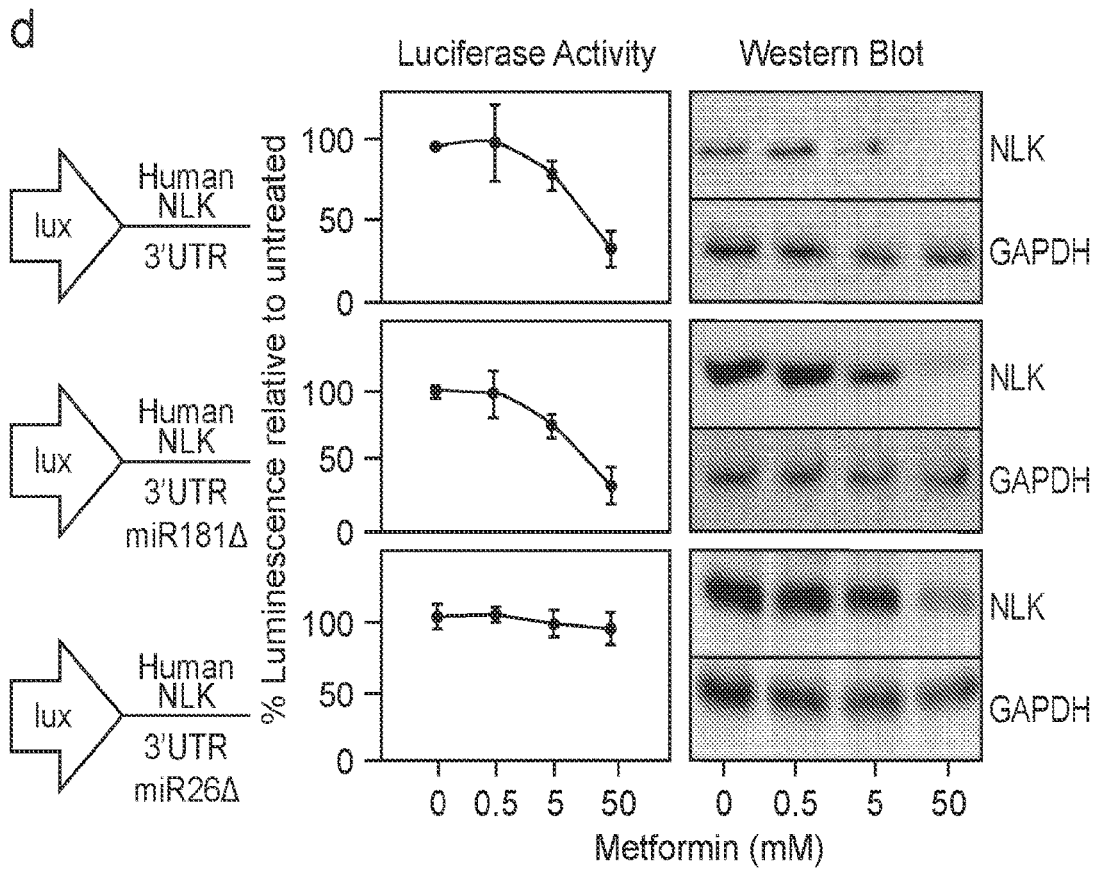
Figure 14:
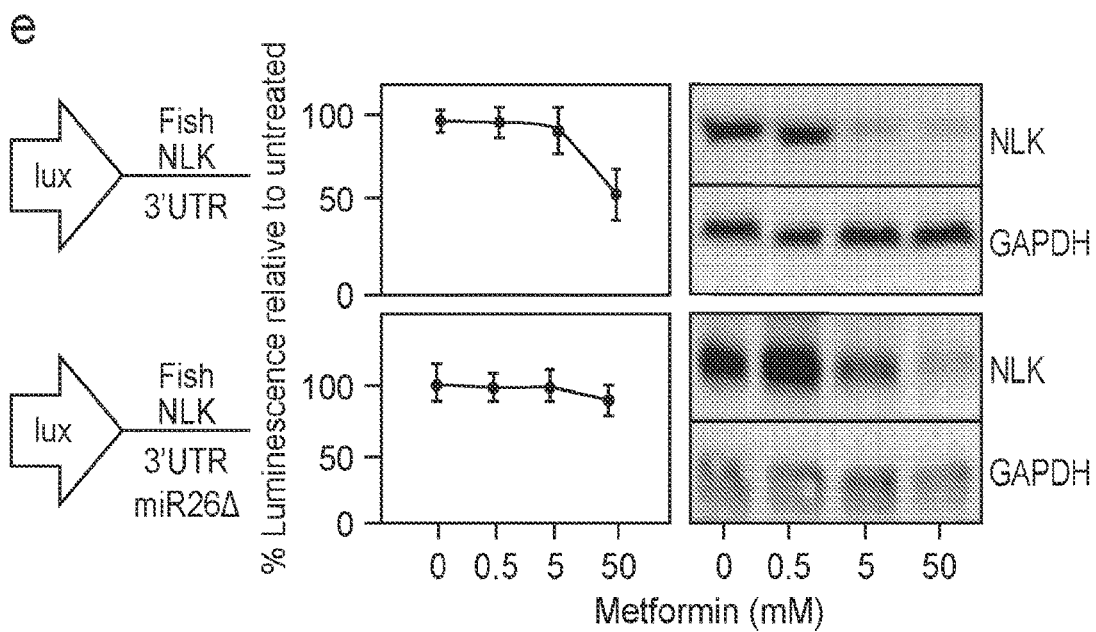

4. NLK Suppression is Mediated by miR26a Induction by Metformin in Human, but not Murine Models of DBA To identify which miRNA was responsible for metformin-induced NLK suppression, we compared the expression of a number of miRNA species between untreated and metformin-treated CD34+ progenitors differentiating in erythroid media. As the metformin-responsive region of the NLK 3'UTR contained predicted binding sites for let-7, miR-30, miR-181 and miR-26a, we initially focused on these. With the exception of miR-26a, metformin did not alter the expression of any miRNA species. In contrast, miR-26a was upregulated 2.4-fold in response to metformin (FIG. 14A upper). Comparison of the entire 3'UTR between human, mouse and zebrafish revealed that, apart from miR-181 and miR-26a within the metformin-response element, the only other miRNA-binding sites conserved between all 3 species was miR-199 and miR-144. However, metformin did not alter expression of either of these miRNAs in human erythropoiesis (FIG. 14A upper). As the murine 3'UTR sequence of NLK is metformin-responsive when expressed in human cells, we examined the miRNA expression profile in response to metformin in differentiating Lin-Kit+murine progenitors. In contrast to the human system, none of the miRNA species examined demonstrated significant upregulation (FIG. 14A lower).

Having observed upregulation of miR-26a in response to metformin, and the presence of a miR-26a binding site within the metformin-responsive element of the NLK 3'UTR, we asked whether the metformin response is due to miR-26a upregulation. In human K562 cells expressing luciferase fused to a wild-type human NLK 3'UTR, recombinant expression of a miR-26a mimetic, but not miR-30 or miR-34 mimetics, reduced luciferase activity and endogenous NLK protein expression by 58.8% (p=0.0155) and 55.1% respectively (p=0.0311) (FIG. 14B). The effect of miR-26a mimetics reduced luciferase and endogenous NLK expression similarly to that observed with metformin treatment (72.5% and 68.6%). A striking suppression of NLK has been reported in response to miR-181 (7). Suppression of luciferase activity and endogenous NLK by miR-181 mimetics was more extensive (85.6% and 88.0%) than was observed in response to metformin or miR-26a mimetics (FIG. 14B). Furthermore, expression of a miR-26a inhibitor reduced both the luciferase and endogenous NLK metformin-response by 74.1% (p=0.0416) and 70.3% (p=0.0449) respectively, whereas a miR-34 inhibitor had a negligible effect (FIG. 6C).

The preceding data support a model in which metformin induces miR-26a expression in differentiating human hematopoietic cells. MiR-26a binds a sequence within the NLK 3'UTR facilitating NLK mRNA degradation. The mouse NLK 3'UTR sequence does include miR-26a binding sites, however in differentiating hematopoietic cells no miR-26a induction was observed in response to metformin in mice.

As metformin increases erythropoiesis in RPS19-insufficient human CD71+ progenitors, we compared CD235+ erythroid expansion in response to metformin, with expression of miR-26a mimetics, or a combination of both. RPS19-insufficiency decreased production of CD235+erythroblasts to 8.3% of controls, however miR-26a mimetics, metformin treatment, and the combination all improved erythropoiesis similarly (3.4-fold; p=0.0324, 3.6-fold; p=0.0394 and 3.5-fold; 0.0279 respectively). No significant difference was observed between miR-26a mimetic alone compared to metformin alone (p=0.8544) or when treated together with metformin (p=0.9615). Negligible effects on erythropoiesis were observed in control (shLuc) with any treatment (FIG. 15A upper).

NLK expression was similarly suppressed by metformin, miR-26a, and the combination in both RPS19-insufficient and control cells (FIG. 15A middle). Metformin increased miR-26a in both RPS19-insufficiency (2.5-fold, p=0.0001) and control (2.4-fold, p=0.0088), while miR-26a mimetics elevated levels to 3.6-fold (p=0.005) and 3.5-fold (p=0.0012). Combined treatment did not significantly increase miR-26a expression relative to either treatment alone (FIG. 15A lower). Despite not responding to metformin (FIG. 11A), the expression of miR-26a mimetics in murine Lin-Kit+ induced a moderate (1.75-fold; p=0.0166) increase in ter119+ erythroid expansion (FIG. 15B upper), with corresponding NLK suppression (FIG. 15B middle).

Figure 10:
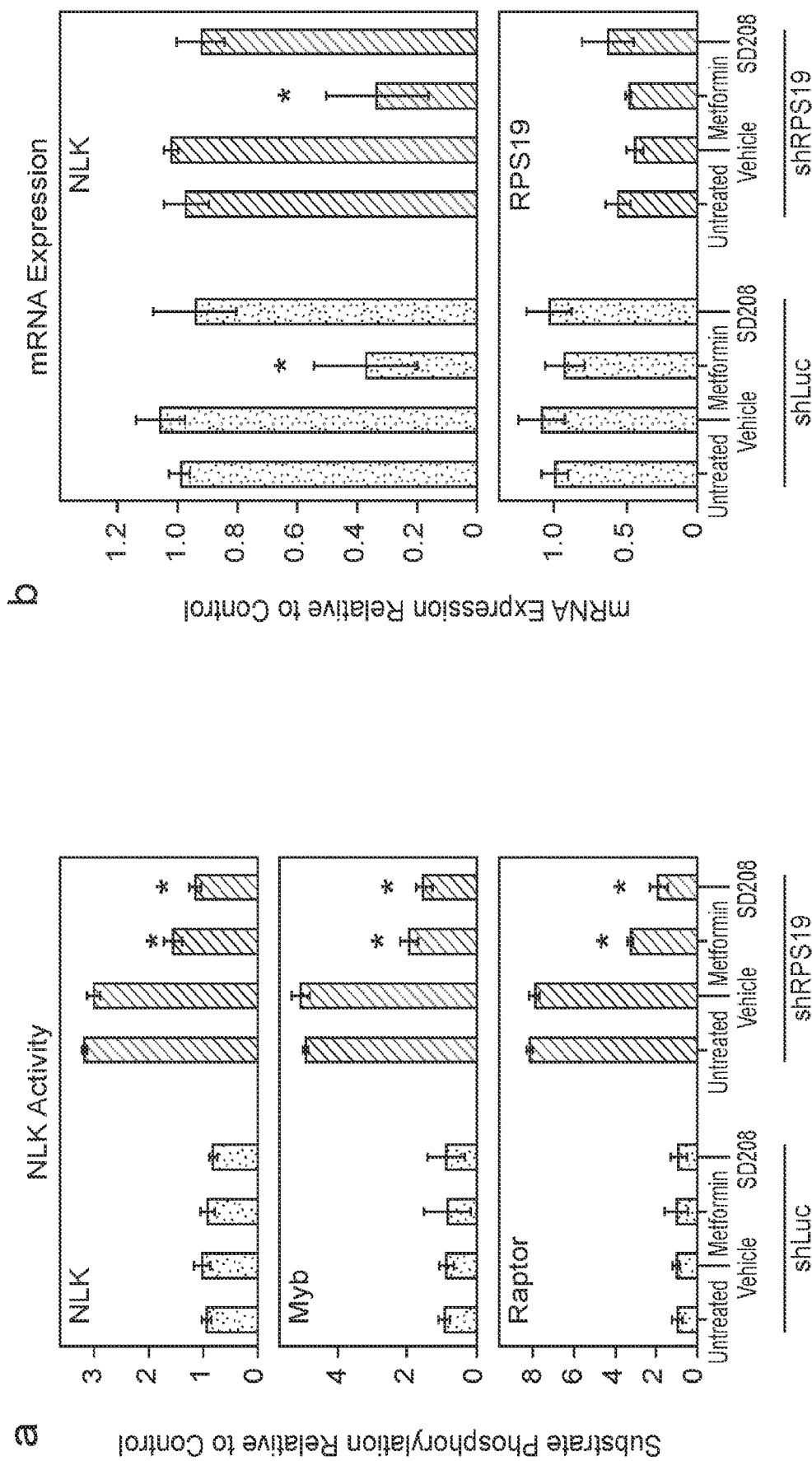
FIG. 10. Metformin improves erythropoiesis through suppression of NLK expression. (Panel A) Control (shLuc—grey columns) or RPS19-insufficient (shRPS19—black columns) progenitors were differentiated in erythroid media alone, vehicle or vehicle containing 50 mM metformin or 5 uM SD208 for 5 days. 5000 cells per treatment were lysed and immunopurified NLK was subjected to in vitro kinase assay to determine phosphorylation potential against 3 recognized NLK substrates; NLK itself (upper), c-Myb (middle) or raptor (bottom). (Panel B) Simultaneously, qRT-PCR was performed to examine NLK (upper) and RPS19 (lower) mRNA expression. (Panel C) Active NLK was purified from activated Kp53A1 cells and subjected to in vitro kinase assay in the presence of 0, 50 nM, 50 µM, or 50 mM metformin or SD208. The phosphorylation of NLK (upper), c-Myb (middle) and raptor (lower) was determined after 30 mins. (Panel D) CD34+ progenitors were transduced with a combination of either shRNA against luciferase (shLuc—grey columns) or RPS19 (shRPS19—black columns) and siRNA against a non-targeting sequence (NT) or NLK (siNLK). After 14 days differentiation in the presence or absence of metformin, cells were counted and the percentage of cells with surface expression of CD235 and CD11b were determined by flow cytometry, to yield the number of CD235+ erythroid (upper) and CD11b+ myeloid (lower) cells. The total number of cells is expressed as a percentage of the number of each cell type in the control (untreated/shLuc/NT). Data are displayed as means +/−SD. Statistics: two-tailed Student's t test, significant *P<0.05
Figure 10:
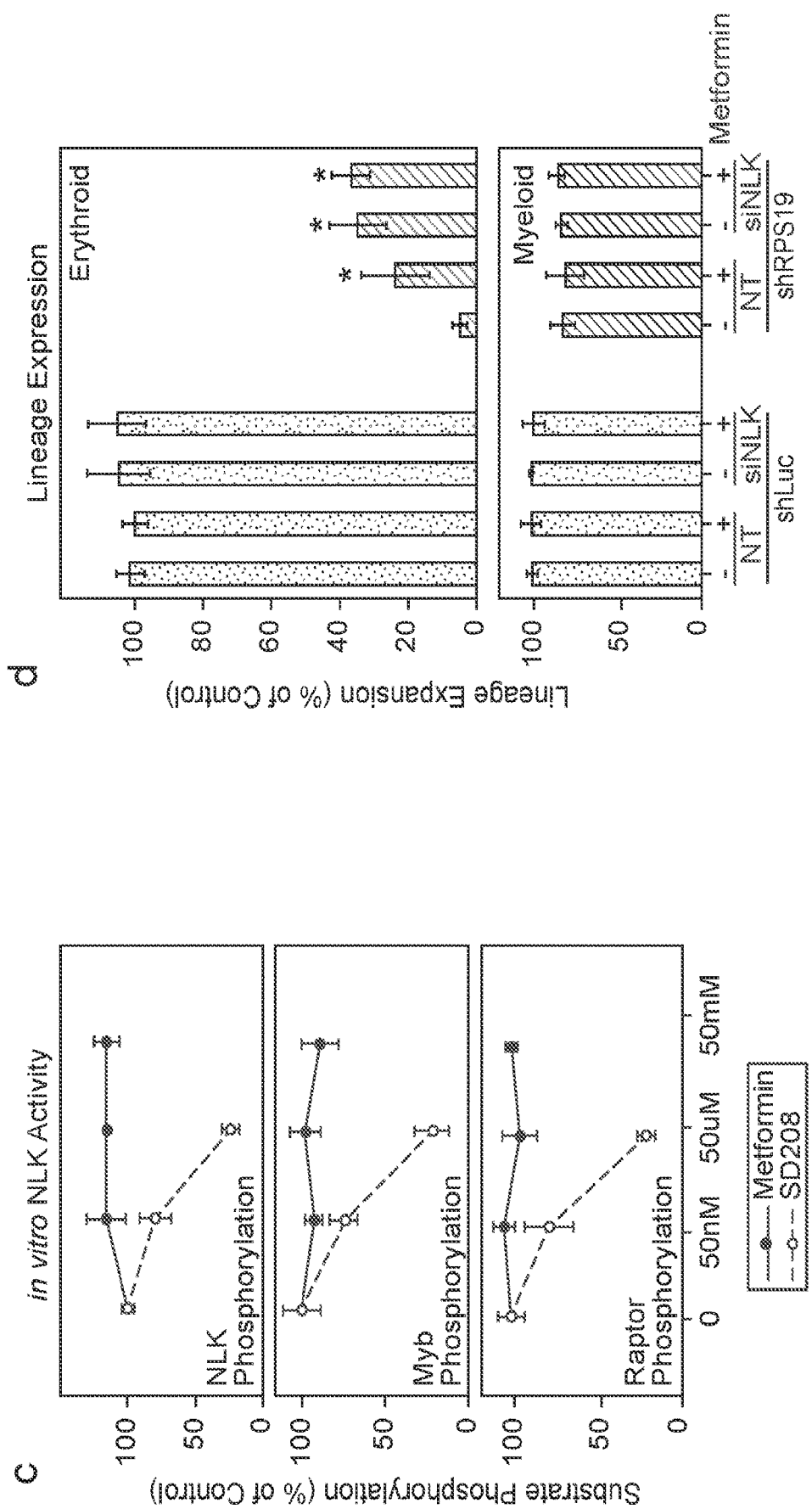
Figure 12:
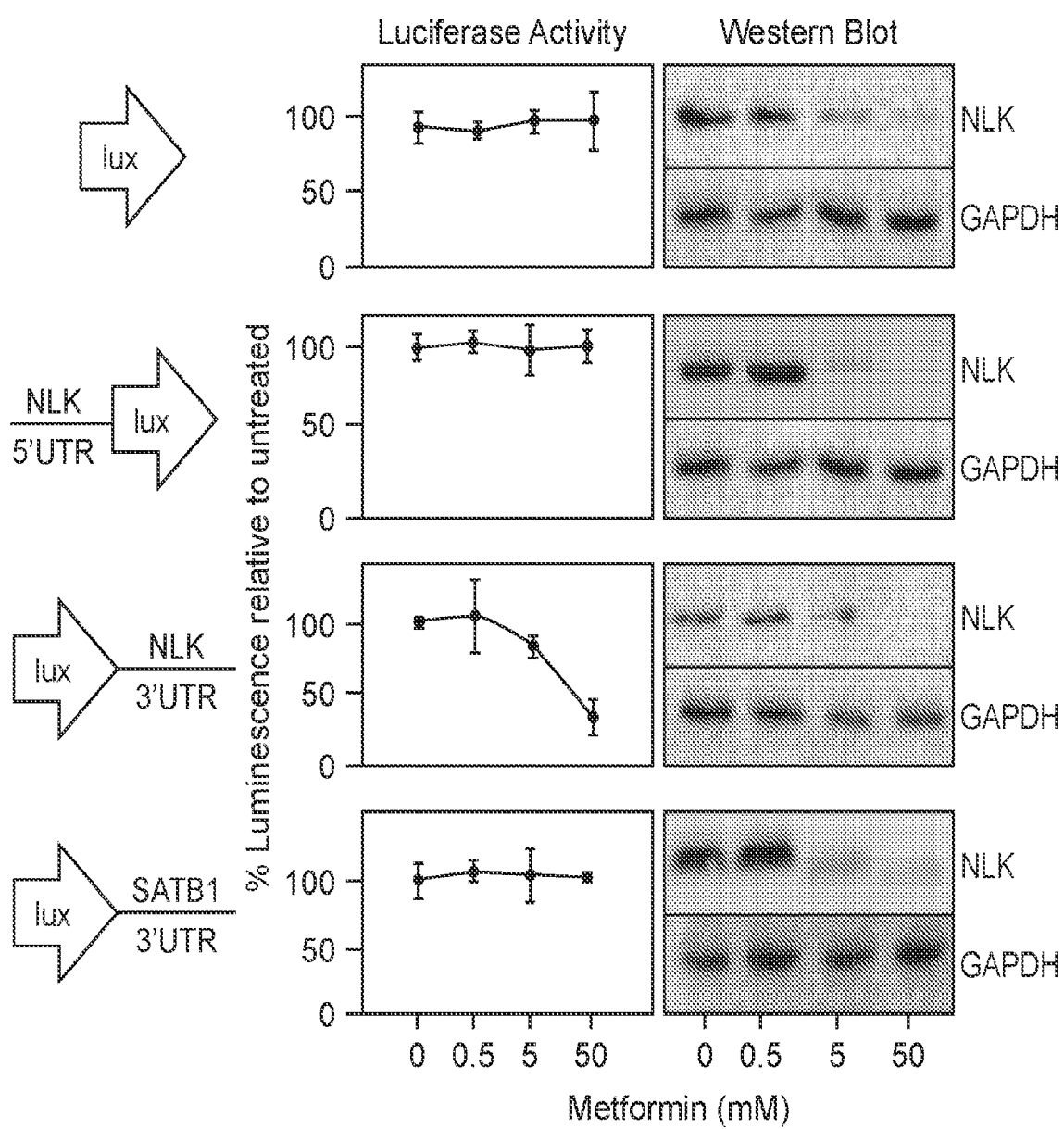
FIG. 12. NLK 3'UTR facilitates metformin-mediated NLK suppression. (Panel A) K562 cells stabling expressing luciferase alone (top portion), luciferase expressed behind a minimal promoter and the NLK proximal promoter (2nd portion), luciferase immediately upstream of the human NLK 3'UTR (3rd portion) or luciferase with the SATB1 3'UTR (bottom portion) were grown in the presence of 0, 0.5, 5.0 or 50.0 mM of metformin for 72 hrs. Cell were pelleted and either processed for luciferase assay (left portion) or western blot analysis of endogenous NLK (upper right portion) or GAPDH (lower right portion). (Panel B) Luciferase immediately upstream of the human (upper), murine (middle) and zebrafish (lower) NLK 3'UTR were transiently transfected into human K562 (left) and cultured with indicated concentrations of metformin for 72 hrs. Lysates were assessed for luciferase activity and endogenous NLK and GAPDH protein expression by Western blotting. Data are displayed as means+/−SD. Statistics: two-tailed Student's t test, significant *P<0.05
Figure 12:
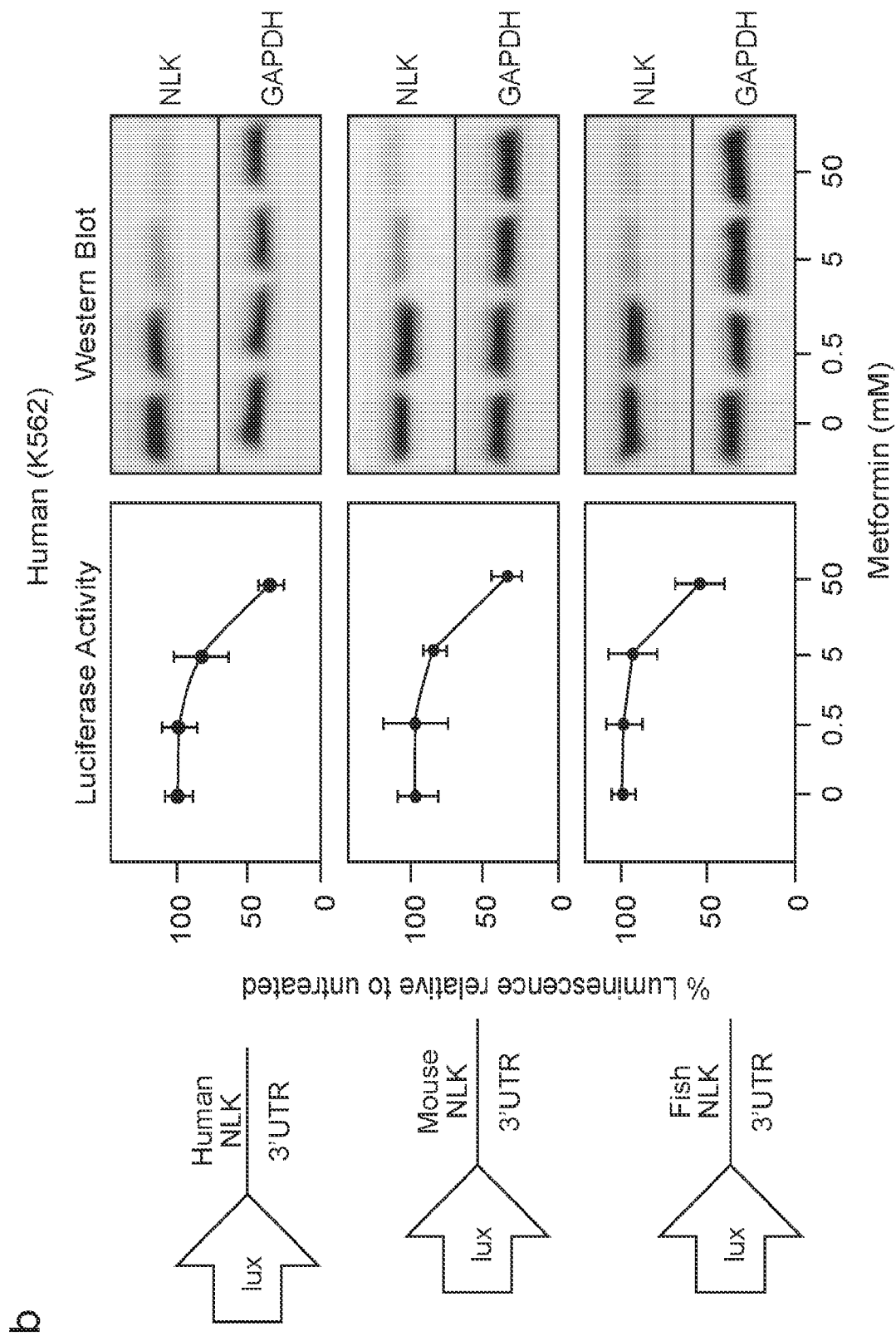
Figure 13:
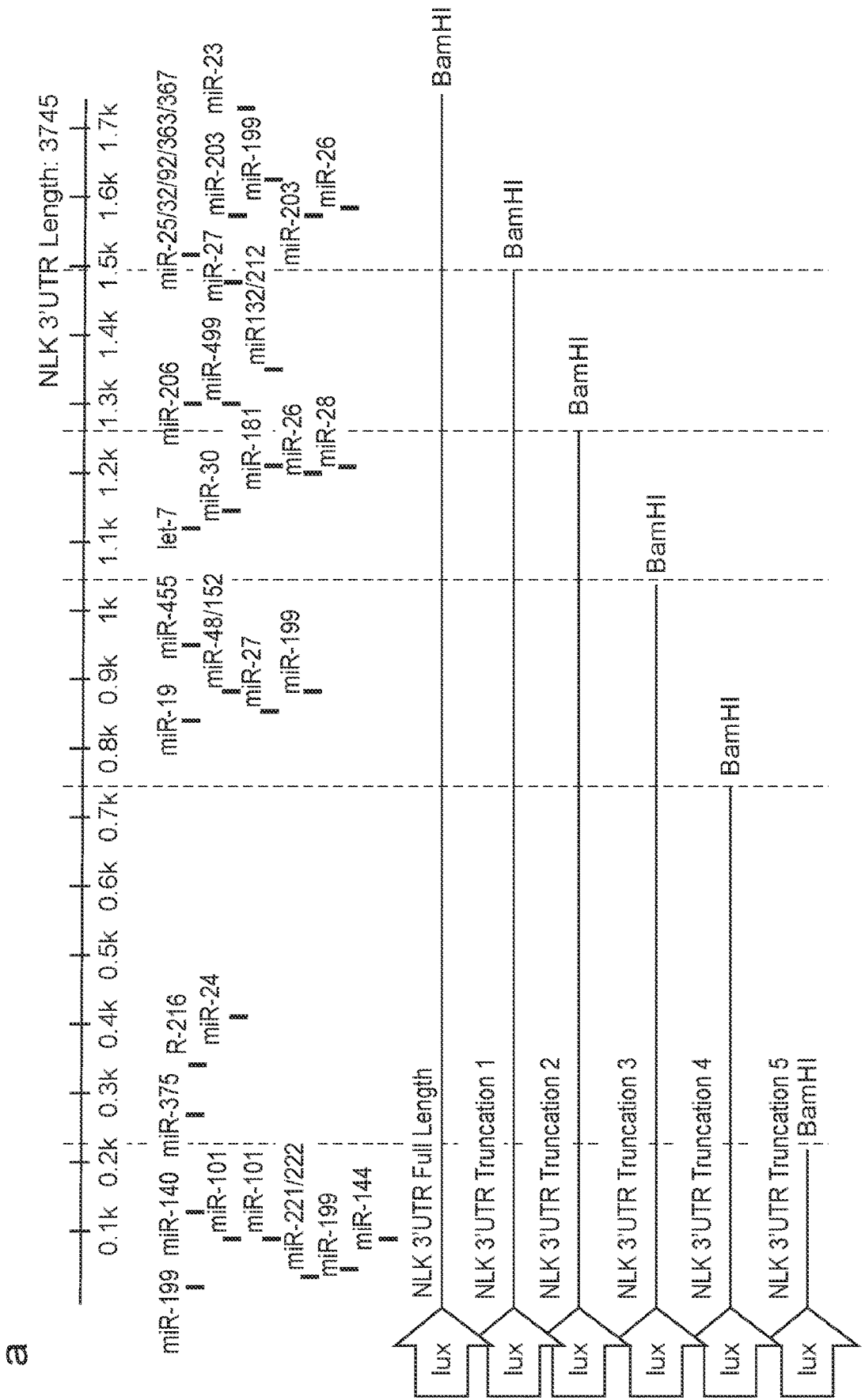
FIG. 13. NLK 3'UTR metformin-response element contains 4 potential miRNA binding sites and is highly conserved between human and mouse but divergent in zebrafish. (Panel A) Schematic representing the many potential miRNA binding sites within the human NLK 3'UTR (upper). Diagrammatic representation of the full length and 5 truncated constructs fused to the luciferase gene and engineered to determine the metformin-responsive element within the NLK 3'UTR (lower). (Panel B) After transient transfection of plasmids carrying the various 3'UTR fragments, K562 cells were treated with indicated concentrations of metformin for 72 hrs. and assessed for luciferase activity and endogenous NLK and GAPDH protein expression by Western blot. (Panel C) A schematic indicating the potential miRNA binding sites contained within the metformin-responsive element. (Panel D). The corresponding nucleotide sequences of the human, mouse and zebrafish NLK 3'UTRs across the metformin-responsive element. Data are displayed as means+/−SD. Statistics: two-tailed Student's t test, significant *P <0.05
Figure 13:
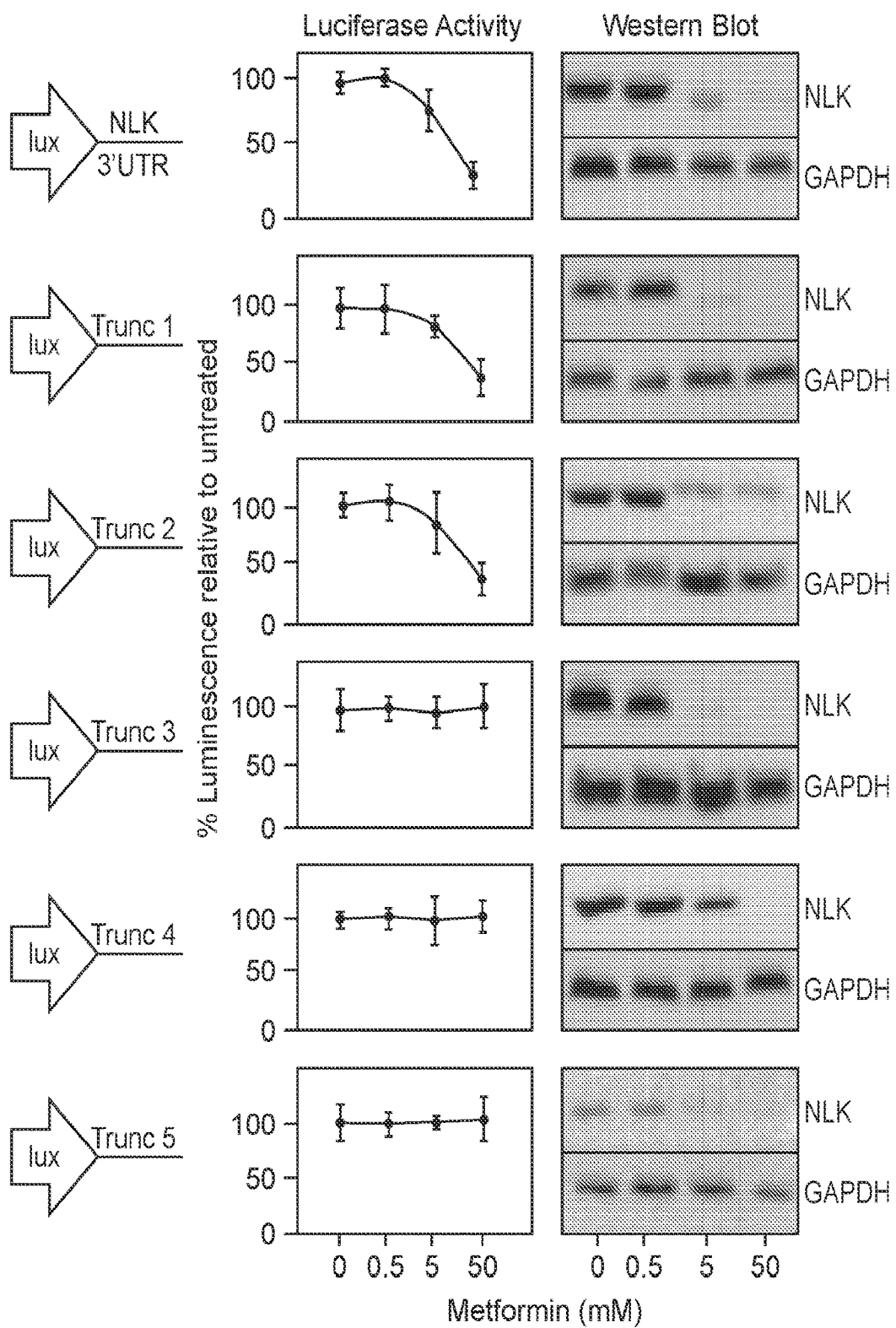
Figure 15:
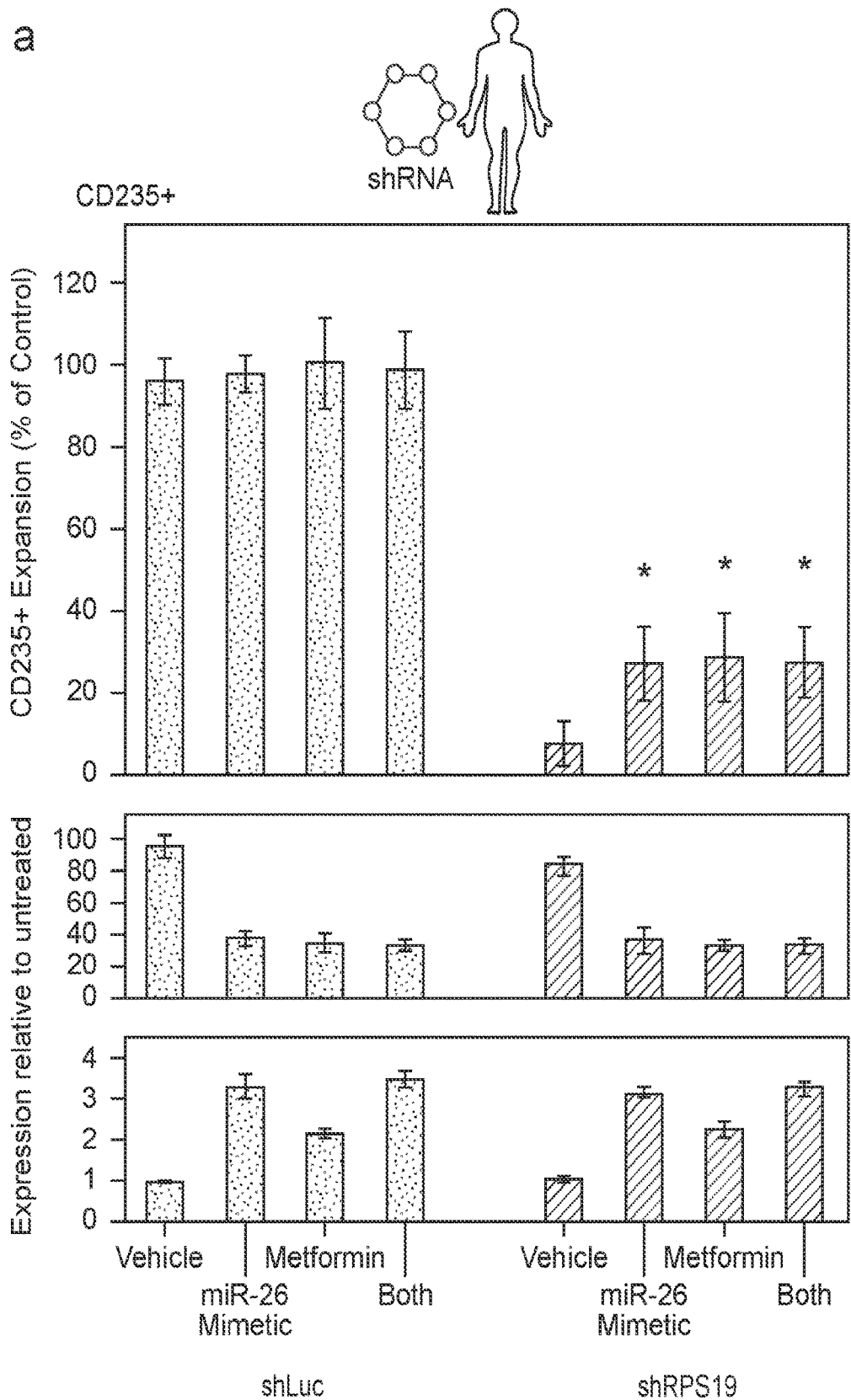
FIG. 15. MiR-26a mimetic substitutes for metformin in improving erythropoiesis in RPS19-insufficiency. (Panel A) Human CD34+ cells were transduced with shRNA against a control (shLuc) or RPS19 (shRPS19) and transfected with a miR-26a mimetic or a mock control. After differentiation in the absence or presence of metformin for 12 days, cells were counted and the percentage of CD235+ erythroblasts determined by flow cytometry. The calculated CD235+ population of each treatment group is represented as a percentage of the untreated control group (upper). In parallel, qRT-PCR was performed to determine mRNA expression of NLK (middle) and miR-26a (lower). (Panel B) Lin-Kit+ progenitors for RPL11+/+ and RPL+/lox mice were mock transfected or transfected with miR-26a mimetic and differentiated for 8 days. Cells were subjected to counting and the percentage of Ter119+ erythroblasts determined (upper) in conjunction with qRT-PCR examining NLK (middle) and miR-26a (lower) mRNA expression. Data are displayed as means+/−SD. Statistics: two-tailed Student's t test, significant *P<0.05
Figure 15:
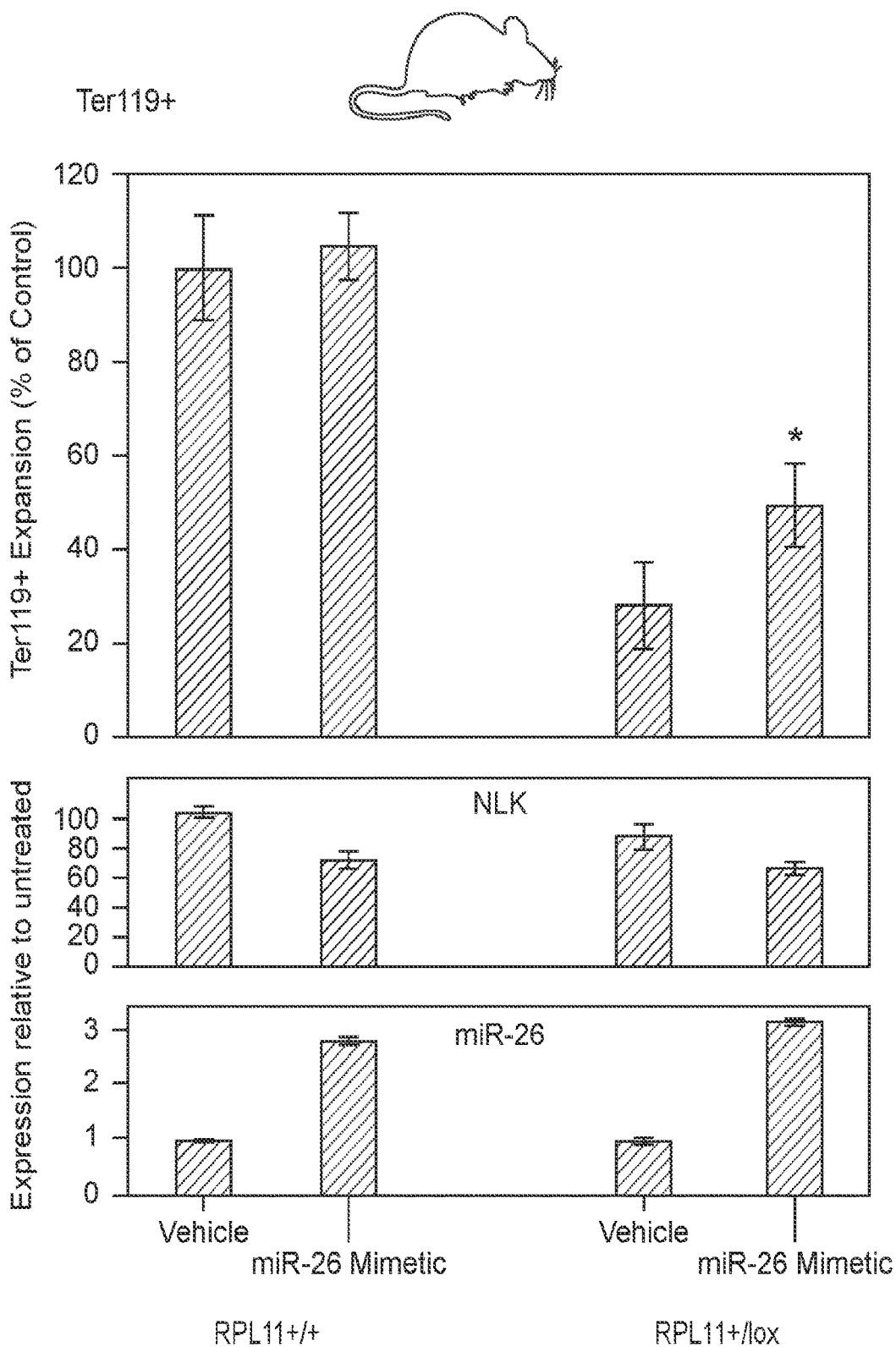

Collectively, we demonstrate that metformin improves erythroid expansion in RPS19- and RPL11-insufficient human (FIG. 9) and zebrafish (FIG. 11) models of DBA. The effect appears to be exclusively mediated through the suppression of NLK expression (FIG. 10). Our results showed that metformin induces miR-26a (FIG. 14) that binds a consensus sequence in the NLK 3'UTR (FIGS. 12 & 13). Furthermore, the expression of miR-26a mimetics had no significant difference with metformin treatment regarding improvement of erythropoiesis in human models of DBA (FIG. 15). While metformin did not improve erythropoiesis in murine models of DBA (FIG. 11) due to a failure to induce miR-26a (FIG. 14), expression of miR26a mimetics improved erythroid expansion in the murine model (FIG. 15).

E. Discussion

Here we report that metformin treatment improves erythropoiesis in human and zebrafish models of DBA. We hypothesized NLK-independent metformin effects would inhibit human erythropoiesis in ribosomal insufficiency. We detected no evidence to support this in vitro and metformin was well tolerated at the indicated doses. In human cells, metformin-induces upregulation of miR-26a, which targets NLK for degradation. In murine models, metformin failed to induce miR-26a, however inducing miR-26a expression with transduced cDNA effectively suppressed NLK expression and improved erythropoiesis.

In addition to miR-26a, the 3'UTR of NLK is particularly susceptible to miR-181 binding, a feature that has been documented in hepatocellular carcinoma (35) and natural killer (NK) cell development (7). It is intriguing that the NLK 3'UTR is more sensitive to miRNA-mediated degradation than others. While a complementary miRNA seed sequence is critical, numerous other factors contribute to defining the efficacy with which a miRNA will bind and/or degrade a transcript. These include GC content, sequence and secondary structures that dictate stability of both miRNA and RISC complex binding, as well as intrinsic diversity of 3'UTR length and structure across copies of some transcripts (36). While mouse and human NLK 3'UTR sequences are highly conserved, the zebrafish 3'UTR is highly divergent. Nevertheless, one copy of the miR-26a binding site and the miR-181-binding site is conserved. The upregulation of miR-181 after the MEP stage is critical for megakaryocyte lineage differentiation (37). Indeed, upregulation of miR-181 is induced in all non-erythroid lineages (37-41). Mutation of the miR-181 binding site in the NLK 3'UTR increased NLK expression in non-erythroid progenitors resulting in adverse lineage expansion (5). The importance of NLK expression in lineage differentiation may contribute to the evolution of the highly sensitive NLK 3'UTR. It is also possible that the highly conserved role of miR-181 in the regulation of hematopoiesis provides evolutionary pressure to conserve the region surrounding miR-181, thus maintaining the miR-26a binding site by association.

Metformin treatment did improve o-dianizidine in RPS19-insufficient zebrafish. However, the staining was predominantly along the midline and did not restore cardiac defects, as have been seen upon p53 suppression (42). This may be due to the incomplete rescue by NLK suppression, or that heart defects are an NLK-independent effect of RPS19 insufficiency in fish. Zebrafish carry two nlk homologues, nlk1 and nlk2. Nlk2 is implicated in similar signaling pathways as human and murine homologues, but a role in hematopoiesis has not been examined (43). We have no direct evidence that nlk1 or 2 is activated, nor that metformin suppresses NLK expression in RPS19-insufficient zebrafish erythroid cells. However, given that metformin improved erythropoiesis in RPS19-insufficient embryos and metformin treatment degraded zebrafish NLK 3'UTR transcripts, it is highly probable that NLK is similarly deregulated in and metformin-sensitive as human erythroblasts.

Another interesting result was the failure of miR-26a induction in response to metformin in murine erythroblasts. The deregulation of miRNAs in response to metformin has been evaluated in numerous cell and animal models. Effects of metformin have ranged from no miRNA deregulation (44) to hundreds (45). As miRNA expression profiles commonly differ across cell type and species, it is not surprising that miR-26a is not upregulated in response to metformin in RPS19-insufficient hematopoietic cells of all species. Metformin-mediated upregulation of miR-26a has been previously reported, inducing apoptosis in oral cancer cells (46) and contributing to reduced incidence and increased survival in breast cancer patients (47).

MiR-26a has been primarily linked to apoptosis, serving as pro-apoptotic (48-50) and anti-apoptotic (51), depending on the cell context. Other cellular roles attributed to miR-26a include activation of mTOR signaling by suppression of PTEN (52) (which would be potentially beneficial in DBA), suppression of ERBB2 (53), and suppression of HMGA1 (54).

Suppression of another MAPK-family kinase by miR-26a has been previously reported (55) in rats but the miR-26a-binding site present in the rat MAPK6 3'UTR sequence is not retained in the human sequence. Analysis of 3'UTR sequences across the human MAPK/cdk kinase family indicate no predicted miR-26a-binding sites within MAPK1-10 or MAP2K1-6 and 1 in each of MAP3K1 and MAP3K2 but none in MAP3K3-8. There were three miR-26a-binding sites within the 3'UTR of cdk8 but none were identified in cdk1-7, 9 or 10.

As NLK expression can have both tumor suppressive (9, 35, 56-59) and oncogenic (10, 16, 60-67) functions, depending on the origin of the malignancy, systemic NLK suppression may have significant risks. In a disease such as DBA in which most patients present early in life and some require life-long therapy (1), minimizing effects beyond the affected tissue becomes even more prudent. Many miRNAs demonstrate differential expression between tissues (13), so miRNA mimetics that suppress NLK in tissues of interest, but preserve NLK activity in tissues where NLK expression is favorable, may be advantageous. While the mechanism of metformin is through upregulation of miR-26a, improved NLK suppression and/or tissue-specificity may be engineered by targeting other miRNA-binding sites within the 3'UTR.

P53 suppression, mTOR stimulation and steroid regimes, impact regulators of multiple critical cellular processes. Targeting NLK may offer less potential side-effects. NLK null mice are viable and grow normally (68). NLK expression is not ubiquitous and enzymatic activity, like other kinases, is highly regulated (69). NLK likely plays no role during normal hematopoiesis and NLK expression is suppressed in all non-erythroid hematopoietic lineages. In normal erythroblasts, NLK activity is low and silencing NLK has no apparent impact on erythropoiesis. An influence of NLK on erythropoiesis is only established upon aberrant activation, which occurs downstream of p53-stabilization in DBA (5). These properties make agents that specifically target NLK expression in hematopoietic cells highly attractive.

Targeting miR-26a mimetics to hematopoietic cells in a murine system has already been effectively demonstrated using aptamer-based target delivery (70). Murine HSPCs highly express c-kit and Tanno and a miRNA-aptamer chimera containing miR-26a mimic and c-kit-targeting aptamer was successfully delivered miR-26a into HSPCs to attenuate the toxicity of 5'fluorouracel and carboplatin. Specific targeting of NLK in RP-insufficient hematopoietic cells coupled with naturally limited expression of NLK within non-erythroid lineages, offers a more selective therapeutic approach for DBA patients.

F. References

1. Da Costa L, Narla A, Mohandas N. An update on the pathogenesis and diagnosis of Diamond-Blackfan anemia. F1000Research. 2018; 7.

2. Ulirsch J C, Verboon J M, Kazerounian S, Guo M H, Yuan D, Ludwig L S, et al. The Genetic Landscape of Diamond-Blackfan Anemia. American journal of human genetics. 2018 Dec. 6; 103 (6): 930-47.
3. Khajuria R K, Munschauer M, Ulirsch J C, Fiorini C, Ludwig L S, McFarland S K, et al. Ribosome Levels Selectively Regulate Translation and Lineage Commitment in Human Hematopoiesis. Cell. 2018 Mar. 22; 173 (1): 90-103.e19.
4. Dutt S, Narla A, Lin K, Mullally A, Abayasekara N, Megerdichian C, et al. Haploinsufficiency for ribosomal protein genes causes selective activation of p53 in human erythroid progenitor cells. Blood. 2011 Mar. 3; 117 (9): 2567-76.
5. Wilkes M C, Siva K, Chen J, Varetti G, Youn M Y, Chae H, et al. Diamond Blackfan anemia is mediated by hyperactive Nemo-like kinase. Nature communications. 2020 2020 Jul. 3; 11 (1): 3344.
6. Cargnello M, Roux P P. Activation and function of the MAPKs and their substrates, the MAPK-activated protein kinases. Microbiology and molecular biology reviews: MMBR. 2011 March; 75 (1): 50-83.
7. Cichocki F, Felices M, McCullar V, Presnell S R, Al-Attar A, Lutz C T, et al. Cutting edge:
microRNA-181 promotes human N K cell development by regulating Notch signaling. Journal of immunology (Baltimore, Md: 1950). 2011 Dec. 15; 187 (12): 6171-5.
8. Yan X, Liu J, Wu H, Liu Y, Zheng S, Zhang C, et al. Impact of miR-208 and its Target Gene Nemo-Like Kinase on the Protective Effect of Ginsenoside Rb1 in Hypoxia/Ischemia Injured Cardiomyocytes. Cellular physiology and biochemistry: international journal of experimental cellular physiology, biochemistry, and pharmacology. 2016; 39 (3): 1187-95.
9. Shen Q, Bae H J, Eun J W, Kim H S, Park S J, Shin W C, et al. MiR-101 functions as a tumor suppressor by directly targeting nemo-like kinase in liver cancer. Cancer letters. 2014 Mar. 28; 344 (2): 204-11.
10. Han Y, Kuang Y, Xue X, Guo X, Li P, Wang X, et al. NLK, a novel target of miR-199a-3p, functions as a tumor suppressor in colorectal cancer. Biomedicine & pharmacotherapy=Biomedecine & pharmacotherapie. 2014 June; 68 (5): 497-505.
11. He X Y, Tan Z L, Mou Q, Liu F J, Liu S, Yu C W, et al. microRNA-221 Enhances MYCN via Targeting Nemo-like Kinase and Functions as an Oncogene Related to Poor Prognosis in Neuroblastoma. Clinical cancer research: an official journal of the American Association for Cancer Research. 2017 Jun. 1; 23 (11): 2905-18.
12. Lazare S S, Wojtowicz E E, Bystrykh L V, de Haan G. microRNAs in hematopoiesis. Experimental cell research. 2014 Dec. 10; 329 (2): 234-8.
13. Wilkes M C, Repellin C E, Sakamoto K M. Beyond mRNA: The role of non-coding RNAs in normal and aberrant hematopoiesis. Molecular genetics and metabolism. 2017 November; 122 (3): 28-38.
14. Onge E S, Miller S A, Motycka C, DeBerry A. A review of the treatment of type 2 diabetes in children. J Pediatr Pharmacol Ther. 2015 January-February; 20 (1): 4-16.
15. Dowling R J, Goodwin P J, Stambolic V. Understanding the benefit of metformin use in cancer treatment. BMC medicine. 2011 Apr. 6; 9:33.
16. Suwei D, Liang Z, Zhimin L, Ruilei L, Yingying Z, Zhen L, et al. NLK functions to maintain proliferation and stemness of NSCLC and is a target of metformin. Journal of hematology & oncology. 2015 Oct. 26; 8:120.
17. Jiang X, Ma N, Wang D, Li F, He R, Li D, et al. Metformin inhibits tumor growth by regulating multiple miRNAs in human cholangiocarcinoma. Oncotarget. 2015 Feb. 20; 6 (5): 3178-94.
18. Ortega F J, Mercader J M, Catalan V, Moreno-Navarrete J M, Pueyo N, Sabater M, et al. Targeting the circulating microRNA signature of obesity. Clinical chemistry. 2013 May; 59 (5): 781-92.
19. Ortega F J, Mercader J M, Moreno-Navarrete J M, Rovira O, Guerra E, Esteve E, et al. Profiling of circulating microRNAs reveals common microRNAs linked to type 2 diabetes that change with insulin sensitization. Diabetes care. 2014; 37 (5): 1375-83.
20. Bye A, Rosjo H, Aspenes S T, Condorelli G, Omland T, Wisloff U. Circulating microRNAs and aerobic fitness—the HUNT-Study. PloS one. 2013; 8 (2): e57496.
21. Wang Y, Dai W, Chu X, Yang B, Zhao M, Sun Y. Metformin inhibits lung cancer cells proliferation through repressing microRNA-222. Biotechnology letters. 2013 December; 35 (12): 2013-9.
22. Yu Y, Kanwar S S, Patel B B, Oh P S, Nautiyal J, Sarkar F H, et al. MicroRNA-21 induces stemness by downregulating transforming growth factor beta receptor 2 (TGF-betaR2) in colon cancer cells. Carcinogenesis. 2012 January; 33 (1): 68-76.
23. Nangia-Makker P, Yu Y, Vasudevan A, Farhana L, Rajendra S G, Levi E, et al. Metformin: a potential therapeutic agent for recurrent colon cancer. PloS one. 2014; 9 (1): e84369.
24. Wahdan-Alaswad R S, Cochrane D R, Spoelstra N S, Howe E N, Edgerton S M, Anderson S M, et al. Metformin-induced killing of triple-negative breast cancer cells is mediated by reduction in fatty acid synthase via miRNA-193b. Hormones & cancer. 2014 December; 5 (6): 374-89.
25. Li W, Yuan Y, Huang L, Qiao M, Zhang Y. Metformin alters the expression profiles of microRNAs in human pancreatic cancer cells. Diabetes research and clinical practice. 2012 May; 96 (2): 187-95.
26. Oliveras-Ferraros C, Cufi S, Vazquez-Martin A, Torres-Garcia V Z, Del Barco S, Martin-Castillo B, et al. Micro (mi) RNA expression profile of breast cancer epithelial cells treated with the anti-diabetic drug metformin: induction of the tumor suppressor miRNA let-7a and suppression of the TGFbeta-induced oncomiR miRNA-181a. Cell cycle (Georgetown, Tex). 2011 Apr. 1; 10 (7): 1144-51.
27. Bibikova E, Youn M Y, Danilova N, Ono-Uruga Y, Konto-Ghiorghi Y, Ochoa R, et al. TNF-mediated inflammation represses GATA1 and activates p38 MAP kinase in RPS19-deficient hematopoietic progenitors. Blood. 2014 Dec. 11; 124 (25): 3791-8.
28. Narla A, Vlachos A, Nathan D G. Diamond Blackfan anemia treatment: past, present, and future. Seminars in hematology. 2011 April; 48 (2): 117-23.
29. Morgado-Palacin L, Varetti G, Llanos S, Gomez-Lopez G, Martinez D, Serrano M. Partial Loss of Rpl11 in Adult Mice Recapitulates Diamond-Blackfan Anemia and Promotes Lymphomagenesis. Cell reports. 2015 Oct. 27; 13 (4): 712-22.
30. Wilkes M C, Siva K, Chen J, Varetti G, Dever D P, Nishimura T, et al. Diamond Blackfan Anemia is mediated by Hyperactive Nemo-like Kinase. Under Review. 2018.
31. Flygare J, Kiefer T, Miyake K, Utsugisawa T, Hamaguchi I, Da Costa L, et al. Deficiency of ribosomal protein S19 in CD34+ cells generated by siRNA blocks erythroid development and mimics defects seen in Diamond-Blackfan anemia. Blood. 2005 Jun. 15; 105 (12): 4627-34.
32. Miyake K, Flygare J, Kiefer T, Utsugisawa T, Richter J, Ma Z, et al. Development of cellular models for ribosomal protein S19 (RPS19)-deficient diamond-blackfan anemia using inducible expression of siRNA against RPS19. Molecular therapy: the journal of the American Society of Gene Therapy. 2005 April; 11 (4): 627-37.
33. Jaako P, Flygare J, Olsson K, Quere R, Ehinger M, Henson A, et al. Mice with ribosomal protein S19 deficiency develop bone marrow failure and symptoms like patients with Diamond-Blackfan anemia. Blood. 2011 Dec. 1; 118 (23): 6087-96.
34. Danilova N, Sakamoto K M, Lin S. Ribosomal protein S19 deficiency in zebrafish leads to developmental abnormalities and defective erythropoiesis through activation of p53 protein family. Blood. 2008 Dec. 15; 112 (13): 5228-37.
35. Chen H W, Qiao H Y, Li H C, Li Z F, Zhang H J, Pei L, et al. Prognostic significance of Nemo-like kinase expression in patients with hepatocellular carcinoma. Tumour biology: the journal of the International Society for Oncodevelopmental Biology and Medicine. 2015 November; 36 (11): 8447-53.
36. Didiano D, Hobert O. Molecular architecture of a miRNA-regulated 3' UTR. Rna. 2008 July; 14 (7): 1297-317.
37. Li X, Zhang J, Gao L, Mcclellan S, Finan M A, Butler T W, et al. MiR-181 mediates cell differentiation by interrupting the Lin28 and let-7 feedback circuit. Cell death and differentiation. 2012 March; 19 (3): 378-86.
38. Zimmerman El, Dollins C M, Crawford M, Grant S, Nana-Sinkam S P, Richards K L, et al. Lyn kinase-dependent regulation of miR181 and myeloid cell leukemia-1 expression: implications for drug resistance in myelogenous leukemia. Molecular pharmacology. 2010 November; 78 (5): 811-7.
39. Weng H, Lal K, Yang F F, Chen J. The pathological role and prognostic impact of miR-181 in acute myeloid leukemia. Cancer genetics. 2015 May; 208 (5): 225-9.
40. Li Q J, Chau J, Ebert P J, Sylvester G, Min H, Liu G, et al. miR-181a is an intrinsic modulator of T cell sensitivity and selection. Cell. 2007 Apr. 6; 129 (1): 147-61.
41. Su R, Lin H S, Zhang X H, Yin X L, Ning H M, Liu B, et al. MiR-181 family: regulators of myeloid differentiation and acute myeloid leukemia as well as potential therapeutic targets. Oncogene. 2015 June; 34 (25): 3226-39.
42. Taylor A M, Humphries J M, White R M, Murphey R D, Burns C E, Zon L I. Hematopoietic defects in rps29 mutant zebrafish depend upon p53 activation. Experimental hematology. 2012 March; 40 (3): 228-37.e5.
43. Thorpe C J, Moon R T. nemo-like kinase is an essential co-activator of Wnt signaling during early zebrafish development. Development (Cambridge, England). 2004 June; 131 (12): 2899-909.
44. Steffensen L B, Feddersen S, Preil S R, Rasmussen L M. No detectable differential microRNA expression between non-atherosclerotic arteries of type 2 diabetic patients (treated or untreated with metformin) and non-diabetic patients. Cardiovascular diabetology. 2018 May 17; 17 (1): 72.
45. Katsura A, Morishita A, Iwama H, Tani J, Sakamoto T, Tatsuta M, et al. MicroRNA profiles following metformin treatment in a mouse model of non-alcoholic steatohepatitis. International journal of molecular medicine. 2015 April; 35 (4): 877-84.
46. Wang Z, Zhang D, Hu Z, Cheng J, Zhuo C, Fang X, et al. MicroRNA-26a-modified adipose-derived stem cells incorporated with a porous hydroxyapatite scaffold improve the repair of bone defects. Molecular medicine reports. 2015 September; 12 (3): 3345-50.
47. Cabello P, Pineda B, Tormo E, Lluch A, Eroles P. The Antitumor Effect of Metformin Is Mediated by miR-26a in Breast Cancer. International journal of molecular sciences. 2016 Aug. 10; 17 (8).
48. Kota J, Chivukula R R, O'Donnell K A, Wentzel E A, Montgomery C L, Hwang H W, et al. Therapeutic microRNA delivery suppresses tumorigenesis in a murine liver cancer model. Cell. 2009 Jun. 12; 137 (6): 1005-17.
49. Zhang B, Liu X X, He J R, Zhou C X, Guo M, He M, et al. Pathologically decreased miR-26a antagonizes apoptosis and facilitates carcinogenesis by targeting MTDH and EZH2 in breast cancer. Carcinogenesis. 2011 January; 32 (1): 2-9.
50. Suh J H, Choi E, Cha M J, Song B W, Ham O, Lee S Y, et al. Up-regulation of miR-26a promotes apoptosis of hypoxic rat neonatal cardiomyocytes by repressing GSK-3beta protein expression. Biochemical and biophysical research communications. 2012 Jun. 29; 423 (2): 404-10.
51. Xu B Y, Li Y L, Luan B, Zhang Y L, Jia™, Qiao J Y. MIR-26a protects type II alveolar epithelial cells against mitochondrial apoptosis. European review for medical and pharmacological sciences. 2018 January; 22 (2): 486-91.
52. Peng J, He X, Zhang L, Liu P. MicroRNA26a protects vascular smooth muscle cells against H2O2induced injury through activation of the PTEN/AKT/mTOR pathway. International journal of molecular medicine. 2018 September; 42 (3): 1367-78.
53. Tan S, Ding K, Chong Q Y, Zhao J, Liu Y, Shao Y, et al. Post-transcriptional regulation of ERBB2 by miR26a/b and HuR confers resistance to tamoxifen in estrogen receptor-positive breast cancer cells. The Journal of biological chemistry. 2017 Aug. 18; 292 (33): 13551-64.
54. Sekimoto N, Suzuki A, Suzuki Y, Sugano S. Expression of miR26a exhibits a negative correlation with HMGA1 and regulates cancer progression by targeting HMGA1 in lung adenocarcinoma cells. Molecular medicine reports. 2017 February; 15 (2): 534-42.
55. Zhang Y, Su Z, Liu H L, Li L, Wei M, Ge D J, et al. Effects of miR-26a-5p on neuropathic pain development by targeting MAPK6 in in CCI rat models. Biomedicine & pharmacotherapy=Biomedecine & pharmacotherapie. 2018 November; 107:644-9.
56. Emami K H, Brown L G, Pitts T E, Sun X, Vessella R L, Corey E. Nemo-like kinase induces apoptosis and inhibits androgen receptor signaling in prostate cancer cells. The Prostate. 2009 Oct. 1; 69 (14): 1481-92.
57. Wang J, Yang Z H, Chen H, Li H H, Chen L Y, Zhu Z, et al. Nemo-like kinase as a negative regulator of nuclear receptor Nurr1 gene transcription in prostate cancer. BMC cancer. 2016 Mar. 31; 16:257.
58. Jung K H, Kim J K, Noh J H, Eun J W, Bae H J, Xie H J, et al. Targeted disruption of Nemo-like kinase inhibits tumor cell growth by simultaneous suppression of cyclin D1 and CDK2 in human hepatocellular carcinoma. Journal of cellular biochemistry. 2010 Jun. 1; 110 (3): 687-96.
59. Sa J K, Yoon Y, Kim M, Kim Y, Cho H J, Lee J K, et al. In vivo RNAi screen identifies NLK as a negative regulator of mesenchymal activity in glioblastoma. Oncotarget. 2015 Aug. 21; 6 (24): 20145-59.

60. Chen J, Han Y, Zhao X, Yang M, Liu B, Xi X, et al. Nemolike kinase expression predicts poor survival in colorectal cancer. Molecular medicine reports. 2015 February; 11 (2): 1181-7.
61. Li S Z, Zeng F, Li J, Shu Q P, Zhang H H, Xu J, et al. Nemo-like kinase (NLK) primes colorectal cancer progression by releasing the E2F1 complex from HDAC1. Cancer letters. 2018 Sep. 1; 431:43-53.
62. Zhang X W, Chen S Y, Xue D W, Xu H H, Yang L H, Xu H T, et al. Expression of Nemo-like kinase was increased and negatively correlated with the expression of TCF4 in lung cancers. International journal of clinical and experimental pathology. 2015; 8 (11): 15086-92.
63. Zhang W, He J, Du Y, Gao X H, Liu Y, Liu Q Z, et al. Upregulation of nemo-like kinase is an independent prognostic factor in colorectal cancer. World journal of gastroenterology. 2015 Aug. 7; 21 (29): 8836-47.
64. Dong J R, Guo N, Zhao J P, Liu P D, Feng H H, Li Y. Inhibition of nemo-like kinase increases taxol sensitivity in laryngeal cancer. Asian Pacific journal of cancer prevention: APJCP. 2013; 14 (12): 7137-41.
65. Tai J, Rao Y, Fang J, Huang Z, Yu Z, Chen X, et al. Lentivirusdelivered nemolike kinase small interfering RNA inhibits laryngeal cancer cell proliferation in vitro. Molecular medicine reports. 2015 October; 12 (4): 5619-24.
66. Lv M, Li Y, Tian X, Dai S, Sun J, Jin G, et al. Lentivirus-mediated knockdown of NLK inhibits small-cell lung cancer growth and metastasis. Drug design, development and therapy. 2016; 10:3737-46.
67. Yasuda J, Ichikawa H. Mammalian Nemo-like kinase enhances beta-catenin-TCF transcription activity in human osteosarcoma and neuroblastoma cells. Proceedings of the Japan Academy Series B, Physical and biological sciences. 2007 February; 83 (1): 16-25.
68. Kortenjann M, Nehls M, Smith A J, Carsetti R, Schuler J, Kohler G, et al. Abnormal bone marrow stroma in mice deficient for nemo-like kinase, Nlk. European journal of immunology. 2001 December; 31 (12): 3580-7.
69. Ishitani T, Ishitani S. Nemo-like kinase, a multifaceted cell signaling regulator. Cellular signalling. 2013 January; 25 (1): 190-7.
70. Tanno T, Zhang P, Lazarski C A, Liu Y, Zheng P. An aptamer-based targeted delivery of miR-26a protects mice against chemotherapy toxicity while suppressing tumor growth. Blood advances. 2017 Jun. 27; 1 (15): 1107-19.

III. Ginsenoside Rb1 improves erythropoiesis in models of Diamond Blackfan Anemia by targeting Nemo-like Kinase A. Abstract Nemo-like kinase (NLK) is a member of the MAPK family of kinases and shares a highly conserved kinase domain with other family members. The activation of NLK contributes to the pathogenesis of Diamond Blackfan Anemia and is therefore a potential therapeutic target. We report that the active component of *ginseng*, ginsenoside Rb1, suppresses NLK and improves erythropoiesis in in vitro models of Diamond Blackfan Anemia. Ginsenoside does not inhibit NLK kinase activity directly, but rather suppresses expression of NLK. Ginsenoside Rb1-mediated NLK suppression is through the upregulation of miR-208, that binds to the 3'UTR of NLK mRNA to target it for degradation. Here we compare ginsenoside Rb1-mediated upregulation of miR-208 with metformin-upregulated miR-26 and demonstrate that targeting NLK expression through miRNA-mediated binding of the unique 3'UTR is a viable alternative to the challenges of developing small molecule inhibitors to the kinase domain of this highly conserved kinase.

Here, we report that ginsenoside Rb1 (the active component of *ginseng*) upregulates miR-208 in differentiating HSPCs. This upregulation targets NLK mRNA for degradation and reduces the amount of NLK protein available to be activated in ribosome insufficiency, thereby improving erythroid expansion in these cells. As this represents the second compound that utilizes this mechanism of action, we propose that targeting NLK expression with miRNAs is a viable alternative to small molecule kinase inhibitors that will likely be non-specific with significant off-target effects.

B. Results

As the suppression of NLK by miRNAs has been documented, we sought to screen a number of common nutritional supplements that have been documented to modulate miRNAs in their ability to improve erythroid expansion in an in vitro model of DBA. To induce ribosomal insufficiency, CD34+ HSPCs from human cord blood were transduced with a shRNA against RPS19 that reduced RPS19 expression by approximately 50% to recapitulate decreased function due to RPS19 mutations in DBA patients. As described above, metformin improves erythroid expansion by miRNA-mediated suppression of NLK mRNA expression and was therefore included as a positive control. Similar to metformin, 50 mM Ginsenoside Rb1 increased erythroid expansion by 2.6-fold (p=0.0488) in RPS19-insufficient hematopoietic progenitor cells but did not significantly impact erythropoiesis in healthy controls (p=0.9129). Ginsenoside Rb1 did not impact CD11b+ myeloid expansion in control or RPS19-insufficiency. Efficacy of shRNA against RPS19 was quantified by qRT-PCR. Ginsenoside Rb1 has an EC50 value of 2.3 mM with 90% potency achieved at 8.6 mM. To determine if the ginsenoside Rb1 effect was through the inhibition of NLK, we treated differentiating HSPCs with ginsenoside Rb1 that were transduced with a non-targeting control or siRNA against NLK. Ginsenoside R1 alone or siRNA against NLK alone improved erythroid expansion by 2.7- and 5.1-fold, respectively. The addition of ginsenoside Rb1 when NLK was suppressed by siRNA did not significantly influence erythroid differentiation (5.2-fold, p=0.9037), suggesting the mechanism of action of ginsenoside Rb1 in erythroid rescue in RPS19-insufficiency is through the partial inhibition of NLK.

To determine if the mechanism of action of ginsenoside Rb1 was through the direct inhibition of NLK kinase activity, we performed in vitro kinase assays examining the ability of purified pre-activated NLK to phosphorylate three NLK substrates (Raptor, c-Myb and NLK). Even at 500 mM ginsengoside-6p failed to inhibit NLK kinase activity. In contrast, the non-specific kinase inhibitor SD208 inhibited NLK from phosphorylating NLK, c-Myb and Raptor by 84.3, 79.7 and 89.1%, respectively, at 5 μM.

In differentiating RPS19-insufficient HSPCs, ginsenoside Rb1 did not influence RPS19 expression. In contrast, 50 mM ginsenoside Rb1 reduced NLK mRNA expression by 43.8% (p=0.0032) and 43.2% (p=0.003) in control and RPS19-insufficiency respectively. NLK protein was reduced in differentiating HSPCs by 31.5 and 46.4% at 5 and 50 mM ginsenoside R1b, respectively. As would be anticipated with reduced NLK expression, NLK immunopurified from equal numbers of ginsenoside Rb1-treated RPS19-insufficient progenitors demonstrated 44.8% reduced NLK kinase activity (p=0.017), correlating with the reduced NLK expression. As NLK is not activated in control cells, the reduction in expression does not reduce activity, further suggesting the reduction of NLK activity seen in RPS19-insufficieny, is due to a reduction in the number of activated NLK molecules.

Degradation initiated by miRNA typically requires binding of miRNAs to complementary sequences in the mRNA 3'UTR. To address whether NLK suppression by ginsenoside Rb1 in RPS19-insufficiency was due to miRNA-mediated events, we fused the NLK 5'UTR or 3'UTR to the luciferase gene and transduced them into ginsenoside Rb1-treated control and RPS19-insufficient differentiating HSPCs. As would be anticipated for a miRNA-mediated event, no downregulation of luciferase activity was observed upon expression of the NLK 5'UTR upstream of the luciferase, but the fusion of the NLK 3'UTR downstream of luciferase lead to a dose-dependent downregulation of luciferase activity. Luciferase activity was reduced by 35.9% (p=0.0072) at 50 mM ginsenoside Rb1 indicating the 3'UTR of NLK is required for NLK mRNA degradation.

The 3'UTR of NLK is 3745 residues and contains at least 30 predicted high potential miRNA binding sites (TargetScan 7.2). We generated a series of truncated NLK 3'UTRs fused to the luciferase gene and transduced them into control and RPS19-insufficient differentiating HSPCs. Cells were treated with increasing concentrations of ginsenoside Rb1 or metformin and luciferase activity assessed. 50 mM Ginsenoside Rb1 reduced luciferase activity by 35.9% (p=0.0072) while metformin reduced luciferase activity by 67.5% (p=0.0184). As previously observed, the ability of metformin to influence the NLK 3'UTR was lost upon truncation of residues between 1007 and 1268. The influence of ginsenoside Rb1 was lost upon truncation of a region between residues 1530 and 1792. The predicted miRNA binding sites contained within this region are miR-499, miR-208 and miR-132.

Comparison of miRNA expression in vehicle-, metformin- and ginsenoside Rb1-treated HSPCs revealed that of the 3 miRNAs predicted to bind the region of the NLK 3'UTR required for ginsenoside Rb1 sensitivity, only miR-208 was significantly upregulated (p=0.0137) and was induced by 1.9-fold. None of these miRNAs were induced by metformin since metformin induces miR-26 as shown above. The abundance of let-7, miR-30 miR-144 and miR-132 were expressed 40.1-, 2.2-, 5.0- and 18.3-fold higher than miR-208, whereas miR-208 was expressed 1.6- and 2.1-fold higher than miR-199 and miR-499. MiR-26a (induced by metformin) expression was 1.4-fold higher than miR-208.

To confirm miR-208 could downregulate endogenous NLK, we transduced a series of miRNA species into differentiating HSPCs. As has been reported, miR-181, miR-26, miR-199, miR-101 and miR-221 suppressed NLK expression by 85.6% (p=0.0035), 58.7% (p=0.0155), 80.8% (p=0.0026), 23.0% (p=0.0056) and 37.7% (p=0.0129) respectively. Expression of miR-208 reduced NLK expression by 40.2% (p=0.0093) which correlates closely with the influence of ginsenoside Rb1 (34.6%). Expression of miRNAs is quantified by qRT-PCR.

We further examined if the expression of various combinations of these miRNAs suppressed NLK expression more than single miRNAs alone. MiR-199 suppressed NLK expression better than other miRNA species, reducing NLK expression to 19.2% of control. Expression of two or more miRNAs generally decreased NLK expression, although the synergistic effect varied with each combination. Maximal suppression by a single miRNA was 80.8% (by miR-199) with a maximal effect observed upon combining all 5 miRNAs with NLK expression reduced to 2.2% (p=0.0003) of control. The combined properties did not strongly correlate with the suppressive effect of each individual miRNA, suggesting a complex interplay between miRNAs, the degradative machinery and the NLK 3'UTR. Combined ginsenoside Rb1 and metformin treatment further decreased NLK expression down to 21.4% of control, from 65.4% and 40.6% with ginsenoside Rb1 or metformin alone (p=0.0048 and 0.025 respectively).

Having established that miR-208 is upregulated in response to ginsenoside Rb1 and that miR-208 suppresses NLK expression, we sought to test the hypothesis that ginsenoside Rb1-mediated upregulation of miR-208 is responsible for ginsenoside Rb1-mediated suppression of NLK expression. To address this, various inhibitors of miRNAs (miRNA sponges) were transduced into ginsenoside Rb1- or metformin-treated differentiating HSPCs. Expression of miRNAs was assessed by qRT-PCR. As anticipated, miR-26 inhibition prevented metformin-induced NLK suppression. Ginsenoside Rb1 treatment reduced endogenous NLK expression by 44.8% (p=0.0065), but inhibition of miR-208 rescued this back to 94.1% of control (p=0.0076). This indicates ginsenoside Rb1 indeed suppresses NLK expression through the induction of miR-208.

Having confirmed ginsenoside Rb1-mediated upregulation of miR-208 is responsible for the suppression of NLK in differentiating HSPCs, our final goal was to assess if upregulation of miR-208 indeed accounted for the improved erythropoiesis in response to ginsenoside Rb1. CB CD34+ HSPCs were transduced with control or shRNA against RPS19 in combination with metformin or ginsenoside Rb1 and/or miR-26 or miR-208. As anticipated, miR-26 restored erythropoiesis in RPS19-insufficiency to a similar extent as metformin. Similarly, miR-208 increased erythroid expansion by 2.65-fold (p=0.0473) and ginsenoside Rb1 increased it by 2.52-fold (p=0.1416). As combining miR-208 with ginsenoside Rb1 did not significantly increase erythropoiesis compared to either treatment alone (2.57-fold to 2.65-fold and 2.52-fold respectively) (p=0.8801 and 0.9432), it is highly probable that the ginsenoside Rb1 rescue is mediated primarily through miR-208 upregulation. No significant impact on CD11b+ myeloid expansion was observed in response to drug or miRNA manipulation.

While erythroid expansion is improved in RPS19-insufficiency, there is no impact on healthy controls, but examination indicates that NLK expression is similarly suppressed by each treatment in both healthy controls and RPS19-insufficiency. This reflects the fact that NLK is dispensable for healthy erythropoiesis and only impacts erythroid expansion once it is activated in ribosomal insufficiency. RPS19 and miRs-208 and -26 expression were assessed. As the combination of ginsenoside Rb1 and metformin further suppressed NLK expression from 34.6% and 59.4% alone to 78.6%, we sought to determine if combining metformin and ginsenoside Rb1 could act synergistically to improve erythroid expansion in RPS19-insufficiency. Ginsenoside Rb1 (50 mM) and metformin (50 mM) were combined and added to HSPCs transduced with shRNA against RPS19 or control. The combined treatment further enhanced erythroid expansion in RPS19-insufficiency from 20.9% and 28.4% when cells were treated with either ginsenoside Rb1 or metformin alone, to 37.1% (p=0.0091 and 0.0306) when treated in combination. No significant toxicity was observed in healthy erythroid. NLK 3'UTR-regulated luciferase activity was inversely proportionally reduced with co-treatment significantly decreasing NLK expression compared to either drug alone (p=0.005 and 0.0164 respectively). While this study is focused on documenting the mechanism of ginsenoside Rb1-mediated erythroid rescue in DBA models, these data suggests combining ginsenoside Rb1 (or other modulators of miR-208 expression) may have additional therapeutic benefit to other therapies that may suppress NLK expression/activity by other mechanisms. While combination therapy was not additive, significant synergy was observed with combination index (CI) values of 0.83, 0.69 and 0.58 at 50%, 70% and 90% of maximal erythroid rescue values.

Collectively, our data show that ginsenoside Rb1 induces miR-208 upregulation in differentiating erythroid progenitors that suppresses NLK expression. In RPS19-insufficiency, the reduced NLK expression protects progenitors from the impacts of NLK activation and improves erythroid expansion.

IV. Nemo-like kinase (NLK) is hyperactivated in red cell precursors in the bone marrow of patients with DBA. Inhibition of NLK by knockdown or chemical compounds in our in vitro DBA models results in improvement of red cell production. Regardless of the underlying genetic mutation causing DBA, NLK is hyperactivated. We have tested the FDA approved drug OTS167 in DBA models and have shown that not only does this drug inhibit NLK, but it improves red cell production in vitro without toxicity to normal bone marrow cells. Our goal is to next test OTS167 in mouse models of DBA. According to clinical trials.gov, OTS167 is currently in trials for AML, ALL, MDS, MPN, and CML, solid tumors, and breast cancer, but not DBA. This is the first example of a targeted therapy for all DBA patient regardless of the underlying mutations. Giving this drug would be easier and cheaper than gene editing to correct the gene defect.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112 (f) or 35 U.S.C. § 112 (6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112 (6) is not invoked.

What is claimed is:

1. A method of treating a subject diagnosed as having a bone marrow failure syndrome, the method comprising: administering to the subject an effective amount of a nemo-like kinase (NLK) inhibitor to treat the subject for the bone marrow failure syndrome.

2. The method according to claim 1, wherein the inhibitor comprises a small molecule.

3. The method according to claim 2, wherein the small molecule is selected from the group consisting of: OTS167, INK128, AST487, BIRB796, SB203580, SD208, SB431542 and Galunisertib.

4. The method according to claim 3, wherein the small molecule is OTS167.

5. The method according to claim 1, wherein the NLK inhibitor comprises an NLK specific binding member.

6. The method according to claim 5, wherein the NLK specific binding member comprises an antibody or binding fragment thereof.

7. The method according to claim 1, wherein the NLK inhibitor comprises an NLK expression inhibiting agent.

8. The method according to claim 7, wherein the NLK expression inhibiting agent comprises a nucleic acid.

9. The method according to claim 8, wherein the nucleic acid is a micro-RNA.

10. The method according to claim 9, wherein the micro-RNA is miR-26a, miR-208 or miR-181.

11. The method according to claim 7, wherein the NLK expression inhibiting agent is metformin or ginsenoside Rb1.

12. The method according to claim 1, wherein administration of the NLK inhibitor increases erythroid expansion.

* * * * *